US011299776B2

(12) United States Patent
Ellington et al.

(10) Patent No.: US 11,299,776 B2
(45) Date of Patent: Apr. 12, 2022

(54) METHODS AND DEVICES RELATED TO AMPLIFYING NUCLEIC ACID AT A VARIETY OF TEMPERATURES

(71) Applicant: BOARD OF REGENTS, THE UNIVERSITY OF TEXAS SYSTEM, Austin, TX (US)

(72) Inventors: Andrew Ellington, Austin, TX (US); Cheulhee Jung, Austin, TX (US); Sheng Cai, Zhejiang (CN); Sanchita Bhadra, Austin, TX (US); John N. Milligan, Austin, TX (US); Daniel Garry, Austin, TX (US); Raghav Shroff, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/612,020

(22) PCT Filed: May 10, 2018

(86) PCT No.: PCT/US2018/032074
§ 371 (c)(1),
(2) Date: Nov. 8, 2019

(87) PCT Pub. No.: WO2018/209092
PCT Pub. Date: Nov. 15, 2018

(65) Prior Publication Data
US 2020/0255891 A1 Aug. 13, 2020

Related U.S. Application Data

(60) Provisional application No. 62/504,250, filed on May 10, 2017.

(51) Int. Cl.
*C12N 9/12* (2006.01)
*C12Q 1/6853* (2018.01)
*C12Q 1/686* (2018.01)

(52) U.S. Cl.
CPC ......... *C12Q 1/6853* (2013.01); *C12N 9/1252* (2013.01); *C12Q 1/686* (2013.01);
(Continued)

(58) Field of Classification Search
None
See application file for complete search history.

(56) References Cited

U.S. PATENT DOCUMENTS 4,469,863 A    9/1984  Ts'o et al.
5,034,506 A    7/1991  Summerton et al.
(Continued)

FOREIGN PATENT DOCUMENTS

WO    2009/049630    4/2009

OTHER PUBLICATIONS

Ngo et al. in The Protein Folding Problem and Tertiary Structure Prediction, 1994, Merz et al. (ed.), Birkhauser, Boston, MA, pp. 433 and 492-495.*

(Continued)

*Primary Examiner* — Richard G Hutson
(74) *Attorney, Agent, or Firm* — Meunier Carlin & Curfman LLC

(57) ABSTRACT

Disclosed are compositions and methods for nucleic acid amplification and detection. Specifically, disclosed herein are compositions and methods that allow for amplification of nucleic acids at a wide variety of temperatures. This includes a polymerase which is thermostable at high temperatures, and a method of amplification that can be conducted at relatively low temperatures.

8 Claims, 34 Drawing Sheets

Specification includes a Sequence Listing.

(52) U.S. Cl.
CPC .. *C12Q 2521/101* (2013.01); *C12Q 2525/301* (2013.01); *C12Q 2527/101* (2013.01); *C12Q 2531/101* (2013.01); *C12Q 2537/1373* (2013.01); *C12Q 2600/158* (2013.01)

(56) References Cited

U.S. PATENT DOCUMENTS

| | | | |
|---|---|---|---|
| 5,216,141 | A | 6/1993 | Benner |
| 5,235,033 | A | 8/1993 | Summerton et al. |
| 5,386,023 | A | 1/1995 | Sanghvi et al. |
| 5,602,240 | A | 2/1997 | Mesmaeker et al. |
| 5,637,684 | A | 6/1997 | Cook et al. |
| 5,644,048 | A | 7/1997 | Yau |
| 6,942,771 | B1 | 9/2005 | Kayyem |
| 7,514,210 | B2 | 4/2009 | Holliger et al. |
| 7,618,773 | B2 | 11/2009 | Rand et al. |
| 7,972,830 | B2 * | 7/2011 | Meier ............ C12N 9/1252 435/194 |
| 9,085,762 | B2 * | 7/2015 | Hogrefe ............ C12N 9/1252 |
| 9,157,073 | B1 | 10/2015 | Ong et al. |
| 9,353,393 | B2 | 5/2016 | Nelson et al. |
| 9,546,358 | B2 | 1/2017 | Tanner et al. |
| 2006/0068378 | A1 | 3/2006 | Mirkin et al. |
| 2016/0076083 | A1 | 3/2016 | Ellington et al. |
| 2016/0145588 | A1 | 5/2016 | Ignatov et al. |
| 2016/0160193 | A1 | 6/2016 | Hsieh et al. |
| 2017/0067117 | A1 | 3/2017 | Xu et al. |

OTHER PUBLICATIONS

Abdulmawjood, A.; Wickhorst, J.; Hashim, O.; Sammra, O.; Hassan, A. A.; Alssahen, M.; Lammler, C.; Prenger-Berninghoff, E.; Klein, G., Application of a loop-mediated isothermal amplification (LAMP) assay for molecular identification of Trueperella pyogenes isolated from various origins. Molecular and Cellular Probes 2016, 30, (4), 205-210.

An, L., Tang, W., Ranalli, T.A., Kim, H.J., Wytiaz, J. and Kong, H. (2005) Characterization of a thermostable UvrD helicase and its participation in helicase-dependent amplification. The Journal of biological chemistry, 280, 28952-28958.

Aryan, E., Makvandi, M., Farajzadeh, A., Huygen, K., Bifani, P., Mousavi, S.L., Fateh, A., Jelodar, A., Gouya, M.M. and Romano, M. (2010) A novel and more sensitive loop-mediated isothermal amplification assay targeting IS6110 for detection of *Mycobacterium tuberculosis* complex. Microbiological research, 165, 211-220.

Asiello, P.J. and Baeumner, A.J. (2011) Miniaturized isothermal nucleic acid amplification, a review. Lab on a chip, 11, 1420-1430.

Baar, C., d'Abbadie, M., Vaisman, A., Arana, M.E., Hofreiter, M., Woodgate, R., Kunkel, T.A. and Holliger, P. (2011) Molecular breeding of polymerases for resistance to environmental inhibitors. Nucleic acids research, 39, e51.

Beaucage, Serge L., and Radhakrishnan P. Iyer. "The functionalization of oligonucleotides via phosphoramidite derivatives." Tetrahedron 49.10 (1993): 1925-1963.

Berman, H.M., Westbrook, J., Feng, Z., Gilliland, G., Bhat, T.N., Weissig, H., Shindyalov, I.N. and Bourne, P.E. (2000) The Protein Data Bank. Nucleic acids research, 28, 235-242.

Bhadra, S., Jiang, Y.S., Kumar, M.R., Johnson, R.F., Hensley, L.E. and Ellington, A.D. (2015) Real-Time Sequence-Validated Loop-Mediated Isothermal Amplification Assays for Detection of Middle East Respiratory Syndrome Coronavirus (MERS-CoV). PloS one, 10, e0123126.

Blanco, L. and Salas, M. (1984) Characterization and purification of a phage phi 29-encoded DNA polymerase required for the initiation of replication. Proceedings of the National Academy of Sciences of the United States of America, 81, 5325-5329.

Blanco, L., Bernad, A., Lazaro, J.M., Martin, G., Garmendia, C. and Salas, M. (1989) Highly efficient DNA synthesis by the phage phi 29 DNA polymerase. Symmetrical mode of DNA replication. The Journal of biological chemistry, 264, 8935-8940.

Boczkowska, M.; Guga, P.; Stec, W. J., Stereodefined phosphorothioate analogues of DNA: Relative thermodynamic stability of the model PS-DNA/DNA and PS-DNA/RNA complexes. Biochemistry 2002, 41, (41), 12483-12487.

Borysiak, M.D., Kimura, K.W. and Posner, J.D. (2015) NAIL: Nucleic Acid detection using Isotachophoresis and Loop-mediated isothermal amplification. Lab on a chip, 15, 1697-1707.

Brill, Wolfgang KD, et al. "Synthesis of oligodeoxynucleoside phosphorodithioates via thioamidites." Journal of the American Chemical Society 111.6 (1989): 2321-2322.

Carlsson, Christina, et al. Screening for genetic mutations. Nature 380.6571 (1996): 207-207.

Chander, Y., Koelbl, J., Puckett, J., Moser, M.J., Klingele, A.J., Liles, M.R., Carrias, A., Mead, D.A. and Schoenfeld, T.W. (2014) A novel thermostable polymerase for RNA and DNA loop-mediated isothermal amplification (LAMP). Front Microbiol, 5, 395.

Chang, Y. X.; Gong, L.; Yuan, W. Y.; Li, X. W.; Chen, G. X.; Li, X. H.; Zhang, Q. F.; Wu, C. Y., Replication Protein A (RPA1a) Is Required for Meiotic and Somatic DNA Repair But Is Dispensable for DNA Replication and Homologous Recombination in Rice. Plant Physiology 2009, 151, (4), 2162-2173.

Chen, T. and Romesberg, F.E. (2014) Directed polymerase evolution. FEBS Lett, 588, 219-229.

Chen, T., Hongdilokkul, N., Liu, Z., Adhikary, R., Tsuen, S.S. and Romesberg, F.E. (2016) Evolution of thermophilic DNA polymerases for the recognition and amplification of C2'-modified DNA. Nature chemistry, 8, 556-562.

Conway, B. E., Effect of Urea on the Viscosity of Deoxyribonucleic Acid Solutions. Journal of Polymer Science 1956, 20, (95), 299-306.

Crameri, A., Raillard, S.A., Bermudez, E. and Stemmer, W.P. (1998) DNA shuffling of a family of genes from diverse species accelerates directed evolution. Nature, 391, 288-291.

Craw, P. and Balachandran, W. (2012) Isothermal nucleic acid amplification technologies for point-of-care diagnostics: a critical review. Lab on a chip, 12, 2469-2486.

Dean, F.B., Nelson, J.R., Giesler, T.L. and Lasken, R.S. (2001) Rapid amplification of plasmid and phage DNA using Phi 29 DNA polymerase and multiply-primed rolling circle amplification. Genome Res, 11, 1095-1099.

Dempcy, Robert O., Kenneth A. Browne, and Thomas C. Bruice. "Synthesis of a thymidyl pentamer of deoxyribonucleic guanidine and binding studies with DNA homopolynucleotides." Proceedings of the National Academy of Sciences 92.13 (1995): 6097-6101.

Du, Y., Hughes, R.A., Bhadra, S., Jiang, Y.S., Ellington, A.D. and Li, B. (2015) A Sweet Spot for Molecular Diagnostics: Coupling Isothermal Amplification and Strand Exchange Circuits to Glucometers. Sci Rep, 5, 11039.

Egholm, Michael, et al. "Peptide nucleic acids (PNA). Oligonucleotide analogs with an achiral peptide backbone." Journal of the American Chemical Society 114.5 (1992): 1895-1897.

Ellefson, J.W., Gollihar, J., Shroff, R., Shivram, H., Iyer, V.R. and Ellington, A.D. (2016) Synthetic evolutionary origin of a proof-reading reverse transcriptase. Science, 352, 1590-1593.

Ellefson, J.W., Meyer, A.J., Hughes, R.A., Cannon, J.R., Brodbelt, J.S. and Ellington, A.D. (2014) Directed evolution of genetic parts and circuits by compartmentalized partnered replication. Nature biotechnology, 32, 97-101.

Fereidouni, S.R., Starick, E., Ziller, M., Harder, T.C., Unger, H., Hamilton, K. and Globig, A. (2015) Sample preparation for avian and porcine influenza virus cDNA amplification simplified: Boiling vs. conventional RNA extraction. J Virol Methods, 221, 62-67.

Ghadessy, F.J., Ong, J.L. and Holliger, P. (2001) Directed evolution of polymerase function by compartmentalized self-replication. Proceedings of the National Academy of Sciences of the United States of America, 98, 4552-4557.

Ghadessy, F.J., Ramsay, N., Boudsocq, F., Loakes, D., Brown, A., Iwai, S., Vaisman, A., Woodgate, R. and Holliger, P. (2004) Generic expansion of the substrate spectrum of a DNA polymerase by directed evolution. Nature biotechnology, 22, 755-759.

Gill, P. and Ghaemi, A. (2008) Nucleic Acid Isothermal Amplification Technologies—A Review. Nucleosides, Nucleotides & Nucleic Acids, 27, 224-243.

(56) References Cited

OTHER PUBLICATIONS

Hartman, M.R., Ruiz, R.C., Hamada, S., Xu, C., Yancey, K.G., Yu, Y., Han, W. and Luo, D. (2013) Point-of-care nucleic acid detection using nanotechnology. Nanoscale, 5, 10141-10154.

Hoheisel, J.D. (1993) On the activities of *Escherichia coli* exonuclease III. Analytical biochemistry, 209, 238-246.

Hsieh, K., Mage, P.L., Csordas, A.T., Eisenstein, M. and Soh, H.T. (2014) Simultaneous elimination of carryover contamination and detection of DNA with uracil-DNA-glycosylase-supplemented loop-mediated isothermal amplification (UDG-LAMP). Chemical communications, 50, 3747-3749.

Ignatov, K.B., Barsova, E.V., Fradkov, A.F., Blagodatskikh, K.A., Kramarova, T.V. and Kramarov, V.M. (2014) A strong strand displacement activity of thermostable DNA polymerase markedly improves the results of DNA amplification. Biotechniques, 57, 81-87.

James, C.D. and Leffak, I.M. (1984) Replacement synthesis labeling of DNA molecules in vitro using the *Escherichia coli* exonuclease III/DNA polymerase I enzyme pair. Analytical biochemistry, 141, 33-37.

Jeffs et al., Unusual conformation of a 3'-thioformacetal linkage in a DNA duplex J. Biomolecular NMR (1994) 34:17.

Jiang, Y.S., Bhadra, S., Li, B., Wu, Y.R., Milligan, J.N. and Ellington, A.D. (2015) Robust strand exchange reactions for the sequence-specific, real-time detection of nucleic Acid amplicons. Analytical chemistry, 87, 3314-3320.

Jiang, Y.S., Li, B., Milligan, J.N., Bhadra, S. and Ellington, A.D. (2013) Real-time detection of isothermal amplification reactions with thermostable catalytic hairpin assembly. Journal of the American Chemical Society, 135, 7430-7433.

Jung C; A.D, E., A primerless molecular diagnostic: phosphorothioated-terminal hairpin formation and self-priming extension (PS-THSP). Analytical and Bioanalytical Chemistry 2016, 408(30): 8583-8591.

Kato, T.; Liang, X. G.; Asanuma, H., Model of Elongation of Short DNA Sequence by Thermophilic DNA Polymerase under Isothermal Conditions. Biochemistry 2012, 51, (40), 7846-7853.

Von Kiedrowski, Günter, et al. "Parabolic Growth of a Self-Replicating Hexadeoxynucleotide Bearing a 3'-5'-Phosphoamidate Linkage." Angewandte Chemie International Edition in English 30.4 (1991): 423-426.

Kiefer, J.R., Mao, C., Braman, J.C. and Beese, L.S. (1998) Visualizing DNA replication in a catalytically active Bacillus DNA polymerase crystal. Nature, 391, 304-307.

Kiefer, J.R., Mao, C., Hansen, C.J., Basehore, S.L., Hogrefe, H.H., Braman, J.C. and Beese, L.S. (1997) Crystal structure of a thermostable Bacillus DNA polymerase I large fragment at 2.1 A resolution. Structure, 5, 95-108.

Kim, T.H., Park, J., Kim, C.J. and Cho, Y.K. (2014) Fully integrated lab-on-a-disc for nucleic acid analysis of food-bome pathogens. Analytical chemistry, 86, 3841-3848.

Kong, H., Kucera, R.B. and Jack, W.E. (1993) Characterization of a DNA polymerase from the hyperthermophile archaea Thermococcus litoralis. Vent DNA polymerase, steady state kinetics, thermal stability, processivity, strand displacement, and exonuclease activities. The Journal of biological chemistry, 268, 1965-1975.

Kong, X. J.; Qin, W. T.; Huang, X. Q.; Kong, F. F.; Schoen, C. D.; Feng, J.; Wang, Z. Y.; Zhang, H., Development and application of loop-mediated isothermal amplification (LAMP) for detection of Plasmopara viticola. Scientific Reports 2016, 6:28935.

Korolev, S., Nayal, M., Barnes, W.M., Di Cera, E. and Waksman, G. (1995) Crystal structure of the large fragment of Thermus aquaticus DNA polymerase I at 2.5-A resolution: structural basis for thermostability. Proceedings of the National Academy of Sciences of the United States of America, 92, 9264-9268.

Koshkin, Alexei A., et al. "LNA (locked nucleic acid): an RNA mimic forming exceedingly stable LNA: LNA duplexes." Journal of the American Chemical Society 120.50 (1998): 13252-13253.

Kostner, M., Schmidt, B., Bertram, R. and Hillen, W. (2006) Generating tetracycline-inducible auxotrophy in *Escherichia coli* and *Salmonella enterica* serovar Typhimurium by using an insertion element and a hyperactive transposase. Applied and environmental microbiology, 72, 4717-4725.

Kozak, M., Evans, M., Gardner, P. D., Flores, I., Mariano, T. M., Pestka, S., . . . & Honda, G. (1991). Structural features in eukaryotic mRNAs that mod. Biol Chem, 266, 19867-19870.

Kunkel et al. Rapid and Efficient Site-Specific Mutagenesis Without Phenotypic Selection. Methods Enzymol. 1987:154:367-82, 1987.

Laos, R., Shaw, R., Leal, N.A., Gaucher, E. and Benner, S. (2013) Directed evolution of polymerases to accept nucleotides with non-standard hydrogen bond patterns. Biochemistry, 52, 5288-5294.

Laplanche, L. A.; James, T. L.; Powell, C.; Wilson, W. D.; Uznanski, B.; Stec, W. J.; Summers, M. F.; Zon, G., Phosphorothioate-Modified Oligodeoxyribonucleotides .3. Nmr and Uv Spectroscopic Studies of the Rp-Rp, Sp-Sp, and Rp-Sp Duplexes, [D(Ggsaattcc)]2, Derived from Diastereomeric O-Ethyl Phosphorothioates. Nucleic Acids Research 1986, 14, (22), 9081-9093.

Lawyer, F.C., Stoffel, S., Saiki, R.K., Chang, S.Y., Landre, P.A., Abramson, R.D. and Gelfand, D.H. (1993) High-level expression, purification, and enzymatic characterization of full-length Thermus aquaticus DNA polymerase and a truncated form deficient in 5' to 3' exonuclease activity. PCR Methods Appl, 2, 275-287.

Leconte, A.M., Patel, M.P., Sass, L.E., McInerney, P., Jarosz, M., Kung, L., Bowers, J.L., Buzby, P.R., Efcavitch, J.W. and Romesberg, F.E. (2010) Directed evolution of DNA polymerases for next-generation sequencing. Angewandte Chemie, 49, 5921-5924.

Letsinger, R. L., Singman, C. N., Histand, G., & Salunkhe, M. (1988). Cationic oligonucleotides. Journal of the American Chemical Society, 110(13), 4470-4471.

Letsinger, R. L., Bach, S. A., & Eadie, J. S. (1986). Effects of pendant groups at phosphorus on binding properties of d-ApA analogues. Nucleic acids research, 14(8), 3487-3499.

Jung, Paul M., Gary Histand, and Robert L. Letsinger. "Hybridization of alternating cationic/anionic oligonucleotides to RNA segments." Nucleosides, Nucleotides & Nucleic Acids 13.6-7 (1994): 1597-1605.

Letsinger, R. L., & Mungall, W. S. (1970). Nucleotide chemistry. XVI. Phosporamidate analogs of oligonucleotides. The Journal of organic chemistry, 35(11), 3800-3803.

Li, Y., Korolev, S. and Waksman, G. (1998) Crystal structures of open and closed forms of binary and ternary complexes of the large fragment of Thermus aquaticus DNA polymerase I: structural basis for nucleotide incorporation. EMBO J, 17, 7514-7525.

Liu, C., Geva, E., Mauk, M., Qiu, X., Abrams, W.R., Malamud, D., Curtis, K., Owen, S.M. and Bau, H.H. (2011) An isothermal amplification reactor with an integrated isolation membrane for point-of-care detection of infectious diseases. The Analyst, 136, 2069-2076.

Lizardi, P.M., Huang, X., Zhu, Z., Bray-Ward, P., Thomas, D.C. and Ward, D.C. (1998) Mutation detection and single-molecule counting using isothermal rolling-circle amplification. Nature genetics, 19, 225-232.

Lutz, R. and Bujard, H. (1997) Independent and Tight Regulation of Transcriptional Units in *Escherichia Coli* Via the LacR/O, the TetR/O and AraC/I1-I2 Regulatory Elements. Nucleic acids research, 25, 1203-1210.

Mag, M., Silke, L., & Engels, J. W. (1991). Synthesis and selective cleavage of an oligodeoxynucleotide containing a bridged internucleotide 5'-phosphorothioate linkage. Nucleic acids research, 19(7), 1437-1441.

Mahalanabis, M., Do, J., H, A.L., Zhang, J.Y. and Klapperich, C.M. (2010) An integrated disposable device for DNA extraction and helicase dependent amplification. Biomed Microdevices, 12, 353-359.

Mair, G.; Vilei, E. M.; Wade, A.; Frey, J.; Unger, H., Isothermal loop-mediated amplification (lamp) for diagnosis of contagious bovine pleuro-pneumonia. Bmc Veterinary Research 2013, 9, 108.

Mattes, J., Yang, M., & Foster, P. S. (2007). Regulation of microRNA by antagomirs: a new class of pharmacological antagonists for the specific regulation of gene function? American journal of respiratory cell and molecular biology, 36(1), 8-12.

(56) References Cited

OTHER PUBLICATIONS

McClary, J., Ye, S.Y., Hong, G.F. and Witney, F. (1991) Sequencing with the large fragment of DNA polymerase I from Bacillus stearothermophilus. DNA Seq, 1, 173-180.

Meier, Chris, and Joachim W. Engels. "Peptide Nucleic Acids (PNAs)—Unusual Properties of Nonionic Oligonucleotide Analogues." Angewandte Chemie International Edition in English 31.8 (1992): 1008-1010.

De Mesmaeker, A., Waldner, A., Sanghvi, Y. S., & Lebreton, J. (1994). Comparison of rigid and flexible backbones in antisense oligonucleotides. Bioorganic & Medicinal Chemistry Letters, 4(3), 395-398.

Meyer, A.J., Ellefson, J.W. and Ellington, A.D. (2015) Directed Evolution of a Panel of Orthogonal T7 RNA Polymerase Variants for in Vivo or in Vitro Synthetic Circuitry. ACS synthetic biology, 4, 1070-1076.

Milligan, J.N. and Garry, D.J. (2017) Shuffle Optimizer: A Program to Optimize DNA Shuffling for Protein Engineering. Methods Mol Biol, 1472, 35-45.

Modak, S.S., Barber, C.A., Geva, E., Abrams, W.R., Malamud, D. and Ongagna, Y.S. (2016) Rapid Point-of-Care Isothermal Amplification Assay for the Detection of Malaria without Nucleic Acid Purification. Infect Dis (Auckl), 9, 1-9.

Moore, G.L. and Maranas, C.D. (2000) Modeling DNA mutation and recombination for directed evolution experiments. Journal of theoretical biology, 205, 483-503.

Moore, G.L. and Maranas, C.D. (2002) eCodonOpt: a systematic computational framework for optimizing codon usage in directed evolution experiments. Nucleic acids research, 30, 2407-2416.

Moore, G.L., Maranas, C.D., Lutz, S. and Benkovic, S.J. (2001) Predicting crossover generation in DNA shuffling. Proceedings of the National Academy of Sciences of the United States of America, 98, 3226-3231.

Mori, Y., Kanda, H. and Notomi, T. (2013) Loop-mediated isothermal amplification (LAMP): recent progress in research and development. J Infect Chemother, 19, 404-411.

Nagamine, K.; Hase, T.; Notomi, T., Accelerated reaction by loop-mediated isothermal amplification using loop primers. Molecular and Cellular Probes 2002, 16, (3), 223-229.

Nagamine, K.; Kuzuhara, Y.; Notomi, T., Isolation of single-stranded DNA from loop-mediated isothermal amplification products. Biochemical and Biophysical Research Communications 2002, 290, (4), 1195-1198.

Nelson, J.R., Cai, Y.C., Giesler, T.L., Farchaus, J.W., Sundaram, S.T., Ortiz-Rivera, M., Hosta, L.P., Hewitt, P.L., Mamone, J.A., Palaniappan, C. et al. (2002) TempliPhi, phi29 DNA polymerase based rolling circle amplification of templates for DNA sequencing. Biotechniques, Suppl, 44-47.

Egholm, Michael, et al. "PNA hybridizes to complementary oligonucleotides obeying the Watson-Crick hydrogen-bonding rules." Nature 365.6446 (1993): 566-568.

Njiru, Z.K. (2012) Loop-mediated isothermal amplification technology: towards point of care diagnostics. PLoS Negl Trop Dis, 6, e1572.

Njiru, Z.K., Mikosza, A.S., Matovu, E., Enyaru, J.C., Ouma, J.O., Kibona, S.N., Thompson, R.C. and Ndung'u, J.M. (2008) African trypanosomiasis: sensitive and rapid detection of the sub-genus Trypanozoon by loop-mediated isothermal amplification (LAMP) of parasite DNA. Int J Parasitol, 38, 589-599.

Notomi, T., Okayama, H., Masubuchi, H., Yonekawa, T., Watanabe, K., Amino, N. and Hase, T. (2000) Loop-mediated isothermal amplification of DNA. Nucleic acids research, 28, E63.

Osada, H., & Takahashi, T. (2007). MicroRNAs in biological processes and carcinogenesis. Carcinogenesis, 28(1), 2-12.

Patel, P.H., Kawate, H., Adman, E., Ashbach, M. and Loeb, L.A. (2001) A single highly mutable catalytic site amino acid is critical for DNA polymerase fidelity. The Journal of biological chemistry, 276, 5044-5051.

Povilaitis, Tadas, et al. "In vitro evolution of phi29 DNA polymerase using isothermal compartmentalized self replication technique." Protein Engineering, Design and Selection 29.12 (2016): 617-628.

Queipo-Ortuno, M.I., De Dios Colmenero, J., Macias, M., Bravo, M.J. and Morata, P. (2008) Preparation of bacterial DNA template by boiling and effect of immunoglobulin G as an inhibitor in real-time PCR for serum samples from patients with brucellosis. Clin Vaccine Immunol, 15, 293-296.

Ramalingam, N., San, T.C., Kai, T.J., Mak, M.Y.M. and Gong, H.-Q. (2009) Microfluidic devices harboring unsealed reactors for real-time isothermal helicase-dependent amplification. Microfluidics and Nanofluidics, 7, 325-336.

Reagin, M.J., Giesler, T.L., Merla, A.L., Resetar-Gerke, J.M., Kapolka, K.M. and Mamone, J.A. (2003) TempliPhi: A sequencing template preparation procedure that eliminates overnight cultures and DNA purification. J Biomol Tech, 14, 143-148.

Rogers, K.; Hobgood, M.; Nance, J.; Cline, D.; Browning, S.; Eason, M.; Eversburg, A.; Lawson, N.; Campbell, L.; Wilhelm, D.; Karpel, R., Structural modeling of Gene 32 protein and SSB's roles in DNA replication, recombination and repair. Faseb Journal 2010, 24.

Roychoudhury, R. and Wu, R. (1977) Novel properties of *Escherichia coli* exonuclease III. The Journal of biological chemistry, 252, 4786-4789.

Sagner, G., Ruger, R. and Kessler, C. (1991) Rapid filter assay for the detection of DNA polymerase activity: direct identification of the gene for the DNA polymerase from Thermus aquaticus. Gene, 97, 119-123.

Sawai, Hiroaki. "Synthesis and properties of oligoadenylic acids containing 2'-5' phosphoramide linkage." Chemistry Letters 13.5 (1984): 805-808.

Schwinefus, J. J.; Engelsgjerd, S.; Mangold, K.; Thompson, P., Urea Induced DNA Denaturation. Biophysical Journal 2013, 104, (2), 425a-425a.

Shlyakhtenko, L. S.; Lushnikov, A. Y.; Miyagi, A.; Lyubchenko, Y. L., Specificity of Binding of Single-Stranded DNA-Binding Protein to Its Target. Biochemistry 2012, 51, (7), 1500-1509.

Singer, A.; Kuhn, H.; Frank-Kamenetskii, M.; Meller, A., Detection of urea-induced internal denaturation of dsDNA using solid-state nanopores. Journal of Physics-Condensed Matter 2010, 22, (45).

Sissi, C.; Palumbo, M., Effects of magnesium and related divalent metal ions in topoisomerase structure and function. Nucleic Acids Research 2009, 37, (3), 702-711.

Song, J. Z.; Mauk, M. G.; Hackett, B. A.; Cherry, S.; Bau, H. H.; Liu, C. C., Instrument-Free Point-of-Care Molecular Detection of Zika Virus. Analytical Chemistry 2016, 88, (14), 7289-7294.

Sprinzl, Mathias, et al. "Enzymatic incorporation of ATP and CTP analogues into the 3' end of tRNA." European journal of biochemistry 81.3 (1977): 579-589.

Stemmer, W.P. (1994) DNA shuffling by random fragmentation and reassembly: in vitro recombination for molecular evolution. Proceedings of the National Academy of Sciences of the United States of America, 91, 10747-10751.

Suwancharoen, D.; Sittiwicheanwong, B.; Wiratsudakul, A., Evaluation of loop-mediated isothermal amplification method (LAMP) for pathogenic *Leptospira* spp. detection with leptospires isolation and real-time PCR. Journal of Veterinary Medical Science 2016, 78, (8), 1299-1302.

Suzuki, M., Baskin, D., Hood, L. and Loeb, L.A. (1996) Random mutagenesis of Thermus aquaticus DNA polymerase I: concordance of immutable sites in vivo with the crystal structure. Proceedings of the National Academy of Sciences of the United States of America, 93, 9670-9675.

Suzuki, R., Ihira, M., Enomoto, Y., Yano, H., Maruyama, F., Emi, N., Asano, Y. and Yoshikawa, T. (2010) Heat denaturation increases the sensitivity of the cytomegalovirus loop-mediated isothermal amplification method. Microbiol Immunol, 54, 466-470.

Tanner, N. A.; Zhang, Y. H.; Evans, T. C., Simultaneous multiple target detection in real-time loop-mediated isothermal amplification. Biotechniques 2012, 53, (2), 81-+.

(56) References Cited

OTHER PUBLICATIONS

Tomita, N.; Mori, Y.; Kanda, H.; Notomi, T., Loop-mediated isothermal amplification (LAMP) of gene sequences and simple visual detection of products. Nature Protocols 2008, 3, (5), 877-882.
Verkooyen, R.P., Luijendijk, A., Huisman, W.M., Goessens, W.H., Kluytmans, J.A., van Rijsoort-Vos, J.H. and Verbrugh, H.A. (1996) Detection of PCR inhibitors in cervical specimens by using the AMPLICOR Chlamydia trachomatis assay. Journal of clinical microbiology, 34, 3072-3074.
Vichier-Guerre, S., Ferris, S., Auberger, N., Mahiddine, K. and Jestin, J.L. (2006) A population of thermostable reverse transcriptases evolved from Thermus aquaticus DNA polymerase I by phage display. Angewandte Chemie, 45, 6133-6137.
Wang, Y.; Li, D. X.; Wang, Y.; Li, K. W.; Ye, C. Y., Rapid and Sensitive Detection of Vibrio parahaemolyticus and Vibrio vulnificus by Multiple Endonuclease Restriction Real-Time Loop-Mediated Isothermal Amplification Technique. Molecules 2016, 21, (1).
Wu, Q., Jin, W., Zhou, C., Han, S., Yang, W., Zhu, Q., Jin, Q. and Mu, Y. (2011) Integrated glass microdevice for nucleic acid purification, loop-mediated isothermal amplification, and online detection. Analytical chemistry, 83, 3336-3342.
Horn, T., Chaturvedi, S., Balasubramaniam, T. N., & Letsinger, R. L. (1996). Oligonucleotides with alternating anionic and cationic phosphoramidate linkages: Synthesis and hybridization of stereouniform isomers. Tetrahedron letters, 37(6), 743-746.
Ye, S.Y. and Hong, G.F. (1987) Heat-stable DNA polymerase I large fragment resolves hairpin structure in DNA sequencing. Sci Sin B, 30, 503-506.
Zahran, M.; Berezniak, T.; Imhof, P.; Smith, J. C., Role of magnesium ions in DNA recognition by the EcoRV restriction endonuclease. Febs Letters 2011, 585, (17), 2739-2743.
Zhang, B., Wang, Q., & Pan, X. (2007). MicroRNAs and their regulatory roles in animals and plants. Journal of cellular physiology, 210(2), 279-289.
Zhang, C., Yao, Y., Zhu, J. L., Zhang, S. N., Zhang, S. S., Wei, H., . . . & Cui, Y. L. (2016). Establishment and application of a real-time loop-mediated isothermal amplification system for the detection of CYP2C19 polymorphisms. Scientific reports, 6(1), 1-7.
Zhang, D.Y., Zhang, W., Li, X. and Konomi, Y. (2001) Detection of rare DNA targets by isothermal ramification amplification. Gene, 274, 209-216.
Zhang, K., Martiny, A.C., Reppas, N.B., Barry, K.W., Malek, J., Chisholm, S.W. and Church, G.M. (2006) Sequencing genomes from single cells by polymerase cloning. Nature biotechnology, 24, 680-686.
Zhao, Y., Chen, F., Li, Q., Wang, L. and Fan, C. (2015) Isothermal Amplification of Nucleic Acids. Chemical reviews, 115, 12491-12545.
Zhu, Z. Y.; Ravelet, C.; Perrier, S.; Guieu, V.; Fiore, E.; Peyrin, E., Single-Stranded DNA Binding Protein-Assisted Fluorescence Polarization Aptamer Assay for Detection of Small Molecules. Analytical Chemistry 2012, 84, (16), 7203-7211.
International Preliminary Report on Patentability issued for Application No. PCT/US2018/032074, dated Nov. 21, 2019.
International Search Report and Written Opinion dated Aug. 10, 2018, from International Application No. PCT/US2018/032074, 18 pages.
Pavlov et al. "Cooperation between Catalytic and DNA-binding Domains Enhances Thermostability and Supports DNA Synthesis at Higher Temperatures by Thermostable DNA Polymerases", Biochemistry. Mar. 13, 2012; 51(10): 2032-2043.
Ott et al. "Protection of Oligonucleotide Primers against Degradation by DNA Polymerase I", Biochemistry 1987, 26, 8237-8241.
Yaren et al. "Point of sampling detection of Zika virus within a multiplexed kit capable of detecting dengue and chikungunya", BMC Infectious Diseases (2017) 17:293, 12 pages.

\* cited by examiner

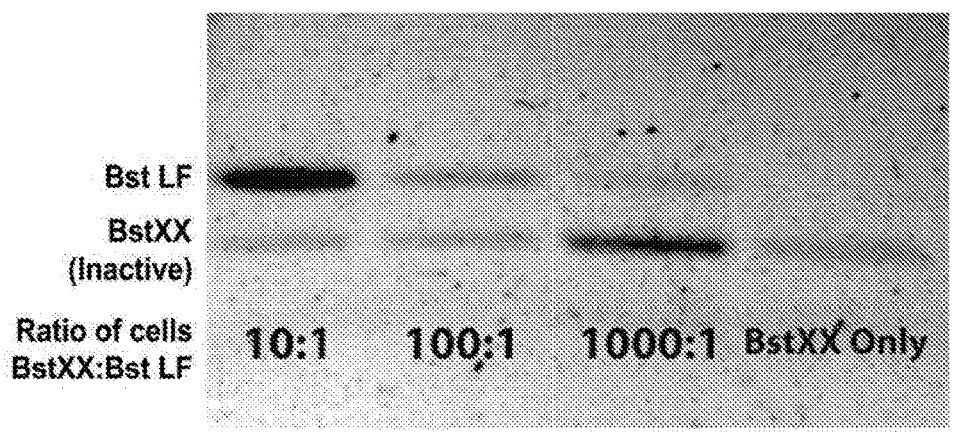
FIG. 2
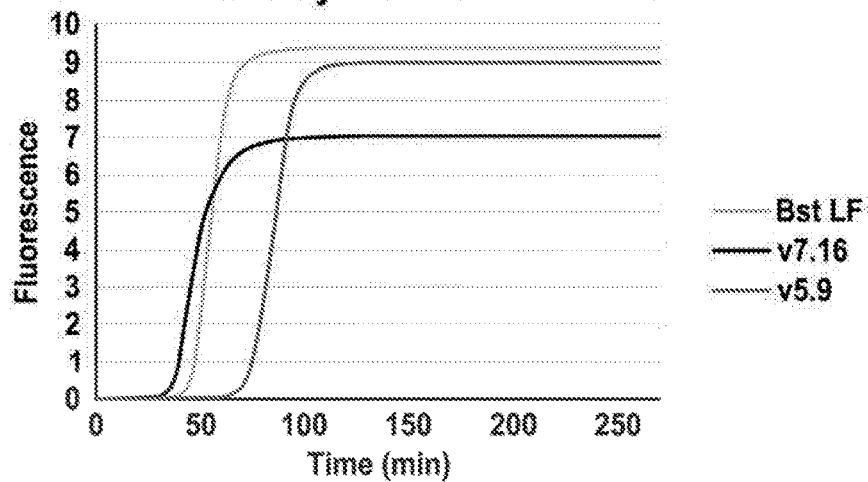
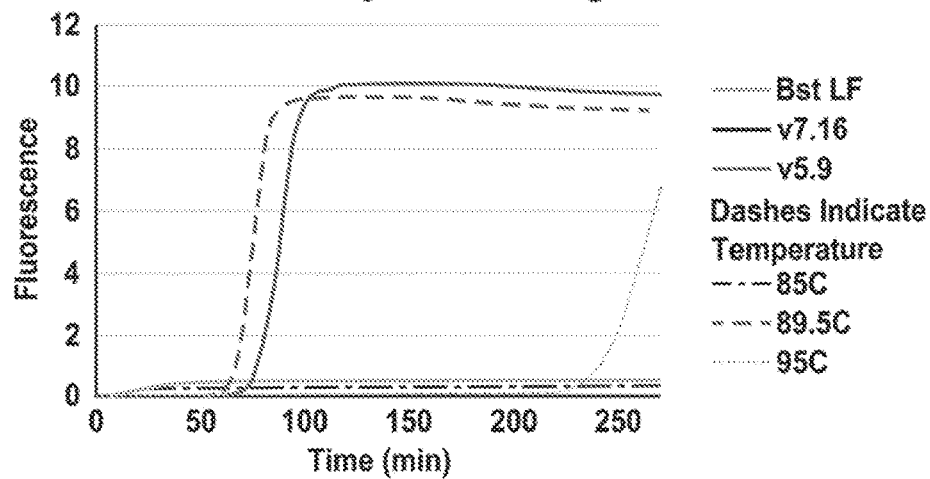
FIG. 3

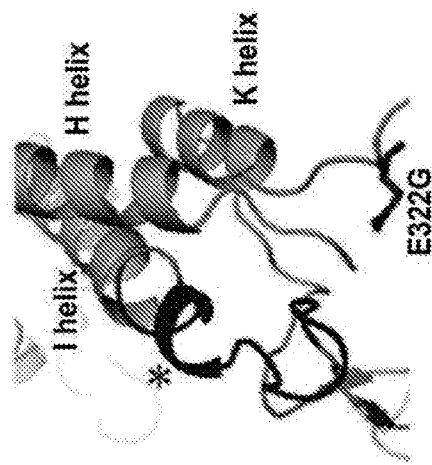
C. Klentaq Thumb Base with Crossover Region and 5.9 point mutation
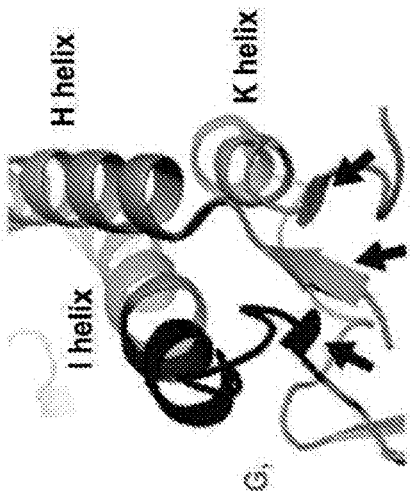
D. Bst LF Thumb Base with Crossover Region
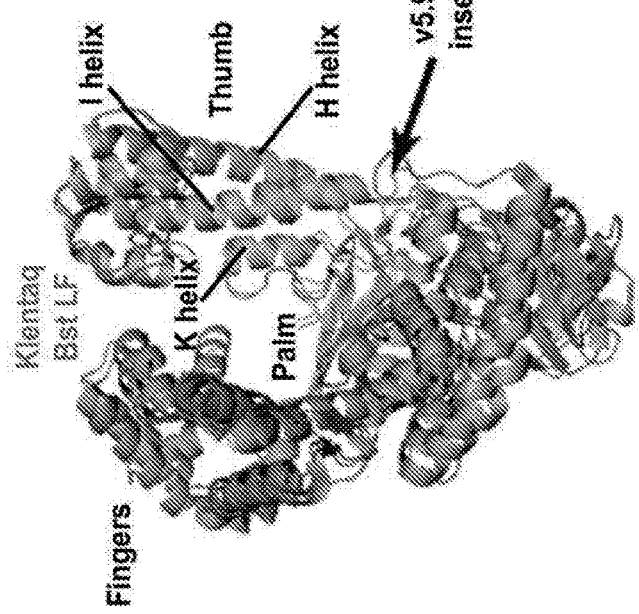
A. Alignment of Bst LF and Klentaq
B. Sequence Characteristics of v5.9
Primary Sequence: Klentaq
Mutations: Bst insertion (D283E, P284G, P286L, D287K, L288V, I289V, H290R, R292D, G294K, R295K, L296V), E322G, L484S
FIG. 6

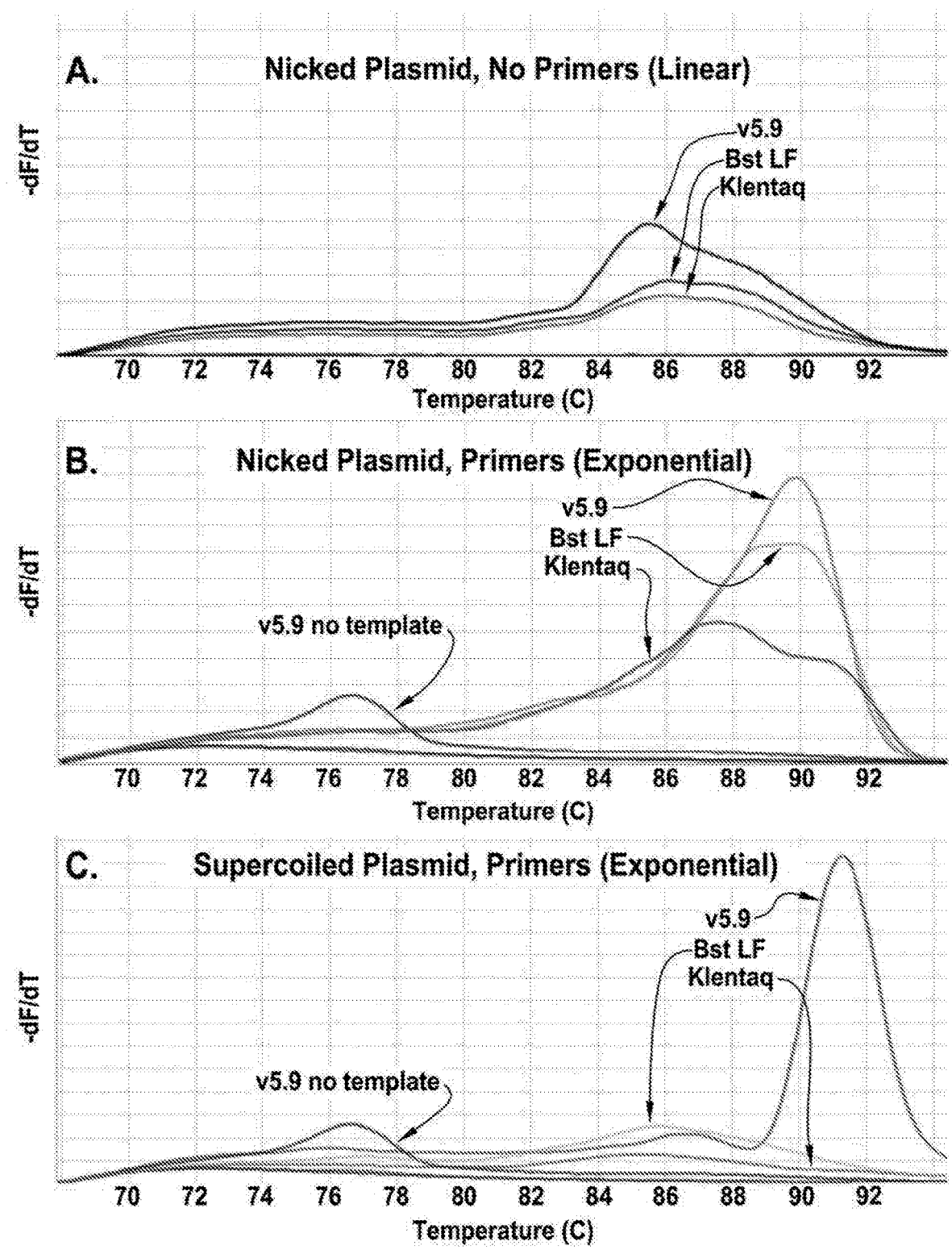
FIGS. 13A-C

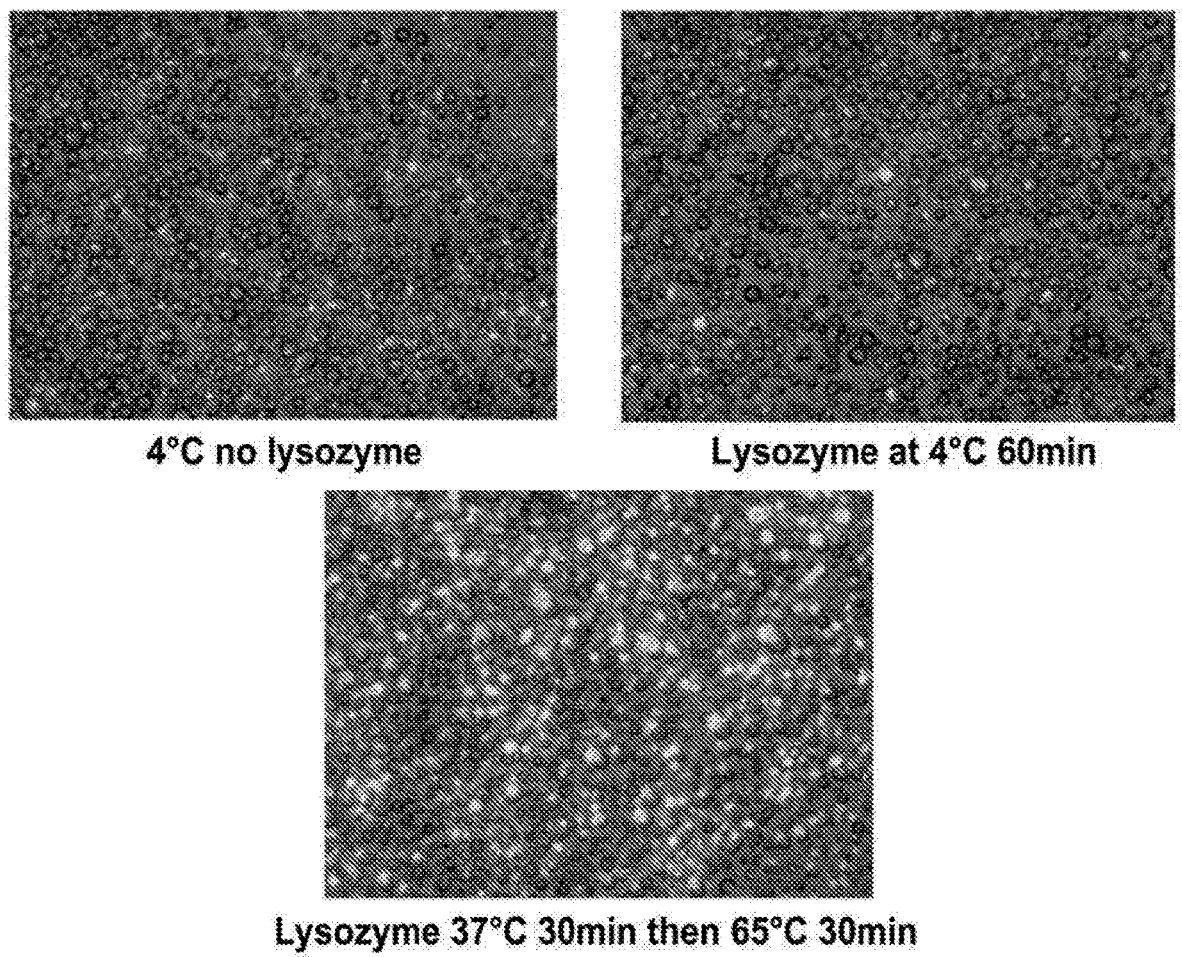
FIGS. 14A-C
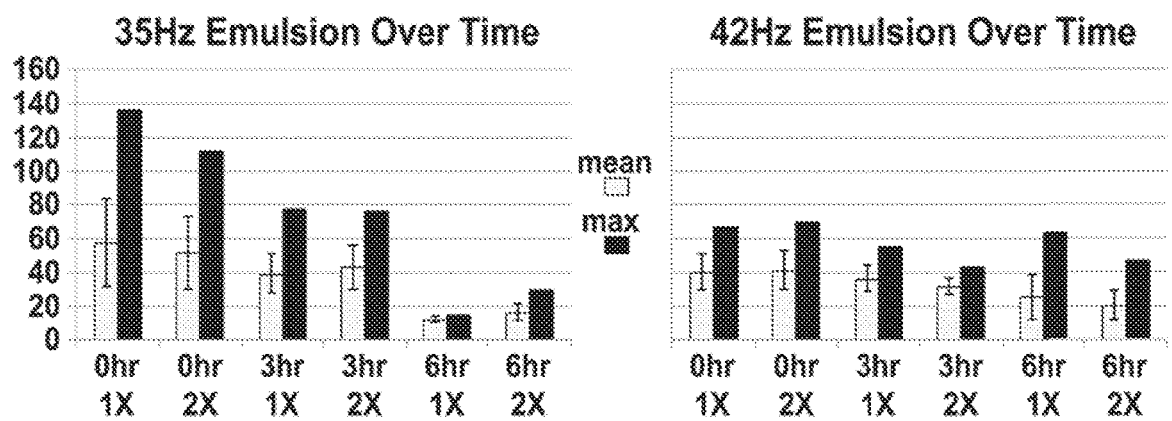
FIG. 15

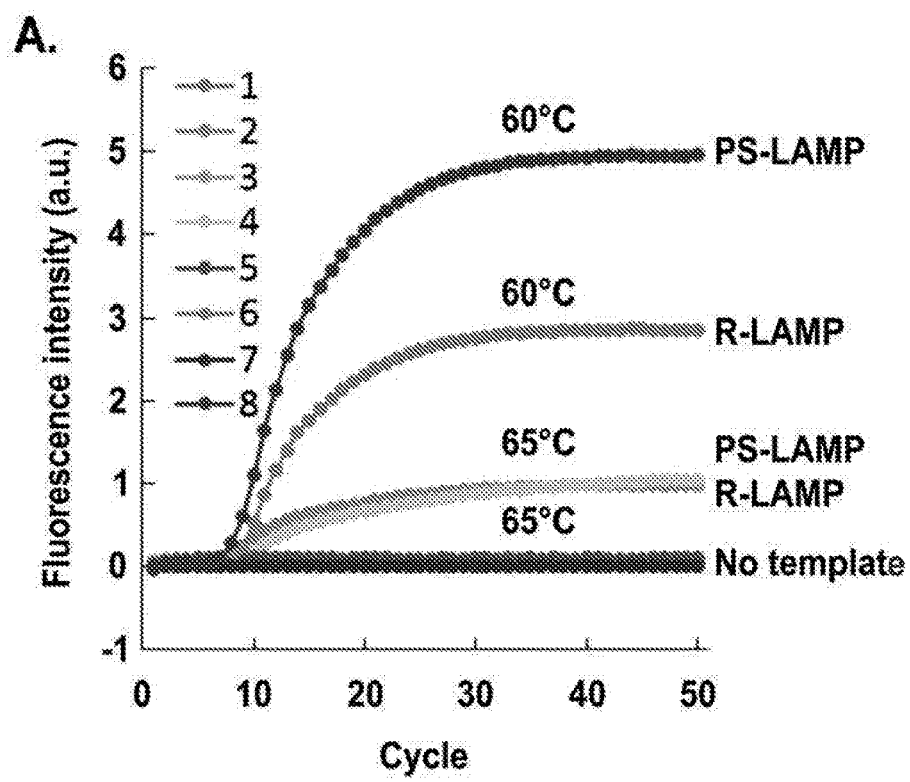
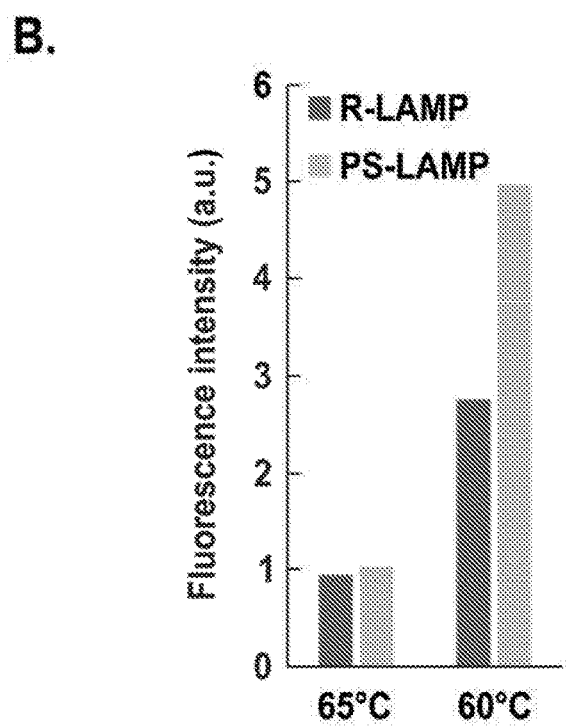
FIG. 17 A-C

C.
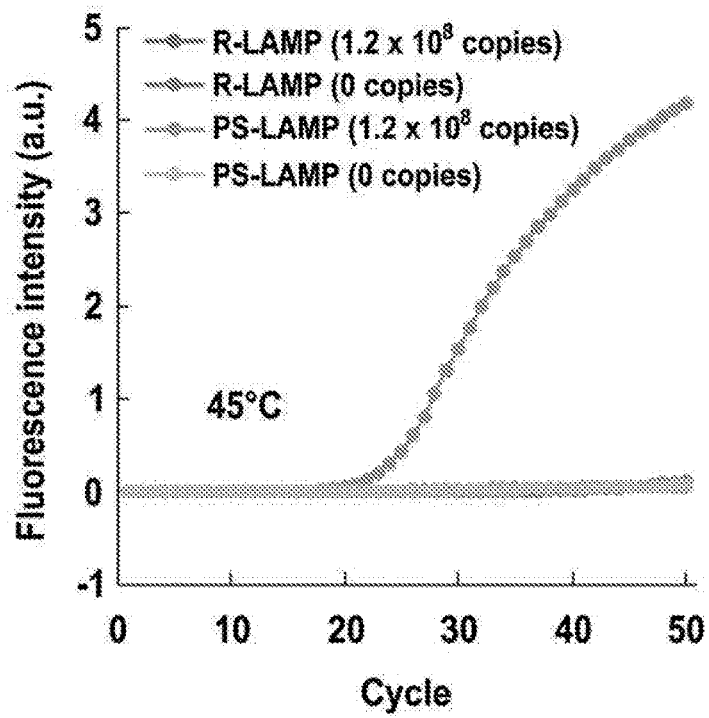
FIG 17. A-C Cont.
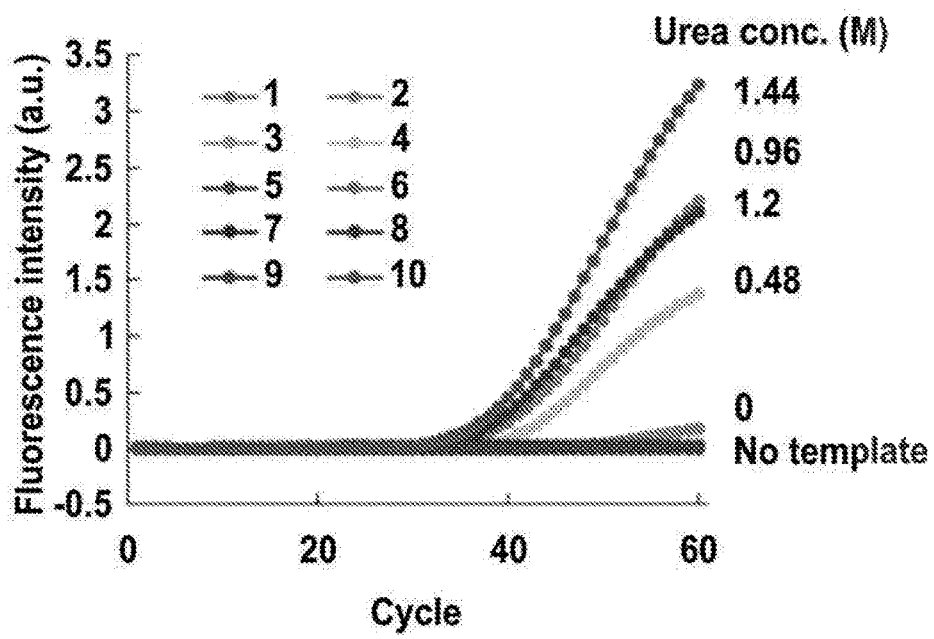
FIG. 18 A-D

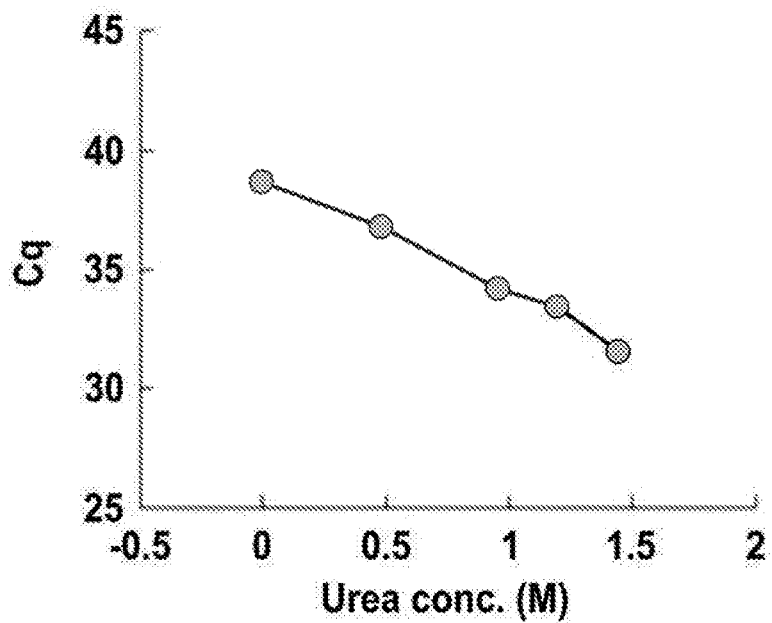
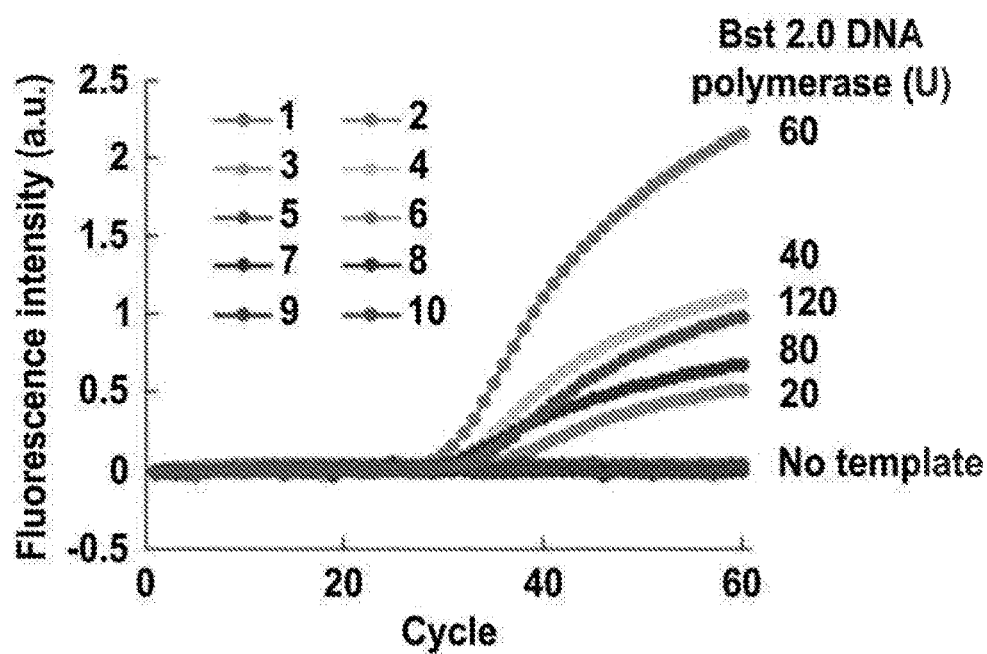
FIG 18. A-D Cont.

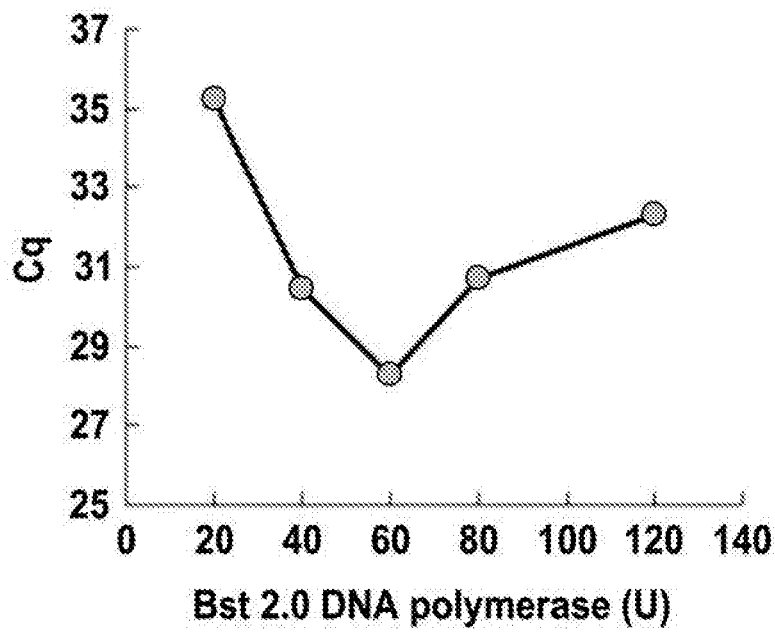
FIG. 18 A-D Cont.
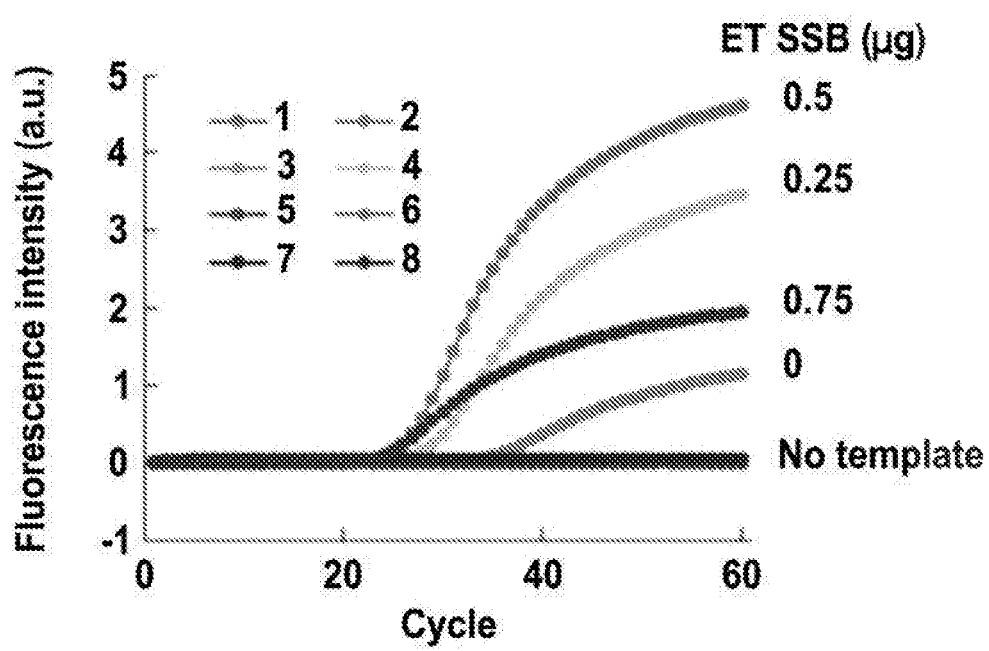
FIG. 19 A-D

B.
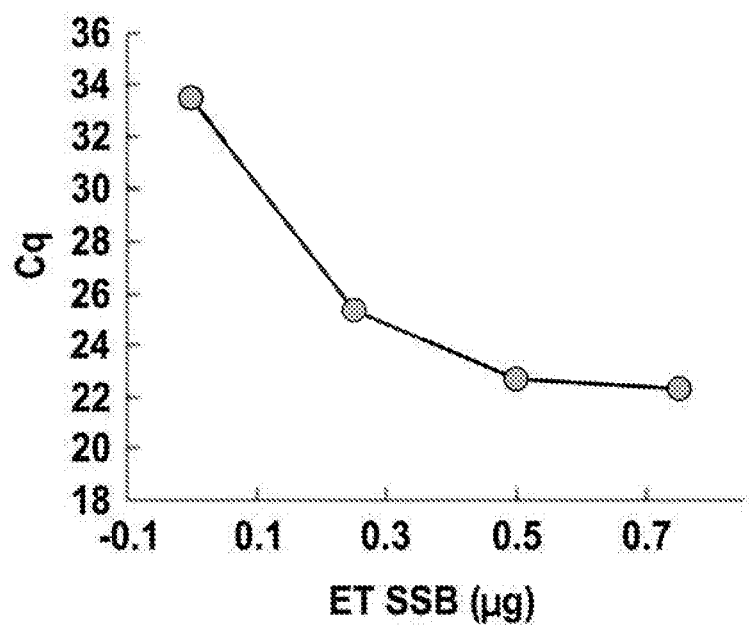
C.
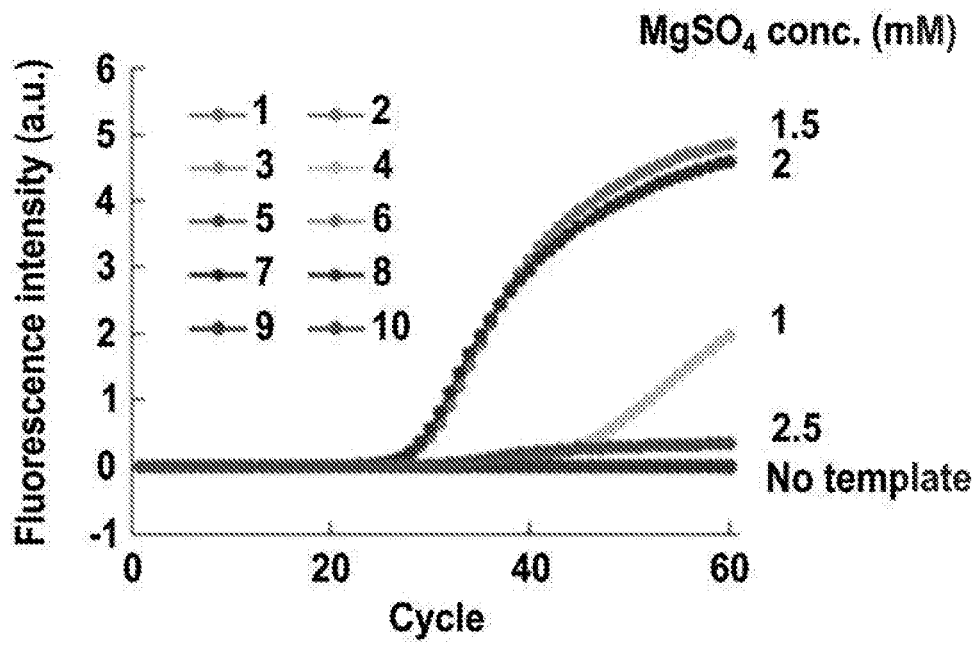
FIG 19. A-D Cont.

D.
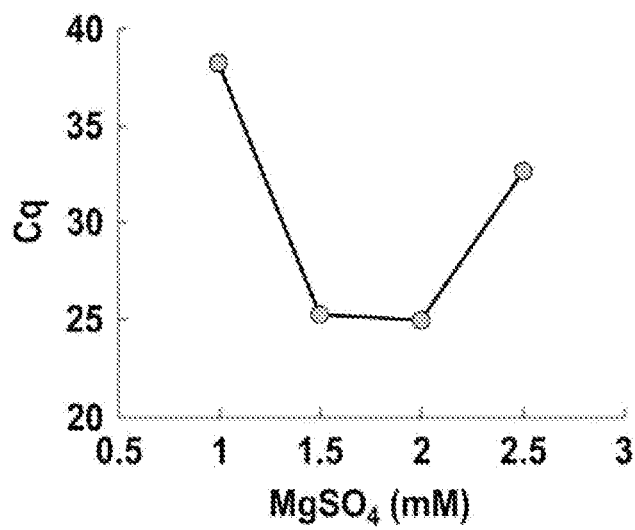
FIG 19. A-D Cont.
A.
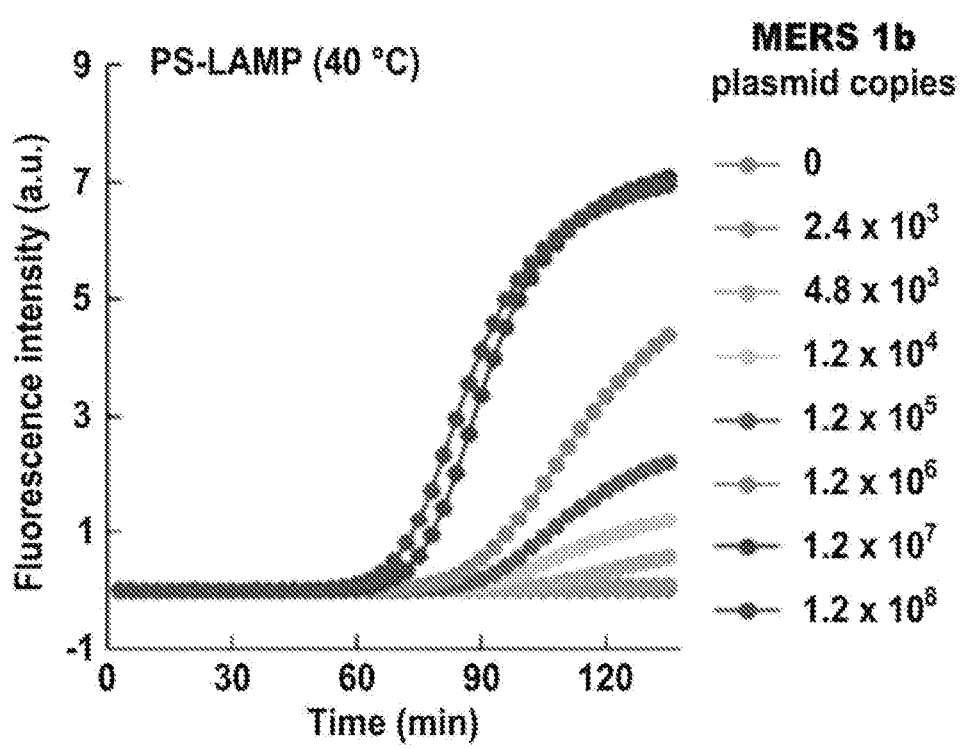
FIG. 20 A-D

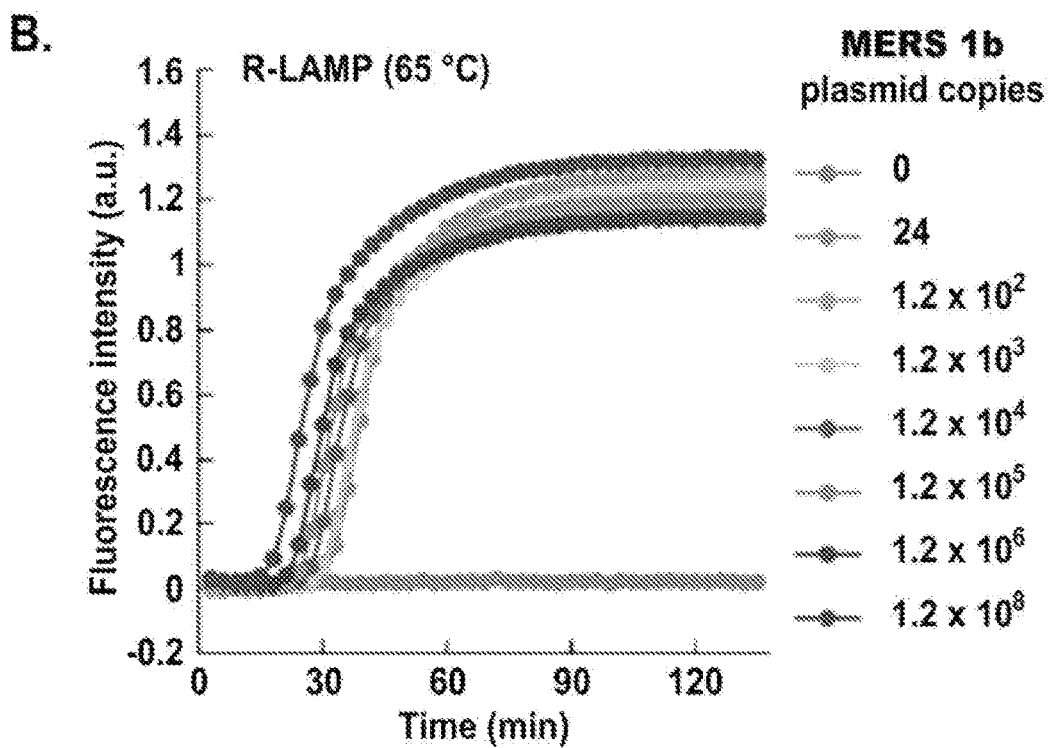
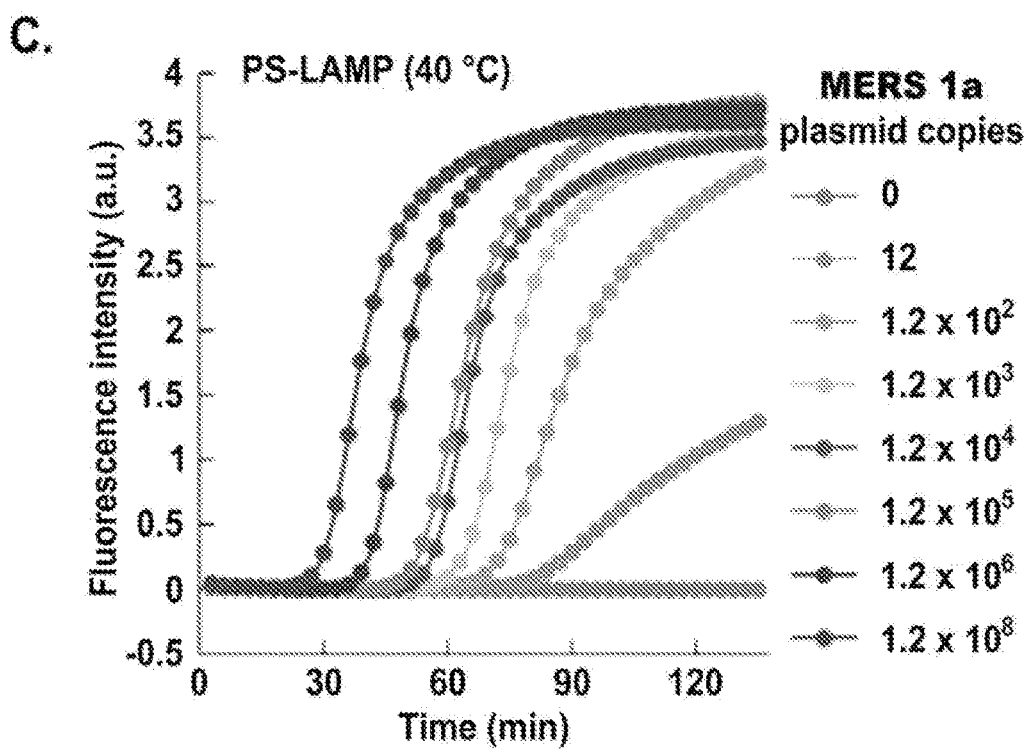
FIG. 20 A-D Cont.

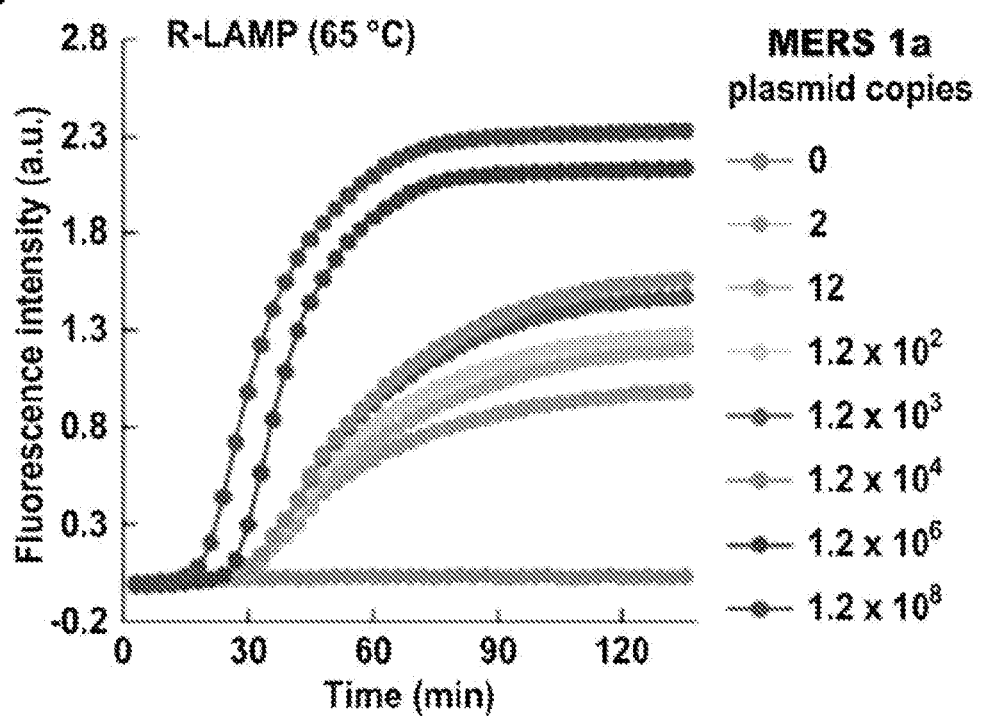
FIG. 20 A-D Cont.

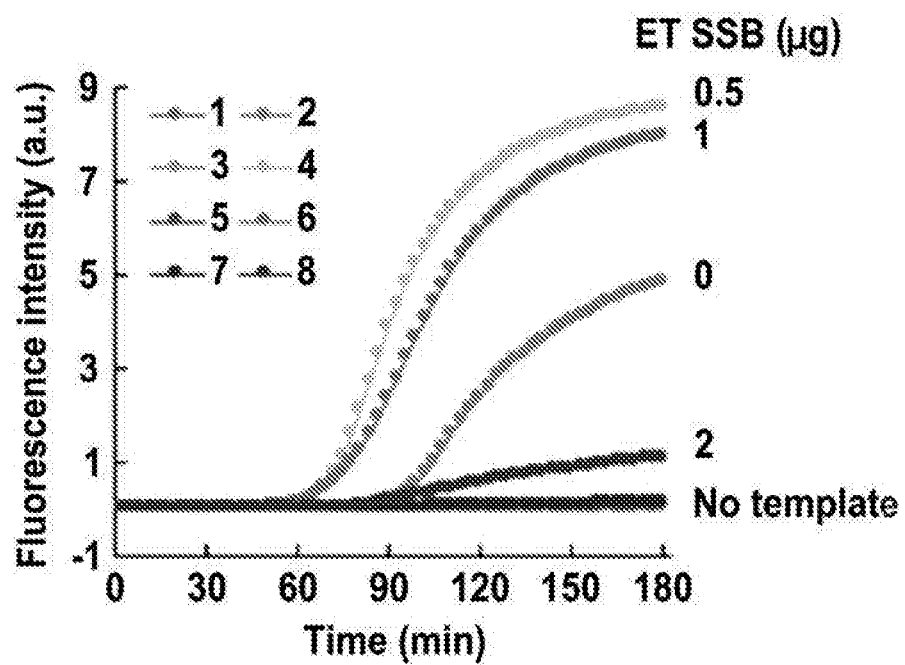
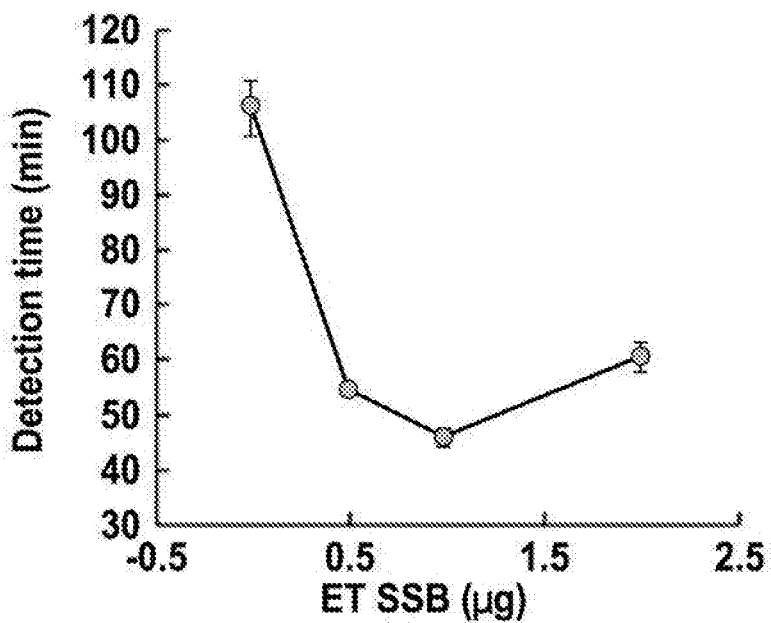
FIG. 22 A-F

C.
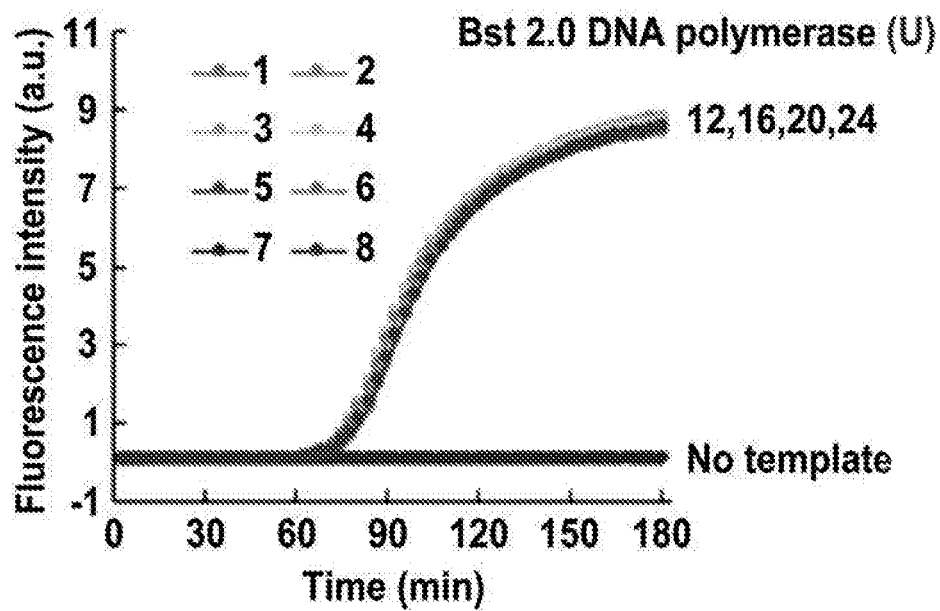
D.
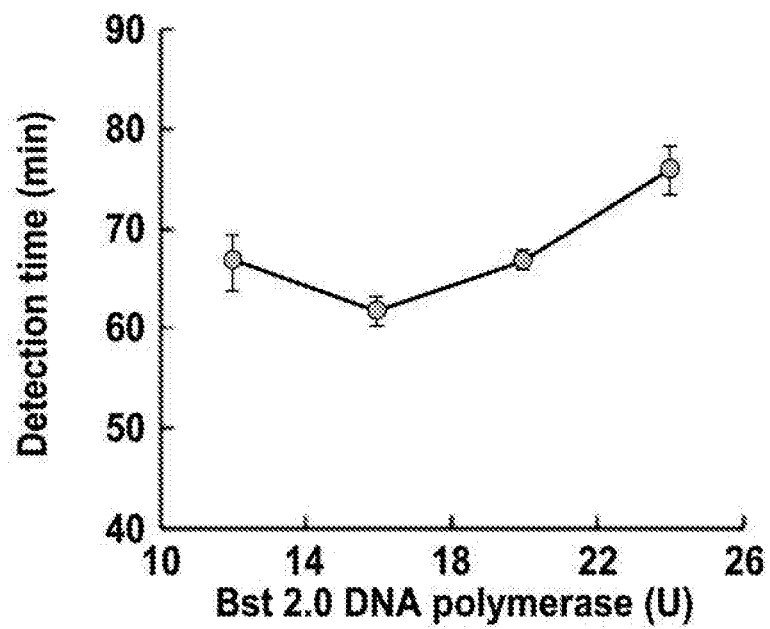
FIG. 22 A-F Cont.

E.
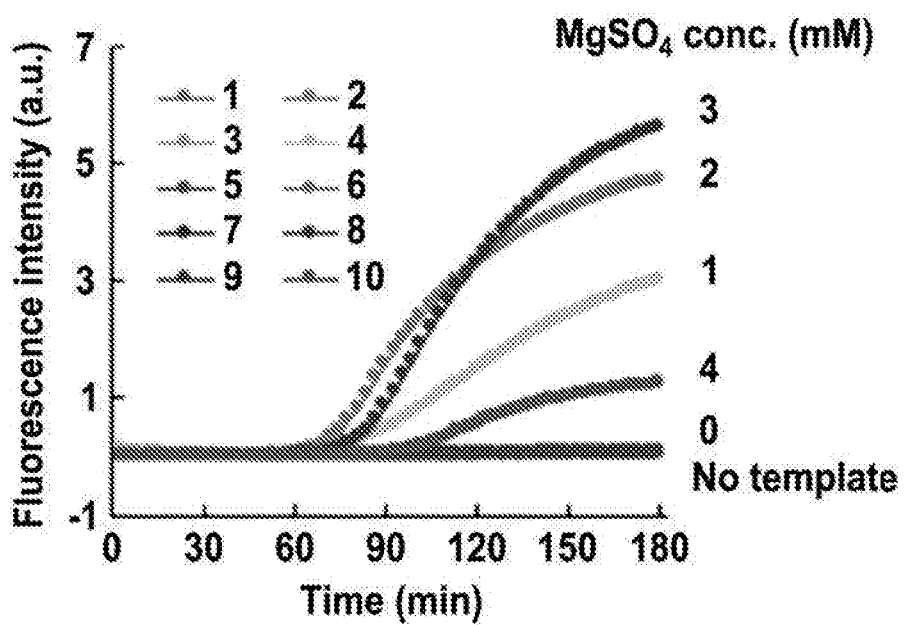
F.
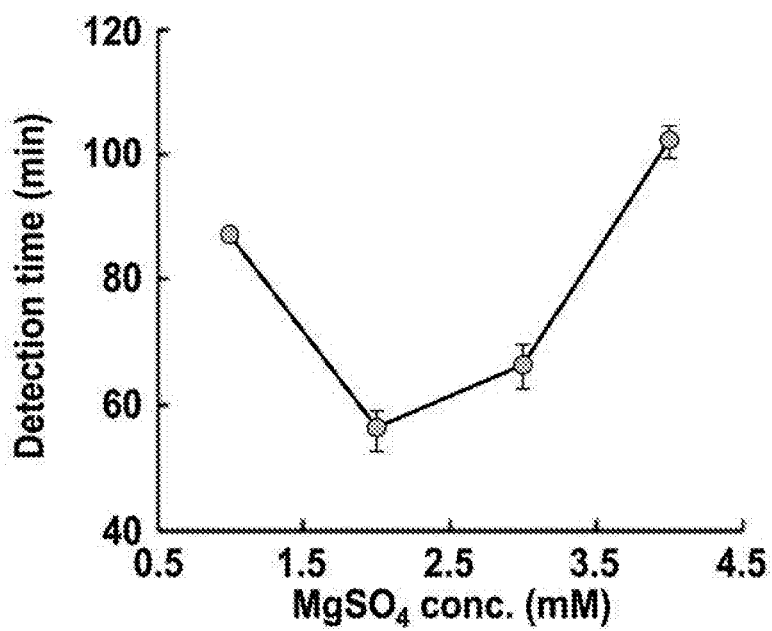
FIG. 22 A-F Cont.

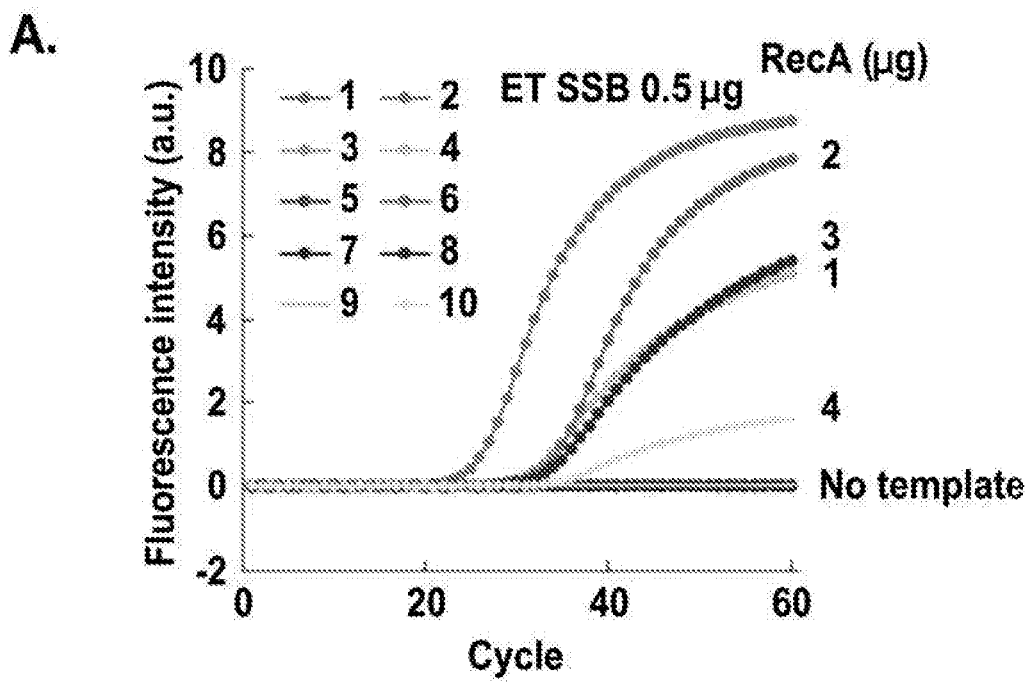
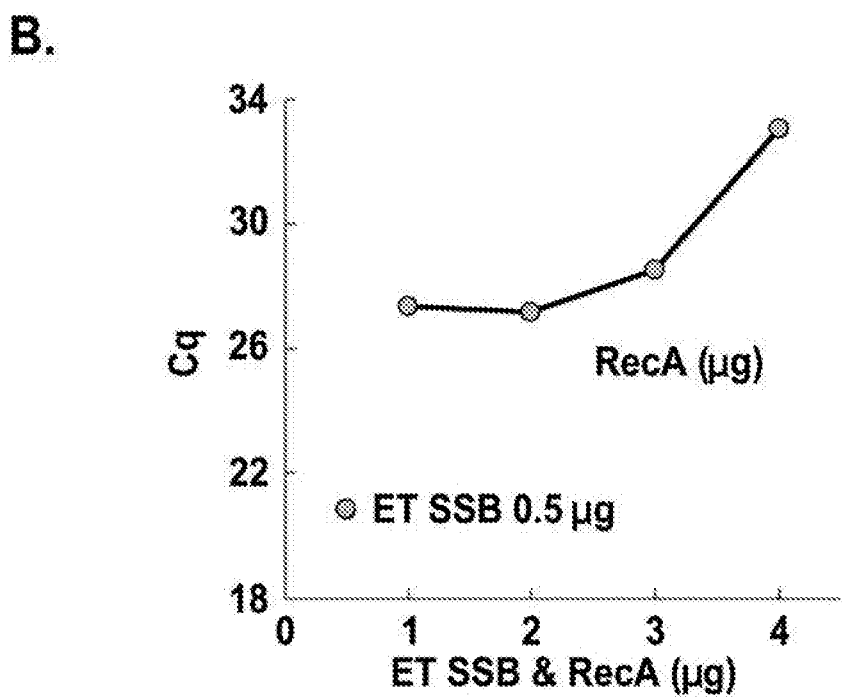
FIG. 23 A-B

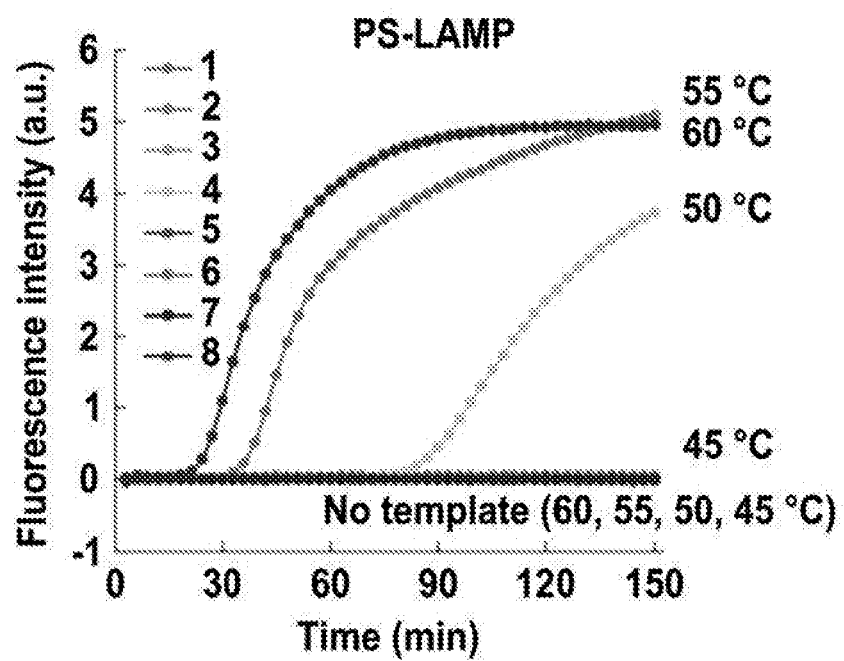
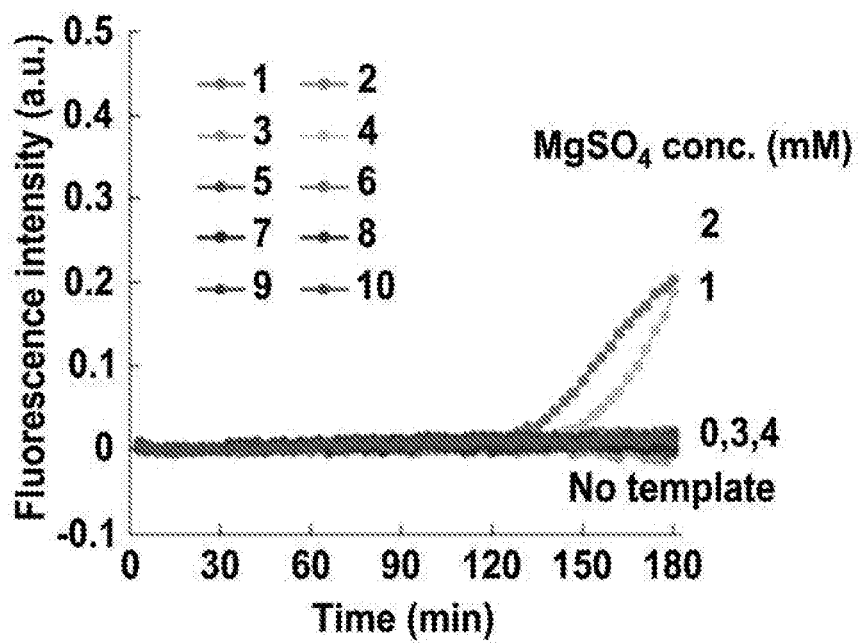
FIG. 24 A-B

| Number | 1 | 2 |
|---|---|---|
| NS5 Template (2 µl) | 2.5fg/µl | 2.5fg/µl |
| primers mix | 2µl | 2µl |
| dNTPs (4 mM) | 2.5µl | 2.5µl |
| 10x Isothermal buffer | 2.5µl | 2.5µl |
| Betaine (5M) | 5µl | 5µl |
| RTX (15U/µl) | 1.5µl (warm) | 1.5µl (non-warm) |
| Bst 2.0 (120 U/µl) | 0.5µl | 0.5µl |
| SSB (0.5 µg/µl) | 1µl | 1µl |
| OSD (1µM) | 2.5µl | 2.5µl |
| Urea (12M) | 3µl | 3µl |
| Water | 2.5µl | 2.5µl |
| Total | 25µl | 25µl |

| Number | 1 | 2 |
|---|---|---|
| NS5 Template (2 μl) | 2.5 fg/μl | 2.5 fg/μl |
| primers mix | 2 μl | 2 μl |
| nNTPs (4 mM) | 2.5 μl | 2.5 μl |
| 10x Isothermal buffer | 2.5 μl | 2.5 μl |
| Betaine (5M) | 5 μl | 5 μl |
| RTX (15U/μl) | 1.5 μl (warm) | 1.5 μl (warm) |
| Bst 2.0 (120 U/μl) | 0.5 μl | 0.5 μl |
| SSB (0.5 μg/μl) | 1 μl | 1 μl |
| OSD (1 μM) | 2.5 μl | 2.5 μl |
| Urea (12M) | 3 μl | 3 μl |
| Water | 2.5 μl | 2.5 μl |
| Total | 25 μl | 25 μl |

| Number | 1 | 2 | 3 | 4 | 5 | 6 | 7 | 8 (control) |
|---|---|---|---|---|---|---|---|---|
| NS5 Template(25 fg/µl) | 2 µl | 2 µl | 2 µl | 2 µl | 2 µl | 2 µl | 0 µl | 0 µl |
| primers mix | 2 µl | 2 µl | 2 µl | 2 µl | 2 µl | 2 µl | 2 µl | 2 µl |
| dNTPs (4 mM) | 2.5 µl | 2.5 µl | 2.5 µl | 2.5 µl | 2.5 µl | 2.5 µl | 2.5 µl | 2.5 µl |
| 10x Isothermal buffer | 2.5 µl | 2.5 µl | 2.5 µl | 2.5 µl | 2.5 µl | 2.5 µl | 2.5 µl | 2.5 µl |
| Betaine (5M) | 5 µl | 5 µl | 5 µl | 5 µl | 5 µl | 5 µl | 5 µl | 5 µl |
| Non warm start RTX (15U/µl) | 1.5 µl | 1.5 µl | 1.5 µl | 1.5 µl | 1.5 µl | 1.5 µl | 1.5 µl | 1.5 µl |
| Bst 2.0 (120 U/µl) | 0.5 µl | 0.5 µl | 0.5 µl | 0.5 µl | 0.5 µl | 0.5 µl | 0.5 µl | 0.5 µl |
| SSB (0.5 µg/µl) | 1 µl | 1 µl | 1 µl | 1 µl | 1 µl | 1 µl | 1 µl | 1 µl |
| OSD(1 µM) | 2.5 µl | 2.5 µl | 2.5 µl | 2.5 µl | 2.5 µl | 2.5 µl | 2.5 µl | 2.5 µl |
| Formamide | 3 µl (Urea) | 1.5 µl | 2 µl | 2.5 µl | 3 µl | 3.5 µl | 4 µl | 1.5 µl |
| Water | 2.5 µl | 4 µl | 3.5 µl | 3 µl | 2.5 µl | 2 µl | 1.5 µl | 4 µl |
| Total | 25 µl | 25 µl | 25 µl | 25 µl | 25 µl | 25 µl | 25 µl | 25 µl |

FIG. 26C

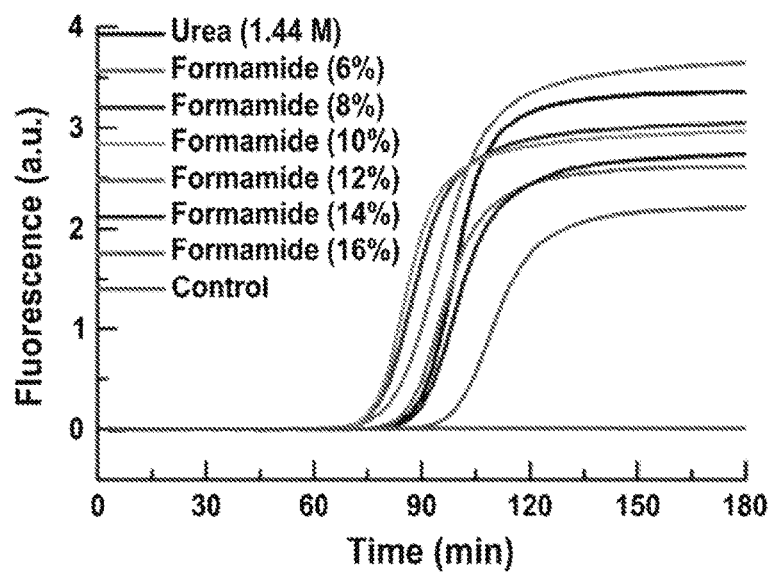

FIG. 26D

| Number | 1 | 2 | 3 | 4 | 5 | 6 | 7 | 8 (control) |
|---|---|---|---|---|---|---|---|---|
| Template (25 fg/µl) | 2 µl | 2 µl | 2 µl | 2 µl | 2 µl | 2 µl | 0 µl | 0 µl |
| primers mix | 2 µl | 2 µl | 2 µl | 2 µl | 2 µl | 2 µl | 2 µl | 2 µl |
| dNTPs (4 mM) | 2.5 µl | 2.5 µl | 2.5 µl | 2.5 µl | 2.5 µl | 2.5 µl | 2.5 µl | 2.5 µl |
| 10x Isothermal buffer | 2.5 µl | 2.5 µl | 2.5 µl | 2.5 µl | 2.5 µl | 2.5 µl | 2.5 µl | 2.5 µl |
| Betaine (5M) | 5 µl | 5 µl | 5 µl | 5 µl | 5 µl | 5 µl | 5 µl | 5 µl |
| Non warm start RTX (15U/µl) | 1.5 µl | 1.5 µl | 1.5 µl | 1.5 µl | 1.5 µl | 1.5 µl | 1.5 µl | 1.5 µl |
| Bst 2.0 (120 U/µl) | 0.5 µl | 0.5 µl | 0.5 µl | 0.5 µl | 0.5 µl | 0.5 µl | 0.5 µl | 0.5 µl |
| SSB (0.5 µg/µl) | 1 µl | 1 µl | 1 µl | 1 µl | 1 µl | 1 µl | 1 µl | 1 µl |
| OSD (1µM) | 2.5 µl | 2.5 µl | 2.5 µl | 2.5 µl | 2.5 µl | 2.5 µl | 2.5 µl | 2.5 µl |
| Formamide | 3 µl (Urea) | 1.5 µl | 2 µl | 3 µl | 3 µl | 3.5 µl | 4 µl | 1.5 µl |
| Water | 2.5 µl | 4 µl | 3.5 µl | 3 µl | 2.5 µl | 2 µl | 1.5 µl | 4 µl |
| Total | 25 µl | 25 µl | 25 µl | 25 µl | 25 µl | 25 µl | 25 µl | 25 µl |

FIG. 26C

| Number | 1 | 2 | 3 | 4 | 5 | 6 (control) |
|---|---|---|---|---|---|---|
| Template (2 µl) | 250 fg/µl | 25 fg/µl | 2.5 fg/µl | 0.25 fg/µl | 0.025 fg/µl | 0 µl |
| primers mix | 2 µl | 2 µl | 2 µl | 2 µl | 2 µl | 2 µl |
| dNTPs (4 mM) | 2.5 µl | 2.5 µl | 2.5 µl | 2.5 µl | 2.5 µl | 2.5 µl |
| 10x Isothermal buffer | 2.5 µl | 2.5 µl | 2.5 µl | 2.5 µl | 2.5 µl | 2.5 µl |
| Betaine (5M) | 5 µl | 5 µl | 5 µl | 5 µl | 5 µl | 5 µl |
| Non warm start RTX (15U/µl) | 1.5 µl | 1.5 µl | 1.5 µl | 1.5 µl | 1.5 µl | 1.5 µl |
| Bst 2.0 (120 U/µl) | 0.5 µl | 0.5 µl | 0.5 µl | 0.5 µl | 0.5 µl | 0.5 µl |
| SSB (0.5 µg/µl) | 1 µl | 1 µl | 1 µl | 1 µl | 1 µl | 1 µl |
| OSD (1µM) | 2.5 µl | 2.5 µl | 2.5 µl | 2.5 µl | 2.5 µl | 2.5 µl |
| Formamide | 2 µl | 2 µl | 2 µl | 2 µl | 2 µl | 2 µl |
| Water | 3.5 µl | 3.5 µl | 3.5 µl | 3.5 µl | 3.5 µl | 5.5 µl |
| Total | 25 µl | 25 µl | 25 µl | 25 µl | 25 µl | 25 µl |

Do denaturation at 65C, 5min, then transfer samples on ice, keep for 2 min. (columns 2–5)

FIG. 27A

SEQUENCE LISTING

<160> NUMBER OF SEQ ID NOS: 68

<210> SEQ ID NO 1
<211> LENGTH: 568
<212> TYPE: PRT
<213> ORGANISM: Artificial Sequence
<220> FEATURE:
<223> OTHER INFORMATION: Synthetic Construct

<400> SEQUENCE: 1

```
Met Ala Ser Arg Gly Ser His His His His His His Ile Glu Gly Arg
1               5                   10                  15

Leu Leu His Glu Phe Gly Leu Leu Glu Ser Pro Lys Ala Leu Glu Glu
            20                  25                  30

Ala Pro Trp Pro Pro Glu Gly Ala Phe Val Gly Phe Val Leu Ser
        35                  40                  45

Arg Lys Glu Pro Met Trp Ala Asp Leu Leu Ala Leu Ala Ala Ala Arg
    50                  55                  60

Gly Gly Arg Val His Arg Ala Pro Glu Pro Tyr Lys Ala Leu Arg Asp
65                  70                  75                  80

Leu Lys Glu Ala Arg Gly Leu Leu Ala Lys Asp Leu Ser Val Leu Ala
                85                  90                  95

Leu Arg Glu Gly Leu Gly Leu Pro Pro Gly Asp Asp Pro Met Leu Leu
            100                 105                 110

Ala Tyr Leu Leu Asp Pro Ser Asn Thr Thr Pro Glu Gly Val Ala Arg
        115                 120                 125

Arg Tyr Gly Gly Glu Trp Thr Glu Glu Ala Gly Glu Arg Ala Ala Leu
    130                 135                 140

Ser Glu Arg Leu Phe Ala Asn Leu Trp Gly Arg Leu Glu Gly Glu Glu
145                 150                 155                 160

Arg Leu Leu Trp Leu Tyr Arg Glu Val Glu Arg Pro Leu Ser Ala Val
                165                 170                 175

Leu Ala His Met Glu Ala Thr Gly Val Arg Leu Asp Val Ala Tyr Leu
            180                 185                 190

Arg Ala Leu Ser Leu Glu Val Ala Glu Glu Ile Ala Arg Leu Glu Ala
        195                 200                 205

Glu Val Phe Arg Leu Ala Gly His Pro Phe Asn Leu Asn Ser Arg Asp
    210                 215                 220

Gln Leu Glu Arg Val Leu Phe Asp Glu Leu Gly Leu Pro Ala Ile Gly
225                 230                 235                 240

Lys Thr Glu Lys Thr Gly Lys Arg Ser Thr Ser Ala Ala Val Leu Glu
                245                 250                 255

Ala Leu Arg Glu Ala His Pro Ile Val Glu Lys Ile Leu Gln Tyr Arg
            260                 265                 270

Glu Leu Thr Lys Leu Lys Ser Thr Tyr Ile Glu Gly Leu Leu Lys Val
        275                 280                 285

Val Arg Pro Asp Thr Lys Lys Val His Thr Arg Phe Asn Gln Thr Ala
```

```
                        290                 295                 300
Thr Ala Thr Gly Arg Leu Ser Ser Asp Pro Asn Leu Gln Asn Ile
305                 310                 315                 320
Pro Val Arg Thr Pro Leu Gly Gln Arg Ile Arg Arg Ala Phe Ile Ala
                325                 330                 335
Gly Glu Gly Trp Leu Leu Val Ala Leu Asp Tyr Ser Gln Ile Glu Leu
            340                 345                 350
Arg Val Leu Ala His Leu Ser Gly Asp Glu Asn Leu Ile Arg Val Phe
        355                 360                 365
Gln Glu Gly Arg Asp Ile His Thr Glu Thr Ala Ser Trp Met Phe Gly
    370                 375                 380
Val Pro Arg Glu Ala Val Asp Pro Leu Met Arg Arg Ala Ala Lys Thr
385                 390                 395                 400
Ile Asn Phe Gly Val Leu Tyr Gly Met Ser Ala His Arg Leu Ser Gln
                405                 410                 415
Glu Leu Ala Ile Pro Tyr Glu Glu Ala Gln Ala Phe Ile Glu Arg Tyr
            420                 425                 430
Phe Gln Ser Phe Pro Lys Val Arg Ala Trp Ile Glu Lys Thr Leu Glu
        435                 440                 445
Glu Gly Arg Arg Arg Gly Tyr Val Glu Thr Leu Phe Gly Arg Arg Arg
    450                 455                 460
Tyr Val Pro Asp Leu Glu Ala Arg Val Lys Ser Val Arg Glu Ala Ala
465                 470                 475                 480
Glu Arg Met Ala Phe Asn Met Pro Val Gln Gly Thr Ala Ala Asp Leu
                485                 490                 495
Met Lys Ser Ala Met Val Lys Leu Phe Pro Arg Leu Glu Glu Met Gly
            500                 505                 510
Ala Arg Met Leu Leu Gln Val His Asp Glu Leu Val Leu Glu Ala Pro
        515                 520                 525
Lys Glu Arg Ala Glu Ala Val Ala Arg Leu Ala Lys Glu Val Met Glu
    530                 535                 540
Gly Val Tyr Pro Leu Ala Val Pro Leu Glu Val Glu Val Gly Ile Gly
545                 550                 555                 560
Glu Asp Trp Leu Ser Ala Lys Glu
                565

<210> SEQ ID NO 2
<211> LENGTH: 1704
<212> TYPE: DNA
<213> ORGANISM: Artificial Sequence
<220> FEATURE:
<223> OTHER INFORMATION: Synthetic Construct

<400> SEQUENCE: 2
atggcgagcc gcggcagcca tcatcatcat catcatattg aaggccgcct gctgcatgaa      60
tttggcctgc tggaaagccc gaaagcgctg gaagaagcgc gtggccgcc gccgaaggc      120 gcgtttgtgg gctttgtgct gagccgcaaa gaaccgatgt gggcggatct gctggcgctg      180
gcggcggcgc gcggcggccg cgtgcatcgc gcgccggaac gtataaaagc gctgcgcgat      240
ctgaaagaag cgcgcggcct gctggcgaaa gatctgagcg tgctggcgct gcgcgaaggc      300
ctgggcctgc cgccgggcga tgatccgatg ctgctggcgt atctgctgga tccgagcaac      360
accaccccgg aaggcgtggc gcgccgctat ggcggcgaat ggaccgaaga agcgggcgaa      420
cgcgcggcgc tgagcgaacg cctgtttgcg aacctgtggg gccgcctgga aggcgaagaa      480
```

-continued

```
cgcctgctgt ggctgtatcg cgaagtggaa cgcccgctga gcgcggtgct ggcgcatatg    540
gaagcgaccg gcgtgcgcct ggatgtggcg tatctgcgcg cgctgagcct ggaagtggcg    600
gaagaaattg cgcgcctgga agcggaagtg tttcgcctgg cgggccatcc gtttaacctg    660
aacagccgcg atcagctgga acgcgtgctg tttgatgaac tgggcctgcc ggcgattggc    720
aaaaccgaaa aaaccggcaa acgcagcacc agcgcggcgg tgctggaagc gctgcgcgaa    780
gcgcatccga ttgtggaaaa aattctgcag tatcgcgaac tgaccaaact gaaaagcacc    840
tatattgaag gcctgctgaa agtggtgcgc ccggataccc aaaaagtgca tacccgcttt    900
aaccagaccg cgaccgcgac cggccgcctg agcagcagcg atccgaacct gcagaacatt    960
ccggtgcgca ccccgctggg ccagcgcatt cgccgcgcgt ttattgcggg cgaaggctgg   1020
ctgctggtgg cgctggatta tagccagatt gaactgcgcg tgctggcgca tctgagcggc   1080
gatgaaaacc tgattcgcgt gtttcaggaa ggccgcgata ttcataccga aaccgcgagc   1140
tggatgtttg gcgtgccgcg cgaagcggtg gatccgctga tgcgccgcgc ggcgaaaacc   1200
attaactttg gcgtgctgta tggcatgagc gcgcatcgcc tgagccagga actggcgatt   1260
ccgtatgaag aagcgcaggc gtttattgaa cgctattttc agagctttcc gaaagtgcgc   1320
gcgtggattg aaaaaaccct ggaagaaggc cgccgccgcg gctatgtgga aaccctgttt   1380
ggccgccgcc gctatgtgcc ggatctggaa gcgcgcgtga aaagcgtgcg cgaagcggcg   1440
gaacgcatgg cgtttaacat gccggtgcag ggcaccgcgg cggatctgat gaaaagcgcg   1500
atggtgaaac tgtttccgcg cctggaagaa atgggcgcgc gcatgctgct gcaggtgcat   1560
gatgaactgg tgctggaagc gccgaaagaa cgcgcggaag cggtgcgcg cctggcgaaa   1620 gaagtgatgg aaggcgtgta tccgctggcg gtgccgctgg aagtggaagt gggcattggc   1680
gaagattggc tgagcgcgaa agaa                                          1704
```

<210> SEQ ID NO 3
<211> LENGTH: 592
<212> TYPE: PRT
<213> ORGANISM: Artificial Sequence
<220> FEATURE:
<223> OTHER INFORMATION: Synthetic Construct

<400> SEQUENCE: 3

```
Met Glu Ser Pro Ser Ser Glu Glu Lys Pro Leu Ala Lys Met Ala
1               5                   10                  15

Phe Thr Leu Ala Asp Arg Val Thr Glu Glu Met Leu Ala Asp Lys Ala
            20                  25                  30

Ala Leu Val Val Glu Val Val Glu Asn Tyr His Asp Ala Pro Ile
        35                  40                  45

Val Gly Ile Ala Val Val Asn Glu His Gly Arg Phe Phe Leu Arg Pro
    50                  55                  60

Glu Thr Ala Leu Ala Asp Pro Gln Phe Val Ala Trp Leu Gly Asp Glu
65                  70                  75                  80

Thr Lys Lys Lys Ser Met Phe Asp Ser Lys Arg Ala Ala Val Ala Leu
                85                  90                  95

Lys Trp Lys Gly Ile Glu Leu Cys Gly Val Ser Phe Asp Leu Leu Leu
            100                 105                 110

Ala Ala Tyr Leu Leu Asp Pro Ala Gln Gly Val Asp Val Ala Ala
        115                 120                 125

Ala Ala Lys Met Lys Gln Tyr Glu Ala Val Arg Pro Asp Glu Ala Val
    130                 135                 140
```

```
Tyr Gly Lys Gly Ala Lys Arg Ala Val Pro Asp Glu Pro Val Leu Ala
145                 150                 155                 160

Glu His Leu Val Arg Lys Ala Ala Ile Trp Glu Leu Glu Arg Pro
            165                 170                 175

Phe Leu Asp Glu Leu Arg Arg Asn Glu Gln Asp Arg Leu Leu Val Glu
            180                 185                 190

Leu Glu Gln Pro Leu Ser Ser Ile Leu Ala Glu Met Glu Phe Ala Gly
        195                 200                 205

Val Lys Val Asp Thr Lys Arg Leu Glu Gln Met Gly Lys Glu Leu Ala
    210                 215                 220

Glu Gln Leu Gly Thr Val Glu Gln Arg Ile Tyr Glu Leu Ala Gly Gln
225                 230                 235                 240

Glu Phe Asn Ile Asn Ser Pro Lys Gln Leu Gly Val Ile Leu Phe Glu
            245                 250                 255

Lys Leu Gln Leu Pro Val Leu Lys Lys Thr Lys Thr Gly Tyr Ser Thr
        260                 265                 270

Ser Ala Asp Val Leu Glu Lys Leu Ala Pro Tyr His Glu Ile Val Glu
    275                 280                 285

Asn Ile Leu His Tyr Arg Gln Leu Gly Lys Leu Gln Ser Thr Tyr Ile
290                 295                 300

Glu Gly Leu Leu Lys Val Val Arg Pro Asp Thr Lys Lys Val His Thr
305                 310                 315                 320

Ile Phe Asn Gln Ala Leu Thr Gln Thr Gly Arg Leu Ser Ser Thr Glu
            325                 330                 335

Pro Asn Leu Gln Asn Ile Pro Ile Arg Leu Glu Glu Gly Arg Lys Ile
        340                 345                 350

Arg Gln Ala Phe Val Pro Ser Glu Ser Asp Trp Leu Ile Phe Ala Ala
    355                 360                 365

Asp Tyr Ser Gln Ile Glu Leu Arg Val Leu Ala His Ile Ala Glu Asp
        370                 375                 380

Asp Asn Leu Met Glu Ala Phe Arg Arg Asp Leu Asp Ile His Thr Lys
385                 390                 395                 400

Thr Ala Met Asp Ile Phe Gln Val Ser Glu Asp Glu Val Thr Pro Asn
            405                 410                 415

Met Arg Arg Gln Ala Lys Ala Val Asn Phe Gly Ile Val Tyr Gly Ile
            420                 425                 430

Ser Asp Tyr Gly Leu Ala Gln Asn Leu Asn Ile Ser Arg Lys Glu Ala
        435                 440                 445

Ala Glu Phe Ile Glu Arg Tyr Phe Glu Ser Phe Pro Gly Val Lys Arg
    450                 455                 460

Tyr Met Glu Asn Ile Val Gln Glu Ala Lys Gln Lys Gly Tyr Val Thr
465                 470                 475                 480

Thr Leu Leu His Arg Arg Arg Tyr Leu Pro Asp Ile Thr Ser Arg Asn
            485                 490                 495

Phe Asn Val Arg Ser Phe Ala Glu Arg Met Ala Met Asn Thr Pro Ile
            500                 505                 510

Gln Gly Ser Ala Ala Asp Ile Ile Lys Lys Ala Met Ile Asp Leu Asn
        515                 520                 525

Ala Arg Leu Lys Glu Glu Arg Leu Gln Ala His Leu Leu Leu Gln Val
    530                 535                 540

His Asp Glu Leu Ile Leu Glu Ala Pro Lys Glu Glu Met Glu Arg Leu
545                 550                 555                 560

Cys Arg Leu Val Pro Glu Val Met Glu Gln Ala Val Thr Leu Arg Val
```

```
                        565                 570                 575

Pro Leu Lys Val Asp Tyr His Tyr Gly Ser Thr Trp Tyr Asp Ala Lys
                580                 585                 590

<210> SEQ ID NO 4
<211> LENGTH: 553
<212> TYPE: PRT
<213> ORGANISM: Artificial Sequence
<220> FEATURE:
<223> OTHER INFORMATION: Synthetic Construct

<400> SEQUENCE: 4

Met Leu Leu His Glu Phe Gly Leu Leu Glu Ser Pro Lys Ala Leu Glu
1               5                   10                  15

Glu Ala Pro Trp Pro Pro Glu Gly Ala Phe Val Gly Phe Val Leu
            20                  25                  30

Ser Arg Lys Glu Pro Met Trp Ala Asp Leu Leu Ala Leu Ala Ala Ala
        35                  40                  45

Arg Gly Gly Arg Val His Arg Ala Pro Glu Pro Tyr Lys Ala Leu Arg
    50                  55                  60

Asp Leu Lys Glu Ala Arg Gly Leu Leu Ala Lys Asp Leu Ser Val Leu
65                  70                  75                  80

Ala Leu Arg Glu Gly Leu Gly Leu Pro Pro Gly Asp Asp Pro Met Leu
                85                  90                  95

Leu Ala Tyr Leu Leu Asp Pro Ser Asn Thr Thr Pro Glu Gly Val Ala
            100                 105                 110

Arg Arg Tyr Gly Gly Glu Trp Thr Glu Glu Ala Gly Glu Arg Ala Ala
        115                 120                 125

Leu Ser Glu Arg Leu Phe Ala Asn Leu Trp Gly Arg Leu Glu Gly Glu
    130                 135                 140

Glu Arg Leu Leu Trp Leu Tyr Arg Glu Val Glu Arg Pro Leu Ser Ala
145                 150                 155                 160

Val Leu Ala His Met Glu Ala Thr Gly Val Arg Leu Asp Val Ala Tyr
                165                 170                 175

Leu Arg Ala Leu Ser Leu Glu Val Ala Glu Glu Ile Ala Arg Leu Glu
            180                 185                 190

Ala Glu Val Phe Arg Leu Ala Gly His Pro Phe Asn Leu Asn Ser Arg
        195                 200                 205

Asp Gln Leu Glu Arg Val Leu Phe Asp Glu Leu Gly Leu Pro Ala Ile
    210                 215                 220

Gly Lys Thr Glu Lys Thr Gly Lys Arg Ser Thr Ser Ala Ala Val Leu
225                 230                 235                 240

Glu Ala Leu Arg Glu Ala His Pro Ile Val Glu Lys Ile Leu Gln Tyr
                245                 250                 255

Arg Glu Leu Thr Lys Leu Lys Ser Thr Tyr Ile Asp Pro Leu Pro Asp
            260                 265                 270

Leu Ile His Pro Arg Thr Gly Arg Leu His Thr Arg Phe Asn Gln Thr
        275                 280                 285

Ala Thr Ala Thr Gly Arg Leu Ser Ser Ser Asp Pro Asn Leu Gln Asn
    290                 295                 300

Ile Pro Val Arg Thr Pro Leu Gly Gln Arg Ile Arg Arg Ala Phe Ile
305                 310                 315                 320

Ala Glu Glu Gly Trp Leu Leu Val Ala Leu Asp Tyr Ser Gln Ile Glu
                325                 330                 335

Leu Arg Val Leu Ala His Leu Ser Gly Asp Glu Asn Leu Ile Arg Val
```

```
                    340                 345                 350
Phe Gln Glu Gly Arg Asp Ile His Thr Glu Thr Ala Ser Trp Met Phe
            355                 360                 365

Gly Val Pro Arg Glu Ala Val Asp Pro Leu Met Arg Arg Ala Ala Lys
        370                 375                 380

Thr Ile Asn Phe Gly Val Leu Tyr Gly Met Ser Ala His Arg Leu Ser
385                 390                 395                 400

Gln Glu Leu Ala Ile Pro Tyr Glu Glu Ala Gln Ala Phe Ile Glu Arg
                405                 410                 415

Tyr Phe Gln Ser Phe Pro Lys Val Arg Ala Trp Ile Glu Lys Thr Leu
            420                 425                 430

Glu Glu Gly Arg Arg Arg Gly Tyr Val Glu Thr Leu Phe Gly Arg Arg
        435                 440                 445

Arg Tyr Val Pro Asp Leu Glu Ala Arg Val Lys Ser Val Arg Glu Ala
    450                 455                 460

Ala Glu Arg Met Ala Phe Asn Met Pro Val Gln Gly Thr Ala Ala Asp
465                 470                 475                 480

Leu Met Lys Leu Ala Met Val Lys Leu Phe Pro Arg Leu Glu Glu Met
                485                 490                 495

Gly Ala Arg Met Leu Leu Gln Val His Asp Glu Leu Val Leu Glu Ala
            500                 505                 510

Pro Lys Glu Arg Ala Glu Ala Val Ala Arg Leu Ala Lys Glu Val Met
        515                 520                 525

Glu Gly Val Tyr Pro Leu Ala Val Pro Leu Glu Val Glu Val Gly Ile
    530                 535                 540

Gly Glu Asp Trp Leu Ser Ala Lys Glu
545                 550

<210> SEQ ID NO 5
<211> LENGTH: 592
<212> TYPE: PRT
<213> ORGANISM: Artificial Sequence
<220> FEATURE:
<223> OTHER INFORMATION: Synthetic Construct

<400> SEQUENCE: 5

Met Glu Ser Pro Ser Ser Glu Glu Lys Pro Leu Ala Lys Met Ala
1               5                   10                  15

Phe Thr Leu Ala Asp Arg Val Thr Glu Glu Met Leu Ala Asp Lys Ala
            20                  25                  30

Ala Leu Val Val Glu Val Glu Glu Asn Tyr His Asp Ala Pro Ile
        35                  40                  45

Val Gly Ile Ala Val Val Asn Glu His Gly Arg Phe Phe Leu Arg Pro
    50                  55                  60

Glu Thr Ala Leu Ala Asp Pro Gln Phe Val Ala Trp Leu Gly Asp Glu
65                  70                  75                  80

Thr Lys Lys Lys Ser Met Phe Asp Ser Lys Arg Ala Ala Val Ala Leu
                85                  90                  95

Lys Trp Lys Gly Ile Glu Leu Cys Gly Val Ser Phe Asp Leu Leu Leu
            100                 105                 110

Ala Ala Tyr Leu Leu Asp Pro Ala Gln Gly Val Asp Asp Val Ala Ala
        115                 120                 125

Ala Ala Lys Met Lys Gln Tyr Glu Ala Val Arg Pro Asp Glu Ala Val
    130                 135                 140

Tyr Gly Lys Gly Ala Lys Arg Ala Val Pro Asp Glu Pro Val Leu Ala
```

-continued

|     |     |     | 145 |     |     |     | 150 |     |     |     | 155 |     |     |     | 160 |
| --- | --- | --- | --- | --- | --- | --- | --- | --- | --- | --- | --- | --- | --- | --- | --- |

Glu His Leu Val Arg Lys Ala Ala Ile Trp Leu Arg Pro
                165                 170                 175

Phe Leu Asp Glu Leu Arg Arg Asn Glu Gln Asp Arg Leu Leu Val Glu
                180                 185                 190

Leu Glu Gln Pro Leu Ser Ser Ile Leu Ala Glu Met Glu Phe Ala Gly
                195                 200                 205

Val Lys Val Asp Thr Lys Arg Leu Glu Gln Met Gly Lys Glu Leu Ala
210                 215                 220

Gly Gln Leu Gly Thr Val Glu Gln Arg Ile Tyr Glu Leu Ala Gly Gln
225                 230                 235                 240

Glu Phe Asn Ile Asn Ser Pro Lys Arg Leu Gly Val Ile Leu Phe Glu
                245                 250                 255

Lys Leu Gln Leu Pro Val Leu Lys Lys Thr Lys Thr Gly Tyr Ser Thr
                260                 265                 270

Ser Ala Asp Val Leu Glu Lys Leu Ala Pro Tyr His Glu Ile Val Glu
                275                 280                 285

Asn Ile Leu His Tyr Arg Gln Leu Gly Lys Leu Gln Ser Thr Tyr Ile
290                 295                 300

Glu Gly Leu Leu Lys Val Val Arg Pro Asp Thr Lys Lys Val His Thr
305                 310                 315                 320

Ile Phe Asn Gln Ala Leu Thr Gln Thr Gly Arg Leu Ser Ser Thr Glu
                325                 330                 335

Pro Asn Leu Gln Asn Ile Pro Ile Arg Leu Glu Glu Gly Arg Lys Ile
                340                 345                 350

Arg Gln Ala Phe Val Pro Ser Glu Ser Asp Trp Leu Ile Phe Ala Ala
                355                 360                 365

Asp Tyr Ser Gln Ile Glu Leu Arg Val Leu Ala His Ile Ala Glu Asp
                370                 375                 380

Asp Asn Leu Met Glu Ala Phe Arg Arg Asp Leu Asp Ile His Thr Lys
385                 390                 395                 400

Thr Ala Met Asp Ile Phe Gln Val Ser Glu Asp Glu Val Thr Pro Ser
                405                 410                 415

Met Arg Arg Gln Ala Lys Ala Val Asn Phe Gly Ile Val Tyr Gly Ile
                420                 425                 430

Ser Asp Tyr Gly Leu Ala Gln Asn Leu Asn Ile Ser Arg Lys Glu Ala
                435                 440                 445

Ala Glu Phe Ile Gly Arg Tyr Phe Glu Ser Phe Pro Gly Val Lys Arg
                450                 455                 460

Tyr Met Glu Asn Ile Val Gln Glu Ala Lys Gln Lys Gly Tyr Val Thr
465                 470                 475                 480

Thr Leu Leu His Arg Arg Arg Tyr Leu Pro Asp Ile Thr Ser Arg Asn
                485                 490                 495

Phe Asn Val Arg Ser Phe Ala Glu Arg Met Ala Met Asn Thr Pro Ile
                500                 505                 510

Gln Gly Ser Ala Ala Asp Ile Ile Lys Lys Ala Met Ile Asp Leu Asn
                515                 520                 525

Ala Arg Leu Lys Glu Glu Arg Leu Gln Ala His Leu Leu Leu Gln Val
                530                 535                 540

His Asp Glu Leu Ile Leu Glu Ala Pro Lys Glu Glu Met Glu Arg Leu
545                 550                 555                 560

Cys Arg Leu Val Pro Glu Val Met Glu Gln Ala Val Thr Leu Arg Val
                565                 570                 575

Pro Leu Lys Val Asp Tyr His Tyr Gly Ser Thr Trp Tyr Asp Ala Lys
                580                 585                 590

<210> SEQ ID NO 6
<211> LENGTH: 370
<212> TYPE: DNA
<213> ORGANISM: Artificial Sequence
<220> FEATURE:
<223> OTHER INFORMATION: Synthetic Construct

<400> SEQUENCE: 6
ctagtaacgg ccgccagtgt gctggaattc ggtagatcca ttgtggtccc ttgccgccac     60
caagatgaat tgattggccg agcccgtgta tcaccagggg caggatggag cattcgggag    120
actgcctgtc tagcaaaatc atatgcacag atgtggcagc ttctttactt ccacagaaga    180
gaccttcgac tgatggccaa tgctatttgt tcggctgtgc cagttgactg ggtaccaacc    240
gggagaacca cctggtcaat ccacggaaag ggagaatgga tgactactga ggacatgctc    300
atggtgtgga atagagtgtg gattgaggag gaattctgca gatatccatc acactggcgg    360
ccgctcgagc                                                           370

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
gtcatccart ctccrttrcc                                                 20

<210> SEQ ID NO 8
<211> LENGTH: 19
<212> TYPE: DNA
<213> ORGANISM: Artificial Sequence
<220> FEATURE:
<223> OTHER INFORMATION: Synthetic Construct

<400> SEQUENCE: 8
atccattgtg gtyccytgy                                                  19

<210> SEQ ID NO 9
<211> LENGTH: 22
<212> TYPE: DNA
<213> ORGANISM: Artificial Sequence
<220> FEATURE:
<223> OTHER INFORMATION: Synthetic Construct

<400> SEQUENCE: 9
tgctccatcc ygccccyggh ga                                              22

<210> SEQ ID NO 10
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (33)..(33)
<223> OTHER INFORMATION: n is a, c, g, or t

<400> SEQUENCE: 10
atgcvcarat gtggcagcty cttccchgtt ggnaccca                             38

<210> SEQ ID NO 11
<211> LENGTH: 41
<212> TYPE: DNA
<213> ORGANISM: Artificial Sequence
<220> FEATURE:
<223> OTHER INFORMATION: Synthetic Construct

<400> SEQUENCE: 11
gchagrcarg cagtctcmcg rgatgaaytg attggccgrg c               41

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct

<400> SEQUENCE: 12
ttttcgtgtg aatatcaaga tcgc                                  24

<210> SEQ ID NO 13
<211> LENGTH: 40
<212> TYPE: DNA
<213> ORGANISM: Artificial Sequence
<220> FEATURE:
<223> OTHER INFORMATION: Synthetic Construct

<400> SEQUENCE: 13
ttagaaaaat aaacaaatag gggttccgcg cacatttccc                 40

<210> SEQ ID NO 14
<211> LENGTH: 33
<212> TYPE: DNA
<213> ORGANISM: Artificial Sequence
<220> FEATURE:
<223> OTHER INFORMATION: Synthetic Construct

<400> SEQUENCE: 14
gggaactgcc agacatcaaa taaaacaaaa ggc                        33

<210> SEQ ID NO 15
<211> LENGTH: 41
<212> TYPE: DNA
<213> ORGANISM: Artificial Sequence
<220> FEATURE:
<223> OTHER INFORMATION: Synthetic Construct

<400> SEQUENCE: 15
ctggcctttt gctcacatga cccgacacca tcgaatggcc g               41

<210> SEQ ID NO 16
<211> LENGTH: 21
<212> TYPE: DNA
<213> ORGANISM: Artificial Sequence
<220> FEATURE:
<223> OTHER INFORMATION: Synthetic Construct

<400> SEQUENCE: 16
acagtcattc atctttctgc c                                     21

<210> SEQ ID NO 17
<211> LENGTH: 26
<212> TYPE: DNA
<213> ORGANISM: Artificial Sequence
<220> FEATURE:

<223> OTHER INFORMATION: Synthetic Construct

<400> SEQUENCE: 17
cagaccctaa tttcacatca tatgac                                              26

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
cttttgctca catgacccga                                                     20

<210> SEQ ID NO 19
<211> LENGTH: 27
<212> TYPE: DNA
<213> ORGANISM: Artificial Sequence
<220> FEATURE:
<223> OTHER INFORMATION: Synthetic Construct

<400> SEQUENCE: 19
gtttaacttt aagaaggagt aggatcc                                             27

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20
gaggacagaa tttgaatgca agc                                                 23

<210> SEQ ID NO 21
<211> LENGTH: 34
<212> TYPE: DNA
<213> ORGANISM: Artificial Sequence
<220> FEATURE:
<223> OTHER INFORMATION: Synthetic Construct

<400> SEQUENCE: 21
gcgatacaga ccctaatttc acatcatatg acac                                     34

<210> SEQ ID NO 22
<211> LENGTH: 28
<212> TYPE: DNA
<213> ORGANISM: Artificial Sequence
<220> FEATURE:
<223> OTHER INFORMATION: Synthetic Construct

<400> SEQUENCE: 22
aagcttgcat tcaaattctg tcctcaag                                            28

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
ggccttttgc tcacatgacc c                                                   21

```
<210> SEQ ID NO 24
<211> LENGTH: 26
<212> TYPE: DNA
<213> ORGANISM: Artificial Sequence
<220> FEATURE:
<223> OTHER INFORMATION: Synthetic Construct

<400> SEQUENCE: 24
ggactataaa gataccaggc gtttcc                                          26

<210> SEQ ID NO 25
<211> LENGTH: 26
<212> TYPE: DNA
<213> ORGANISM: Artificial Sequence
<220> FEATURE:
<223> OTHER INFORMATION: Synthetic Construct

<400> SEQUENCE: 25
gaacgaccta caccgaactg agatac                                          26

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
gcagcagcca ctggtaacag                                                 20

<210> SEQ ID NO 27
<211> LENGTH: 27
<212> TYPE: DNA
<213> ORGANISM: Artificial Sequence
<220> FEATURE:
<223> OTHER INFORMATION: Synthetic Construct

<400> SEQUENCE: 27
cggatcaaga gctaccaact cttttc                                          27

<210> SEQ ID NO 28
<211> LENGTH: 27
<212> TYPE: DNA
<213> ORGANISM: Artificial Sequence
<220> FEATURE:
<223> OTHER INFORMATION: Synthetic Construct

<400> SEQUENCE: 28
ctcagtggaa cgaaaactca cgttaag                                         27

<210> SEQ ID NO 29
<211> LENGTH: 35
<212> TYPE: DNA
<213> ORGANISM: Artificial Sequence
<220> FEATURE:
<223> OTHER INFORMATION: Synthetic Construct

<400> SEQUENCE: 29
ccttgaattg atcatatgcg gattagaaaa acaac                                35

<210> SEQ ID NO 30
<211> LENGTH: 28
<212> TYPE: DNA
<213> ORGANISM: Artificial Sequence
<220> FEATURE:
<223> OTHER INFORMATION: Synthetic Construct
```

<400> SEQUENCE: 30
ctttagcgac ttgatgctct tgatcttc                                       28

<210> SEQ ID NO 31
<211> LENGTH: 27
<212> TYPE: DNA
<213> ORGANISM: Artificial Sequence
<220> FEATURE:
<223> OTHER INFORMATION: Synthetic Construct

<400> SEQUENCE: 31
gtacacggcc tacagaaaaa cagtatg                                        27

<210> SEQ ID NO 32
<211> LENGTH: 27
<212> TYPE: DNA
<213> ORGANISM: Artificial Sequence
<220> FEATURE:
<223> OTHER INFORMATION: Synthetic Construct

<400> SEQUENCE: 32
gtatggtgcc tatctaacat ctcaatg                                        27

<210> SEQ ID NO 33
<211> LENGTH: 26
<212> TYPE: DNA
<213> ORGANISM: Artificial Sequence
<220> FEATURE:
<223> OTHER INFORMATION: Synthetic Construct

<400> SEQUENCE: 33
cagcgcatta gagctgctta atgagg                                         26

<210> SEQ ID NO 34
<211> LENGTH: 24
<212> TYPE: DNA
<213> ORGANISM: Artificial Sequence
<220> FEATURE:
<223> OTHER INFORMATION: Synthetic Construct

<400> SEQUENCE: 34
ctccccgtcg tgtagataac tacg                                           24

<210> SEQ ID NO 35
<211> LENGTH: 24
<212> TYPE: DNA
<213> ORGANISM: Artificial Sequence
<220> FEATURE:
<223> OTHER INFORMATION: Synthetic Construct

<400> SEQUENCE: 35
cggataaagt tgcaggacca cttc                                           24

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
cgtttggtat ggcttcattc agctc                                          25

<210> SEQ ID NO 37
<211> LENGTH: 23

```
<212> TYPE: DNA
<213> ORGANISM: Artificial Sequence
<220> FEATURE:
<223> OTHER INFORMATION: Synthetic Construct

<400> SEQUENCE: 37
cagtgctgcc ataaccatga gtg                                    23

<210> SEQ ID NO 38
<211> LENGTH: 23
<212> TYPE: DNA
<213> ORGANISM: Artificial Sequence
<220> FEATURE:
<223> OTHER INFORMATION: Synthetic Construct

<400> SEQUENCE: 38
caatacggga taataccgcg cca                                    23

<210> SEQ ID NO 39
<211> LENGTH: 29
<212> TYPE: DNA
<213> ORGANISM: Artificial Sequence
<220> FEATURE:
<223> OTHER INFORMATION: Synthetic Construct

<400> SEQUENCE: 39
gctggtgaaa gtaaaagatg ctgaagatc                              29

<210> SEQ ID NO 40
<211> LENGTH: 27
<212> TYPE: DNA
<213> ORGANISM: Artificial Sequence
<220> FEATURE:
<223> OTHER INFORMATION: Synthetic Construct

<400> SEQUENCE: 40
cagggttatt gtctcatgag cggatac                                27

<210> SEQ ID NO 41
<211> LENGTH: 30
<212> TYPE: DNA
<213> ORGANISM: Artificial Sequence
<220> FEATURE:
<223> OTHER INFORMATION: Synthetic Construct

<400> SEQUENCE: 41
gagtgttcac cgacaaacaa cagataaaac                             30

<210> SEQ ID NO 42
<211> LENGTH: 59
<212> TYPE: DNA
<213> ORGANISM: Artificial Sequence
<220> FEATURE:
<223> OTHER INFORMATION: Synthetic Construct

<400> SEQUENCE: 42
cgcttgagga cagaattttg gcagaggcaa ttatcatttc gcatcgtacc aagtacttc    59

<210> SEQ ID NO 43
<211> LENGTH: 60
<212> TYPE: DNA
<213> ORGANISM: Artificial Sequence
<220> FEATURE:
<223> OTHER INFORMATION: Synthetic Construct

<400> SEQUENCE: 43
```
cgcttgagga cagaattttg gcagaggcaa ttatcattct ttcgcagata accaatcttc    60

<210> SEQ ID NO 44
<211> LENGTH: 96
<212> TYPE: DNA
<213> ORGANISM: Artificial Sequence
<220> FEATURE:
<223> OTHER INFORMATION: Synthetic Construct

<400> SEQUENCE: 44
tttgtttaac tttaagaagg agatatacat atggctagca gaggatcgca tcaccatcac    60
catcacatcg aagggcgcga aagtcccagc agcgag    96

<210> SEQ ID NO 45
<211> LENGTH: 97
<212> TYPE: DNA
<213> ORGANISM: Artificial Sequence
<220> FEATURE:
<223> OTHER INFORMATION: Synthetic Construct

<400> SEQUENCE: 45
tttgtttaac tttaagaagg agatatacat atggctagca gaggatcgca tcaccatcac    60
catcacatcg aagggcgcct tcttcacgag ttcggac    97

<210> SEQ ID NO 46
<211> LENGTH: 18
<212> TYPE: DNA
<213> ORGANISM: Artificial Sequence
<220> FEATURE:
<223> OTHER INFORMATION: Synthetic Construct

<400> SEQUENCE: 46
gccacccaga agactgtg    18

<210> SEQ ID NO 47
<211> LENGTH: 20
<212> TYPE: DNA
<213> ORGANISM: Artificial Sequence
<220> FEATURE:
<223> OTHER INFORMATION: Synthetic Construct

<400> SEQUENCE: 47
tggcaggttt ttctagacgg    20

<210> SEQ ID NO 48
<211> LENGTH: 39
<212> TYPE: DNA
<213> ORGANISM: Artificial Sequence
<220> FEATURE:
<223> OTHER INFORMATION: Synthetic Construct

<400> SEQUENCE: 48
cgccagtaga ggcagggatg agggaaactg tggcgtgat    39

<210> SEQ ID NO 49
<211> LENGTH: 40
<212> TYPE: DNA
<213> ORGANISM: Artificial Sequence
<220> FEATURE:
<223> OTHER INFORMATION: Synthetic Construct

<400> SEQUENCE: 49
ggtcatccct gagctgaacg gtcaggtcca ccactgacac    40

```
<210> SEQ ID NO 50
<211> LENGTH: 22
<212> TYPE: DNA
<213> ORGANISM: Artificial Sequence
<220> FEATURE:
<223> OTHER INFORMATION: Synthetic Construct

<400> SEQUENCE: 50
tgttctggag agccccgcgg cc                                              22

<210> SEQ ID NO 51
<211> LENGTH: 482
<212> TYPE: DNA
<213> ORGANISM: Artificial Sequence
<220> FEATURE:
<223> OTHER INFORMATION: Synthetic Construct

<400> SEQUENCE: 51
ctagtaacgg ccgccagtgt gctggaattc ccacagtcca tgccatcact gccacccaga     60
agactgtgga tggcccctcc gggaaactgt ggcgtgatgg ccgcgggct ctccagaaca     120 tcatccctgc ctctactggc gctgccaagg ctgtgggcaa ggtcatccct gagctgaacg     180
ggaagctcac tggcatggcc ttccgtgtcc ccactgccaa cgtgtcagtg gtggacctga     240
cctgccgtct agaaaaacct gccaaatatg atgacatcaa gaaggtggtg aagcaggcgt     300
cggagggccc cctcaagggc atcctgggct acactgagca ccaggtggtc tcctctgact     360
tcaacagcga cacccactcc tccacctttg acgctggggc tggcattgcc ctcaacgacc     420
actttgtcaa gctcatttcc tggaattctg cagatatcca tcacactggc ggccgctcga     480
gc                                                                   482

<210> SEQ ID NO 52
<211> LENGTH: 306
<212> TYPE: DNA
<213> ORGANISM: Artificial Sequence
<220> FEATURE:
<223> OTHER INFORMATION: Synthetic Construct

<400> SEQUENCE: 52
taatacgact cactataggg cgtgaatctt aatttacccg caaatgtccc atactctcgt     60
gttatttcca ggatgggctt taaactcgat gcaacagttc ctggatatcc taagcttttc    120
attactcgtg aagaggctgt aaggcaagtt cgaagctgga taggcttcga tgttgagggt    180
gctcatgctt cccgtaatgc atgtggcacc aatgtgcctc tacaattagg attttcaact    240
ggtgtgaact tgttgttca gccagttggt gttgtagaca ctgagtcctg acgagtgggt    300
ttaacg                                                               306

<210> SEQ ID NO 53
<211> LENGTH: 21
<212> TYPE: DNA
<213> ORGANISM: Artificial Sequence
<220> FEATURE:
<223> OTHER INFORMATION: Synthetic Construct

<400> SEQUENCE: 53
acagttcctg gatatcctaa g                                              21

<210> SEQ ID NO 54
<211> LENGTH: 19
<212> TYPE: DNA
<213> ORGANISM: Artificial Sequence
<220> FEATURE:
```

<223> OTHER INFORMATION: Synthetic Construct

<400> SEQUENCE: 54
ctcagtgtct acaacacca                                                    19

<210> SEQ ID NO 55
<211> LENGTH: 38
<212> TYPE: DNA
<213> ORGANISM: Artificial Sequence
<220> FEATURE:
<223> OTHER INFORMATION: Synthetic Construct

<400> SEQUENCE: 55
agcaccctca acatcgaagc actcgtgaag aggctgta                               38

<210> SEQ ID NO 56
<211> LENGTH: 40
<212> TYPE: DNA
<213> ORGANISM: Artificial Sequence
<220> FEATURE:
<223> OTHER INFORMATION: Synthetic Construct

<400> SEQUENCE: 56
tgcttcccgt aatgcatgtg gactggctga acaacaaagt                             40

<210> SEQ ID NO 57
<211> LENGTH: 22
<212> TYPE: DNA
<213> ORGANISM: Artificial Sequence
<220> FEATURE:
<223> OTHER INFORMATION: Synthetic Construct

<400> SEQUENCE: 57
ctatccagct tcgaacttgc ct                                                22

<210> SEQ ID NO 58
<211> LENGTH: 40
<212> TYPE: DNA
<213> ORGANISM: Artificial Sequence
<220> FEATURE:
<223> OTHER INFORMATION: Synthetic Construct

<400> SEQUENCE: 58
cacaccagtt gaaaatccta attgtagagg cacattggtg                             40

<210> SEQ ID NO 59
<211> LENGTH: 29
<212> TYPE: DNA
<213> ORGANISM: Artificial Sequence
<220> FEATURE:
<223> OTHER INFORMATION: Synthetic Construct

<400> SEQUENCE: 59
ctctacaatt aggattttca actggtgtg                                         29

<210> SEQ ID NO 60
<211> LENGTH: 371
<212> TYPE: DNA
<213> ORGANISM: Artificial Sequence
<220> FEATURE:
<223> OTHER INFORMATION: Synthetic Construct

<400> SEQUENCE: 60
taatacgact cactataggg cttgtgacta tggccttcgt tatgttgttg gttaaacaca       60
aacacacctt tttgacactt ttcttgttgc ctgtggctat ttgtttgact tatgcaaaca     120
tagtctacga gcccactact cccatttcgt cagcgctgat tgcagttgca aattggcttg    180 ccccactaa tgcttatatg cgcactacac atactgatat tggtgtctac attagtatgt    240
cacttgtatt agtcattgta gtgaagagat tgtacaaccc atcactttct aactttgcgt    300
tagcattgtg cagtggtgta atgtggttgt acacttatag cattggagaa gcctgacgag    360
tgggtttaac g    371

<210> SEQ ID NO 61
<211> LENGTH: 22
<212> TYPE: DNA
<213> ORGANISM: Artificial Sequence
<220> FEATURE:
<223> OTHER INFORMATION: Synthetic Construct

<400> SEQUENCE: 61
ttatgcaaac atagtctacg ag    22

<210> SEQ ID NO 62
<211> LENGTH: 21
<212> TYPE: DNA
<213> ORGANISM: Artificial Sequence
<220> FEATURE:
<223> OTHER INFORMATION: Synthetic Construct

<400> SEQUENCE: 62
cgcaaagtta gaaagtgatg g    21

<210> SEQ ID NO 63
<211> LENGTH: 38
<212> TYPE: DNA
<213> ORGANISM: Artificial Sequence
<220> FEATURE:
<223> OTHER INFORMATION: Synthetic Construct

<400> SEQUENCE: 63
aagcattagt gggggcaagc cccactactc ccatttcg    38

<210> SEQ ID NO 64
<211> LENGTH: 48
<212> TYPE: DNA
<213> ORGANISM: Artificial Sequence
<220> FEATURE:
<223> OTHER INFORMATION: Synthetic Construct

<400> SEQUENCE: 64
atgcgcacta cacatactga tatttgtaca atctcttcac tacaatga    48

<210> SEQ ID NO 65
<211> LENGTH: 31
<212> TYPE: DNA
<213> ORGANISM: Artificial Sequence
<220> FEATURE:
<223> OTHER INFORMATION: Synthetic Construct

<400> SEQUENCE: 65
ggtgtctaca ttagtatgtc acttgtatta g    31

<210> SEQ ID NO 66
<211> LENGTH: 33
<212> TYPE: DNA
<213> ORGANISM: Artificial Sequence
<220> FEATURE:
<223> OTHER INFORMATION: Synthetic Construct

```
<400> SEQUENCE: 66
cgaagccaat ttgcaactgc aatcagcgct gag                             33

<210> SEQ ID NO 67
<211> LENGTH: 23
<212> TYPE: DNA
<213> ORGANISM: Artificial Sequence
<220> FEATURE:
<223> OTHER INFORMATION: Synthetic Construct

<400> SEQUENCE: 67
attgcagttg caaattggct tcg                                        23

<210> SEQ ID NO 68
<211> LENGTH: 325
<212> TYPE: DNA
<213> ORGANISM: Artificial Sequence
<220> FEATURE:
<223> OTHER INFORMATION: Synthetic Construct

<400> SEQUENCE: 68
cactcattgg cacagtggta gttagaggtg aaaagtagag ctgtcaagcc caagggctta    60
gctttagggc tcctcctgag ttcggcccac agtagaagca agattttaac tagcccttt    120 tcctcttcac cctcccatga tgcgcagtgt tcagaaagct ggtaagtcct agggatttcc    180
agaagtagcc tgcagaagaa ggtaagtttg aaagccactc caggggtcct gatgctgtca    240
tgctcagtga gccattttac agttctccaa agtctagccc tgtttcggac ctgcacttca    300
cctctaagtt atgtacaact caacc                                        325
```

METHODS AND DEVICES RELATED TO AMPLIFYING NUCLEIC ACID AT A VARIETY OF TEMPERATURES

CROSS-REFERENCE TO RELATED APPLICATIONS

This application claims benefit of U.S. Provisional Application No. 62/504,250, filed May 10, 2017, incorporated herein by reference in its entirety.

ACKNOWLEDGEMENTS

This invention was made with government support under Grant No. GM128446 awarded by the National Institutes of Health, Grant Nos. CMMI1761743 and 1541244 awarded by the National Science Foundation, Grant No. W911NF-17-1-0561 awarded by the Army Research Office, Grant No. 80NSSC17K0520 awarded by National Aeronautics and Space Administration (NASA), and Grant No. FA9550-14-1-0089 awarded by the Air Force Office of Scientific Research. The government has certain rights in the invention.

BACKGROUND

A. Background for Thermophilic Strand-Displacing Polymerase

Over the last several decades, isothermal nucleic acid amplification (IA) has become a transformative technology for point of care diagnostics that seek to deliver clinical results to patients in near real-time (Craw 2012; Hartman 2013). Because IA methods seek to amplify DNA or RNA via continuous replication at a single temperature, they obviate the need for thermal cyclers and can reduce the time to result (Craw 2012; Gill 2008; Mori 2013; Njiru 2012; Zhao 2015). These assay advantages have in turn enabled the creation of a variety of fascinating and useful point of care devices (Craw 2012; Hartman 2013; Mori 2013; Zhao 2015; Asiello 2011; Du 2015; Jiang 2015).

While some IA mechanisms depend upon multiple enzymes, including nickases, recombinases, and ligases, to achieve continuous replication, rolling circle amplification (RCA) and loop-mediated isothermal amplification (LAMP) require only polymerases and primers (Gill 2008; Notomi 2000; Dean 2001). RCA can proceed at mesophilic or higher temperatures, amplifying continuously around a circular template to generate long, concatenated DNA products (Jiang 2013). When initiated from a nick or single primer, amplification is linear; by including both forward and reverse primers, however, amplification becomes exponential, generating $10^9$-fold amplification in 90 minutes from 10 copies of template in a reaction commonly referred to as hyperbranched RCA (hbRCA) (Craw 2012; Dean 2001; Lizardi 1998; Zhang 2001). LAMP, also exponential, is currently an inherently higher temperature mechanism, using 4-6 primers to generate $10^9$-fold amplification of short (100-500 bp) DNA targets in an hour or less by creating ladder-like concatenated amplicons (Njiru 2012; Notomi 2000; Bhadra 2015). Overall, both methods are rapid, single-enzyme DNA detection systems that are comparable to PCR in terms of sensitivity, yet are faster and can operate isothermally, likely explaining their prevalence in point of care assays and devices (Craw 2012; Zhao 2015).

Like many IA strategies, LAMP and RCA rely upon the inherent strand displacement activity of a polymerase to displace downstream DNA, thereby enabling continuous replication without thermal cycling (Gill 2008; Zhao 2015). There are only a limited number of polymerases with strong strand displacement characteristics, primarily the large fragment (exo-) of *Geobacillus stearothermophilus* pol I (Bst LF) for high temperature reactions (65-70° C., (Kiefer 1997)) or the *Bacillus subtilis* phage phi29 polymerase (φ29) for low temperature reactions (≤30° C., (Blanco 1989)). These polymerases are also highly processive (Kiefer 1997; Blanco 1989), a property that often coincides with strand displacement and that makes them useful for sequencing otherwise difficult DNA molecules (McClary 1991; Ye 1987; Zhang 2006).

Unfortunately, while many IA mechanisms depend upon an initial heating step (~95° C.) for template denaturation (Craw 2012), both φ29 and Bst LF are denatured at much lower temperatures (phi29 at 37° C., Bst at 80° C.). Thus, some IA reactions require opening reaction tubes and adding polymerase after the heating step, which is both cumbersome and risky due to the common issues of spurious amplification and cross-contamination inherent in ultrasensitive IA strategies (Craw 2012; Hsieh 2014). While many IA mechanisms including LAMP and some versions of RCA do not necessarily require template denaturation, pre-reaction heating can nonetheless improve assay sensitivity (Njiru 2008; Suzuki 2010), reduce amplification inhibition from crude clinical samples (Verkooyen 1996; Modak 2016), and serve as a nucleic acid extraction method for detection of viruses and bacteria (Fereidouni 2015; Queipo-Ortuno 2008). Thus, there is a pressing need for thermostable polymerases that possess significant strand displacement activity for both IA and PCR methods.

B. Background for Phosphorothioated Loop-Mediated Isothermal Amplification (PS-LAMP)

Loop-mediated isothermal amplification (LAMP) introduced by Notomi et al. (Notomi 2000) is a highly sensitive, specific and rapid method for DNA amplification at a constant temperature (60-65° C.) (Nagamine, 2002; Tomita 2008; Nagamine 2002; Mair 2013; Tanner 2012) LAMP can achieve $10^9$-fold amplification within one hour, relying on auto-cycling strand displacement DNA synthesis. It is performed with a strand-displacing *Bacillus stearothermophilus* (Bst) DNA polymerase and four to six specially designed primers that enable the highly specific recognition of target DNA, generating amplicons that have a loop structure that can be utilized for sequence-specific signaling (Jiang 2015). LAMP has also proven useful for the detection of many infectious agents including disease-causing parasites and other pathogens (Suwancharoen 2016; Wang 2016; Abdulmawjood 2016; Song 2016; Kong 2016; Zhang 2016).

Although LAMP is a valuable tool for the detection of nucleic acids, LAMP's applicability would be remarkably improved if it could be performed at low temperatures. Working at low temperatures could improve detection of target variants by enabling mismatched (degenerate) primers to bind better. Additionally, it could reduce device complexity and power consumption when incorporated into portable devices that are useful for point of care applications. Reduced heating needs would mean less power consumption and hence less cost. Several isothermal amplification methods at low temperatures (around 40° C.) such as nucleic acid sequence-based amplification (NASBA), strand displacement amplification (SDA), rolling circle amplification (RCA), helicase-dependent amplification (HDA) and recombinase polymerase amplification (RPA) have been reported. However, those methods require additional steps or enzymes and show relatively low specificity with only two primers, while LAMP is performed by only one enzyme with a high specificity derived from four to six primers. What is needed in the art is a version of LAMP which works at lower temperatures.

SUMMARY

Disclosed herein is a non-naturally occurring thermostable polymerase, wherein the thermostable polymerase is characterized by increased temperature stability in the range of 70° C. to 100° C., increased strand displacement capability, increased processivity, or a combination thereof compared with a wild type large fragment *Bacillus stearothermophilus* (Bst LF) polymerase.

Also disclosed herein is a method of identifying a non-naturally occurring thermostable polymerases, the method comprising: a) providing a pool of nucleic acids comprising nucleic acid members each encoding non-naturally occurring, potential thermostable polymerases; b) subdividing the pool of nucleic acid members into cellular compartments by transformation into a bacterial host, such that each cell comprises a nucleic acid member; c) expressing the nucleic acid member in the cell compartment to form a potential thermostable polymerase encoded by the nucleic acid member; d) subdividing the pool of bacterial cells into compartments, such that each compartment contains a single cell with a single nucleic acid member and encoded polymerase e) subjecting the pool of nucleic acid members to thermal denaturation and isothermal amplification conditions, such that the nucleic acid member may be processed by the a thermostable polymerase encoded by said nucleic acid member; and f) detecting processing of the nucleic acid member by a thermostable polymerase encoded by said nucleic acid member, thereby identifying a thermostable polymerase.

Further disclosed herein is a method of amplifying a nucleic acid, the method comprising exposing a target nucleic acid to a buffer solution with a polymerase and at least four primers, wherein at least one of the four primers comprises a phosphorothioated nucleotide; and amplifying the target nucleic acid using an isothermal amplification reaction, wherein the isothermal amplification reaction produces at least one loop product, wherein at least part of the single-stranded portion of the loop product represents the target nucleic acid.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 2 shows mock IsoCSR selection with wild-type Bst LF. The IsoCSR selection was initially optimized using wild-type Bst LF and BstXX, an inactive variant with 6 stop codons and a unique EcoRI restriction site. BL21 cells carrying plasmids encoding either polymerase were cultured with increasing ratios of inactive BstXX:Bst LF, then subjected to mesothermophilic IsoCSR to accommodate BstLF (see FIG. 1a). Following 2 rounds of recovery PCR (20 cycles each), products were digested with EcoRI to distinguish Bst LF from BstXX and analyzed with gel electrophoresis.

FIG. 3 shows isothermal screening of evolved variants. LAMP activity of two functional variants isolated from IsoCSR compared to Bst LF (A). LAMP activity after heating fully assembled LAMP reactions for 1 min at a range of temperatures (B). Solid and dashed lines indicate the temperature at which the reaction was heated prior to LAMP.

FIG. 6 shows structural characteristics of chimeric variant 5.9. The crystal structure alignment of wild-type Bst LF and Klentaq is pictured (A). The polymerase domain consists of 3 subdomains, termed the fingers, palm, and thumb. The I and H helix of the thumb subdomain form an essential coiled-coil structure. Variant 5.9 consists of the Klentaq protein sequence with 13 mutations (B), largely comprising a Bst insertion located at the base of the thumb subdomain. This region is highly divergent between Klentaq and Bst LF. In Klentaq (C), the region is largely unstructured; the site of the Bst insertion (blue) contains only a small alpha helix (*) that is separated from the I helix by an unstructured loop. The nearby E322G mutation we observed in variant 5.9 is also pictured (red). In Bst (D), the inserted region (blue) is an extension of the I helix, and contains a beta strand that is part of a small, antiparallel beta sheet (three black arrows) not present in the Klentaq structure.

FIGS. 13 A-C show a melt curve analysis of RCA Reactions. RCA reactions were subjected to a melt curve analysis on the LightCycler 96 qPCR machine (Roche) following isothermal incubation for product specificity analysis. Letters correspond to data in FIG. 5. Linear RCA produces small melt curves that are similar between all products and correlate with amount of product (A). Results are similar for hyperbranched RCA from the relaxed, nicked plasmid template (B). The v5.9 no template control shows a different melt peak, indicating non-specific amplification, likely due to primer dimers. Variant 5.9 in the only polymerase able to produce exponential amplification from supercoiled plasmid template; this is indicated by the quantity and melt temperature of product (C). Bst LF produces a melt peak with reduced Tm, overlapping with a small peak in v5.9.

FIGS. 14 A-C show an in-emulsion cell lysis of E. coli cells expressing GFP using lysozyme. E. coli cells expressing GFP polymerase were emulsified using standard IsoCSR emulsion conditions (see Methods). Cells were incubated with or without Lysozyme for the times indicated, then imaged using an inverted fluorescent microscope. Cells show very little lysis at 4° C. even with lysozyme included for up to 1 hour incubations, as indicated by the tightly confined GFP signal (FIGS. 14A and 14B, respectively). After digestion with lysozyme for 30 min at 37° C. followed by 30 min at 65° C. (simulating isothermal incubation), cells have been completely lysed, as indicated by GFP occupying the entirety of each emulsion compartment (FIG. 14C).

FIG. 15 shows emulsion size stability after incubation at 65° C. Emulsions were assembled as previously indicated with either 1× or 2× aqueous component volume, emulsified using a TissueLyser (Qiagen) with the indicated Hz settings for 4 min, and subjected to incubations at 65° C. in order to simulate isothermal amplification conditions. Compartment sizes were calculated as pixel area using MATLAB software (MathWorks). While the smaller emulsions generated by 42 Hz emulsification appeared stable for up to 6 hr, emulsifications at either frequency were stable for 3 hrs. 35 Hz emulsions had a larger average and maximum size after 3 hr incubations, indicating that these larger compartments are stable.

FIGS. 17 A-C show a comparison of R-LAMP and PS-LAMP with different temperatures. (a) Under the same buffer condition, R-LAMP and PS-LAMP were performed with different temperatures (line 1: no template/R-LAMP/65° C., line 2: $1.2 \times 10^8$ copies of template/R-LAMP/65° C., line 3: no template/PS-LAMP/65° C., line 4: $1.2 \times 10^8$ copies of template/PS-LAMP/65° C., line 5: no template/R-LAMP/60° C., line 6: $1.2 \times 10^8$ copies of template/R-LAMP/60° C., line 7: no template/PS-LAMP/60° C., line 8: $1.2 \times 10^8$ copies of template/PS-LAMP/60° C.). (b) Fluorescence intensities at a 50 cycle for R-LAMP and PS-LAMP with a 500 pg of template were compared according to different temperatures. (c) At 45° C., R-LAMP with a normal buffer and PS-LAMP with a semi-optimized buffer (12 U of Bst 2.0 DNA polymerase, 0.5 µg of ET SSB and 2 mM of $MgSO_4$) were performed.

FIGS. 18 A-D show the effects of urea and Bst 2.0 DNA polymerase. Fluorescence intensities were monitored with different concentrations of urea (line 1: 0 M/no template, line 2: 0 M/$1.2 \times 10^8$ copies of template, line 3: 0.48 M/no template, line 4: 0.48 M/$1.2 \times 10^8$ copies of template, line 5: 0.96 M/no template, line 6: 0.96 M/$1.2 \times 10^8$ copies of template, line 7: 1.2 M/no template, line 8: 1.2 M/$1.2 \times 10^8$ copies of template, line 9: 1.44 M/no template, line 10: 1.44 M/$1.2 \times 10^8$ copies of template) (a) and units of Bst 2.0 DNA polymerase (line 1: 20 U/no template, line 2: 20 U/$1.2 \times 10^8$ copies of template, line 3: 40 U/no template, line 4: 40 U/$1.2 \times 10^8$ copies of template, line 5: 60 U/no template, line 6: 60 U/$1.2 \times 10^8$ copies of template, line 7: 80 U/no template, line 8: 80 U/$1.2 \times 10^8$ copies of template, line 9: 120 U/no template, line 10: 120 U/$1.2 \times 10^8$ copies of template) (c) during PS-LAMP at 40° C. Cq values were plotted with the concentrations of urea (b) and units of Bst 2.0 DNA polymerase (d).

FIGS. 19 A-D show the effects of ET SSB and $MgSO_4$. Fluorescence intensities were monitored with different amounts of ET SSB (line 1: 0 µg/no template, line 2: 0 µg/$1.2 \times 10^8$ copies of template, line 3: 0.25 µg/no template, line 4: 0.25 µg/$1.2 \times 10^8$ copies of template, line 5: 0.5 µg/no template, line 6: 0.5 µg/$1.2 \times 10^8$ copies of template, line 7: 0.75 µg/no template, line 8: 0.75 µg/$1.2 \times 10^8$ copies of template) (a) and concentrations of $MgSO_4$ (line 1: 0.5 mM/no template, line 2: 0.5 mM/$1.2 \times 10^8$ copies of template, line 3: 1 mM/no template, line 4: 1 mM/$1.2 \times 10^8$ copies of template, line 5: 1.5 mM/no template, line 6: 1.5 mM/$1.2 \times 10^8$ copies of template, line 7: 2 mM/no template, line 8: 2 mM/$1.2 \times 10^8$ copies of template, line 9: 2.5 mM/no template, line 10: 2.5 mM/$1.2 \times 10^8$ copies of template) (c) during PS-LAMP at 40° C. Cq values were plotted with the amounts of ET SSB (b) and concentrations of $MgSO_4$ (d).

FIGS. 20 A-D show quantitative analysis of PS-LAMP for different templates. The fluorescence intensities were monitored for PS-LAMP at 40° C. (a, c) and R-LAMP at 65° C. (b, d) with titrated mers1b (a, b) and mers1a (c, d) plasmids.

FIGS. 22A-F show the effects of ET SSB, Bst 2.0 DNA polymerase and $MgSO_4$ on PS-LAMP at 45° C. for MERS 1b. Fluorescence intensities were monitored with different amounts of ET SSB (line 1: 0 µg/no template, line 2: 0 µg/1.2×10$^8$ copies of template, line 3: 0.5 µg/no template, line 4: 0.5 µg/1.2×10$^8$ copies of template, line 5: 1 µg/no template, line 6: 1 µg/1.2×10$^8$ copies of template, line 7: 2 µg/no template, line 8: 2 µg/1.2×10$^8$ copies of template) (a), Bst 2.0 DNA polymerase (line 1: 12 U/no template, line 2: 12 U/1.2×10$^8$ copies of template, line 3: 16 U/no template, line 4: 16 U/1.2×10$^8$ copies of template, line 5: 20 U/no template, line 6: 20 U/1.2×10$^8$ copies of template, line 7: 24 U/no template, line 8: 24 U/1.2×10$^8$ copies of template) (c) and $MgSO_4$ (line 1: 0 mM/no template, line 2: 0 mM/1.2×10$^8$ copies of template, line 3: 1 mM/no template, line 4: 1 mM/1.2×10$^8$ copies of template, line 5: 2 mM/no template, line 6: 2 mM/1.2×10$^8$ copies of template, line 7: 3 mM/no template, line 8: 3 mM/1.2×10$^8$ copies of template, line 9: 4 mM/no template, line 10: 4 mM/1.2×10$^8$ copies of template) (e) during PS-LAMP at 45° C. DT values were plotted with the amounts of ET SSB (b), Bst 2.0 DNA polymerase (d) and concentrations of $MgSO_4$ (f).

FIGS. 23 A-B show the effects of RecA. Fluorescence intensities were monitored with a ET SSB (line 1: 0.5 µg/no template, line 2: 0.5 µg/1.2×10$^8$ copies of template) as a control and different amounts of RecA (line 3: 1 µg/no template, line 4: 1 µg/1.2×10$^8$ copies of template, line 5: 2 µg/no template, line 6: 2 µg/1.2×10$^8$ copies of template, line 7: 3 µg/no template, line 8: 3 µg/1.2×10$^8$ copies of template, line 9: 4 µg/no template, line 10: 4 µg/1.2×10$^8$ copies of template) during PS-LAMP at 40° C. Cq values were plotted with the amounts of ET SSB and RecA (b). Experimental condition (urea: 1.44 M, Bst 2.0 DNA polymerase: 60 U, $MgSO_4$: 2 mM).

FIGS. 24A and 24B show PS-LAMP at different temperatures and effect of $MgSO_4$ for MERS 1b. Fluorescence intensities for PS-LAMP were monitored at different temperatures in the normal buffer (line 1: 45° C./no template, line 2: 45° C./1.2×10$^8$ copies of template, line 3: 50° C./no template, line 4: 50° C./1.2×10$^8$ copies of template, line 5: 55° C./no template, line 6: 55° C./1.2×10$^8$ copies of template, line 7: 60° C./no template, line 8: 60° C./1.2×10$^8$ copies of template) (a). At 45° C., various $MgSO_4$ concentrations were tested (line 1: 0 mM/no template, line 2: 0 mM/1.2×10$^8$ copies of template, line 3: 1 mM/no template, line 4: 1 mM/1.2×10$^8$ copies of template, line 5: 2 mM/no template, line 6: 2 mM/1.2×10$^8$ copies of template, line 7: 3 mM/no template, line 8: 3 mM/1.2×10$^8$ copies of template, line 9: 4 mM/no template, line 10: 4 mM/1.2×10$^8$ copies of template) in the buffer (8 U of Bst 2.0 DNA polymerase) (b).

FIG. 25 shows selectivity analysis of PS-LAMP for different types of non-complementary templates. PS-LAMP with primers specific to MERS 1b was performed for various templates (blank, MERS 1a, NRP2 and human gDNA) in absence/presence of MERS 1b and the fluorescence intensities of PS-LAMP were measured after 3 hours at 40° C. in the buffer (1.44 M of urea, 60 U of Bst 2.0 DNA polymerase, 0.5 µg of ET SSB and 2 mM of $MgSO_4$) after 3 hours. The concentration of MERS 1b, MERS 1a, NRP2 and human genomic DNA was 500 µg.

FIG. 26A-D show optimization of RTX polymerase. with 12 M Urea: (a) amplification mix, (b), amplification curve (c) and (d) formamide optimization for zika RNA amplification.

FIG. 27A-C shows final experimental protocol for zika NS5 PS LAMP. Real time data was collected using formamide at 8%. (a) shows protocol. (b) shows amplification curve. (c) shows picture of zika PS LAMP after 3 hour reaction under optimized condition. The LOD is 0.5 fg (~1000 copies).

DETAILED DESCRIPTION

Figure 1:
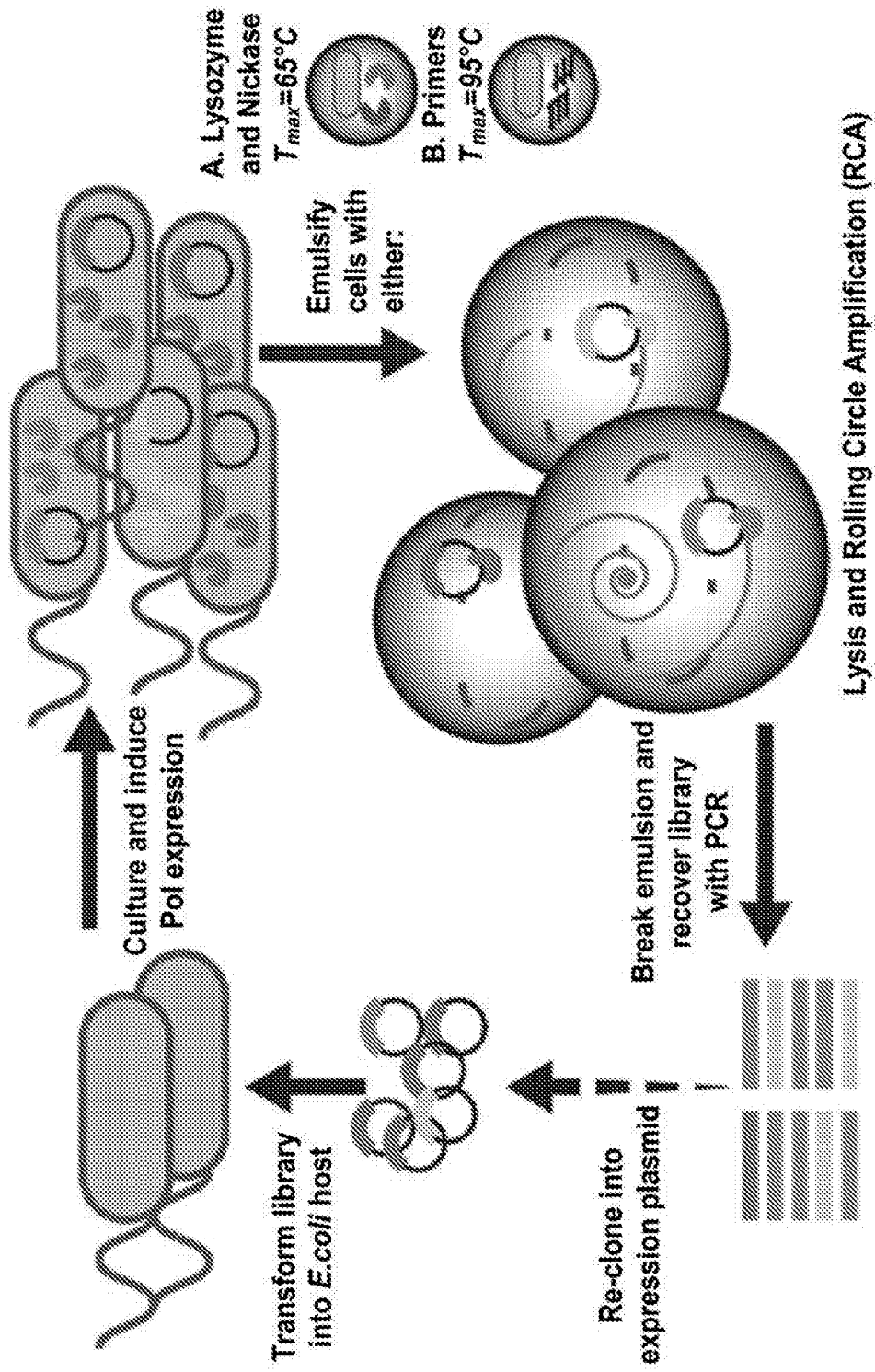
FIG. 1 shows an Isothermal CSR schematic. In IsoCSR, *E. coli* cells expressing a plasmid-encoded polymerase library are suspended in a water-in-oil emulsion with a single cell per compartment, preserving genotype-phenotype linkage. Each compartment contains either lysozyme and Nb.BsmI nickase for enzymatic lysis and RCA initiation in mesothermophilic IsoCSR (A) or primers for heat-initiated lysis and RCA in thermostable IsoCSR (B). Following lysis, functional polymerases replicate their own plasmid via isothermal Rolling Circle Amplification, which is dependent upon a polymerase having strong strand-displacing activity. The most active polymerases (green) produce more DNA, while less active variants (yellow) produce less; non-functional variants (red) produce none. After the hbRCA reaction, emulsions are broken, DNA is pooled, and the library is recovered by PCR, enriched for functional variants by the positive feedback loop in emulsio. The library can be further recloned into the expression vector for subsequent rounds as needed.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

A "self-assembly pathway" is a series of reactions autonomously executed by nucleic acid sequences in the execution of hybridized, detectable nucleic acid sequences. The self-assembly pathway comprises assembly, or hybridization, of nucleic acid sequences. In some embodiments, the self-assembly pathway can also comprise one or more disassembly reactions.

The term "nucleic acid" refers to natural nucleic acids, artificial nucleic acids, analogs thereof, or combinations thereof. Nucleic acids may also include analogs of DNA or RNA having modifications to either the bases or the backbone. For example, nucleic acid, as used herein, includes the use of peptide nucleic acids (PNA). The term "nucleic acids" also includes chimeric molecules.

The term "hairpin" as used herein refers to a structure formed by intramolecular base pairing in a single-stranded polynucleotide ending in an unpaired loop (the "hairpin loop"). In various embodiments, hairpins comprise a hairpin loop protected by stems. For example, a hairpin can comprise a first stem region, a hairpin loop region, and a second stem region. The first and second stem regions can hybridize to each other and together form a duplex region. Thus, a stem region of a hairpin nucleic acid is a region that hybridizes to a complementary portion of the same nucleic acid to form the duplex stem of a hairpin.

the term "hairpin loop" refers to a single stranded region that loops back on itself and is closed by a single base pair.

"Interior loop" and "internal loop," are used interchangeably and refer to a loop closed by two base pairs. The closing base pairs are separate by single stranded regions of zero or more bases. A "bulge loop" is an interior loop where one of the separated single-stranded regions is zero bases in length and the other is greater than zero bases in length.

An "initiator" is a molecule that is able to initiate the hybridization of two other nucleic acid sequences. The initiator is also referred to herein as the third nucleic acid sequence, while it facilitates the hybridization of what is referred to herein as the first and second nucleic acid sequences.

"Monomers" as used herein refers to individual nucleic acid sequences. For example, monomers are referred to herein as a first nucleic acid sequence, a second nucleic acid sequence, or a third nucleic acid sequence, etc.

By "nucleic acid sequence" is meant a nucleic acid which comprises an individual sequence. When a first, second, or third nucleic acid sequence is referred to, this is meant that the individual nucleotides of each of the first, second, third, etc., nucleic acid sequence are unique and differ from each other. In other words, the first nucleic acid sequence will differ in nucleotide sequences from the second and third, etc. There can be multiple nucleic acid sequences with the same sequence. For instance, when a "first nucleic acid sequence" is referred to, this can include multiple copies of the same sequence, all of which are referred to as a "first nucleic acid sequence."

Typically, at least two different nucleic acid sequences are used in self-assembly pathways, although three, four, five, six or more may be used. Typically each nucleic acid sequence comprises at least one domain that is complementary to at least a portion of one other sequence being used for the self-assembly pathway. Individual nucleic acid sequences are discussed in more detail below.

The term "domain" refers to a portion of a nucleic acid or protein sequence. An "input domain" of a nucleic acid or protein sequence refers to a domain that is configured to receive a signal which initiates a physical and/or chemical change, such as, a for example, a conformational change, of the nucleic acid sequence. In some embodiments, an input domain can be an initiator binding domain, an assembly complement domain, or a disassembly complement domain. An "output domain" of a nucleic acid sequence refers to a domain that is configured to confer a signal. For example, the signal can bind a complementary sequence to an input domain. In some embodiments, an output domain is configured to confer a signal to an input domain of another nucleic acid sequence. In some embodiments, an output domain can be, for example, an assembly domain, or a disassembly domain. In some embodiments, an output domain can be present in an initiator.

The term "nucleate" as used herein means to begin a process of, for example, a physical and/or chemical change at a discrete point in a system. The term "nucleation" refers to the beginning of physical and/or chemical changes at discrete points in a system.

A "propagation region" as used herein refers to a portion of a domain of a first nucleic acid sequence that is configured to hybridize to a complementary second nucleic acid sequence once the toehold of the domain nucleates at an exposed toehold of the second nucleic acid sequence. The propagation region is configured such that an available secondary nucleic acid sequence does not nucleate at the propagation region; rather, the propagation region hybridizes to the second nucleic acid sequence only after nucleation at the toehold of the same domain.

In some embodiments, nucleic acid sequences can be "metastable." That is, in the absence of an initiator they are kinetically disfavored from associating with other nucleic acid sequences comprising complementary regions.

As used herein, the terms "polymerization" and "assembly" are used interchangeably and refer to the association of two or more nucleic acid sequence, or one or more nucleic acid sequences and an initiator, to form a polymer. The "polymer" may comprise covalent bonds, non-covalent bonds or both. For example, in some embodiments a first, second, and third nucleic acid sequence can hybridize sequentially to form a polymer comprising a three-arm branched junction.

As used herein term "disassembly" refers to the disassociation of an initiator or at least one nucleic acid sequence.

As used herein "reaction graph" refers to a representation of assembly (and, optionally, disassembly) pathways that can be translated into molecular executables.

As used herein the terms "flip" and "switch" are used interchangeably and refer to a change from one state (e.g., accessible) to another state (e.g., inaccessible).

"Kinetically trapped" means that the nucleic acid sequences are inaccessible. In other words, a nucleic acid sequence which is "kinetically trapped" is not available for hybridization. For example, a nucleic acid sequence which has formed a hairpin is considered to be kinetically trapped.

As used herein, an "aptamer" is an oligonucleotide that is able to specifically bind an analyte of interest other than by base pair hybridization. Aptamers typically comprise DNA or RNA or a mixture of DNA and RNA. Aptamers may be naturally occurring or made by synthetic or recombinant means. The aptamers are typically single stranded, but may also be double stranded or triple stranded. They may comprise naturally occurring nucleotides, nucleotides that have been modified in some way, such as by chemical modification, and unnatural bases, for example 2-aminopurine. See, for example, U.S. Pat. No. 5,840,867. The aptamers may be chemically modified, for example, by the addition of a label, such as a fluorophore, or by the addition of a molecule that allows the aptamer to be crosslinked to a molecule to which it is bound. Aptamers are of the same "type" if they have the same sequence or are capable of specific binding to the same molecule. The length of the aptamer will vary, but is typically less than about 100 nucleotides.

The term "oligonucleotides," or "oligos" as used herein refers to oligomers of natural (RNA or DNA) or modified nucleic acid sequences or linkages, including natural and unnatural deoxyribonucleotides, ribonucleotides, anomeric forms thereof, peptide nucleic acid monomers (PNAs), locked nucleotide acids monomers (LNA), and the like and/or combinations thereof, capable of specifically binding to a single-stranded polynucleotide by way of a regular pattern of sequence-to-sequence interactions, such as Watson-Crick type of base pairing, base stacking, Hoogsteen or reverse Hoogsteen types of base pairing, or the like. Usually nucleic acid sequences are linked by phosphodiester bonds or analogs thereof to form oligonucleotides ranging in size from a few base units, e.g., 8-12, to several tens of base units, e.g., 100-200. Suitable oligonucleotides may be prepared by the phosphoramidite method described by Beaucage and Carruthers (Tetrahedron Lett., 22, 1859-1862, 1981), or by the triester method according to Matteucci, et al. (J. Am. Chem. Soc., 103, 3185, 1981), both incorporated herein by reference, or by other chemical methods such as using a commercial automated oligonucleotide synthesizer. Oligonucleotides (both DNA and RNA) may also be synthesized enzymatically for instance by transcription or strand displacement amplification. Typically, oligonucleotides are single-stranded, but double-stranded or partially double-stranded oligos may also be used in certain embodiments of the invention. An "oligo pair" is a pair of oligos that specifically bind to one another (i.e., are complementary (e.g., perfectly complementary) to one another).

The terms "complementary" and "complementarity" refer to oligonucleotides related by base-pairing rules. Complementary nucleotides are, generally, A and T (or A and U), or C and G. For example, for the sequence "5'-AGT-3'," the perfectly complementary sequence is "3'-TCA-5'." Methods for calculating the level of complementarity between two nucleic acids are widely known to those of ordinary skill in the art. For example, complementarity may be computed using online resources, such as, e.g., the NCBI BLAST website (ncbi.nlm.nih.gov/blast/producttable.shtml) and the Oligonucleotides Properties Calculator on the Northwestern University website (basic.northwestern.edu/biotools/oligo-calc.html). Two single-stranded RNA or DNA molecules may be considered substantially complementary when the nucleotides of one strand, optimally aligned and with appropriate nucleotide insertions or deletions, pair with at least about 80% of the nucleotides of the other strand, usually at least about 90% to 95%, and more preferably from about 98 to 100%. Two single-stranded oligonucleotides are considered perfectly complementary when the nucleotides of one strand, optimally aligned and with appropriate nucleotide insertions or deletions, pair with 100% of the nucleotides of the other strand. Alternatively, substantial complementarity exists when a first oligonucleotide will hybridize under selective hybridization conditions to a second oligonucleotide. Selective hybridization conditions include, but are not limited to, stringent hybridization conditions. Selective hybridization, or substantially complementary hybridization, occurs when at least about 65% of the nucleic acid sequences within a first oligonucleotide over a stretch of at least 14 to 25 sequences pair with a perfectly complementary sequences within a second oligonucleotide, preferably at least about 75%, more preferably at least about 90%. Preferably, the two nucleic acid sequences have at least 95%, 96%, 97%, 98%, 99% or 100% of sequence identity. See, M. Kanehisa, Nucleic Acids Res. 12, 203 (1984), incorporated herein by reference. For shorter nucleotide sequences selective hybridization occurs when at least about 65% of the nucleic acid sequences within a first oligonucleotide over a stretch of at least 8 to 12 nucleotides pair with a perfectly complementary nucleic acid sequence within a second oligonucleotide, preferably at least about 75%, more preferably at least about 90%. Stringent hybridization conditions will typically include salt concentrations of less than about 1 M, more usually less than about 500 mM and preferably less than about 200 mM. Hybridization temperatures can be as low as 5° C., and are preferably lower than about 30° C. However, longer fragments may require higher hybridization temperatures for specific hybridization. Hybridization temperatures are generally at least about 2° C. to 6° C. lower than melting temperatures ($T_m$), which are defined below.

As used herein, "two perfectly matched nucleotide sequences" refers to a nucleic acid duplex wherein the two nucleotide strands match according to the Watson-Crick basepair principle, i.e., A-T and C-G pairs in DNA:DNA duplex and A-U and C-G pairs in DNA:RNA or RNA:RNA duplex, and there is no deletion or addition in each of the two strands.

The term, "mismatch" refers to a nucleic acid duplex wherein at least one of the nucleotide base pairs do not form a match according to the Watson-Crick basepair principle. For example, A-C or U-G "pairs" are lined up, which are not capable of forming a basepair. The mismatch can be in a single set of bases, or in two, three, four, five, or more basepairs of the nucleic acid duplex.

As used herein, "complementary to each other over at least a portion of their sequence" means that at least two or more consecutive nucleotide base pairs are complementary to each other. For example, 3, 4, 5, 6, 7, 8, 9, 10, 11, 12, 13, 14, 15, 16, 17, 18, 19, 20, 21, 22, 23, 24, 25, 26, 27, 28, 29, 30, or more consecutive nucleotide base pairs can be complementary to each other over the length of the nucleic acid sequence.

As used herein, "substantially hybridized" refers to the conditions under which a stable duplex is formed between two nucleic acid sequences, and can be detected. This is discussed in more detail below.

As used herein, a "significant reduction in background hybridization" means that non-specific hybridization, or hybridization between unintended nucleic acid sequences, is reduced by at least 80%, more preferably by at least 90%, even more preferably by at least 95%, still more preferably by at least 99%.

By "preferentially binds" it is meant that a specific binding event between a first and second molecule occurs at least 20 times or more, preferably 50 times or more, more preferably 100 times or more, and even 1000 times or more often than a nonspecific binding event between the first molecule and a molecule that is not the second molecule. For example, a capture moiety can be designed to preferentially bind to a given target agent at least 20 times or more, preferably 50 times or more, more preferably 100 times or more, and even 1000 times or more often than to other molecules in a biological solution. Also, an immobilized binding partner, in certain embodiments, will preferentially bind to a target agent, capture moiety, or capture moiety/target agent complex. While not wishing to be limited by applicants present understanding of the invention, it is believed binding will be recognized as existing when the $K_a$ is at $10^7$ l/mole or greater, preferably $10^8$ l/mole or greater. In the embodiment where the capture moiety is comprised of antibody, the binding affinity of $10^7$ l/mole or more may be due to (1) a single monoclonal antibody (e.g., large numbers of one kind of antibody) or (2) a plurality of different monoclonal antibodies (e.g., large numbers of each of several different monoclonal antibodies) or (3) large numbers of polyclonal antibodies. It is also possible to use combinations of (1)-(3). The differential in binding affinity may be accomplished by using several different antibodies as per (1)-(3) above and as such some of the antibodies in a mixture could have less than a four-fold difference. For purposes of most embodiments of the invention an indication that no binding occurs means that the equilibrium or affinity constant $K_a$ is $10^6$ l/mole or less. Antibodies may be designed to maximize binding to the intended antigen by designing peptides to specific epitopes that are more accessible to binding, as can be predicted by one skilled in the art.

The term "sample" in the present specification and claims is used in its broadest sense and can be, by non-limiting example, any sample that is suspected of containing a target agent(s) to be detected. It is meant to include specimens or cultures (e.g., microbiological cultures), and biological and environmental specimens as well as non-biological specimens. Biological samples may comprise animal-derived materials, including fluid (e.g., blood, saliva, urine, lymph, etc.), solid (e.g., stool) or tissue (e.g., buccal, organ-specific, skin, etc.), as well as liquid and solid food and feed products and ingredients such as dairy items, vegetables, meat and meat by-products, and waste. Biological samples may be obtained from, e.g., humans, any domestic or wild animals, plants, bacteria or other microorganisms, etc. Environmental samples can include environmental material such as surface matter, soil, water (e.g., contaminated water), air and industrial samples, as well as samples obtained from food and dairy processing instruments, apparatus, equipment, utensils, disposable and non-disposable items. These examples are not to be construed as limiting the sample types applicable to the present invention. Those of skill in the art would appreciate and understand the particular type of sample required for the detection of particular target agents (Pawliszyn, J., *Sampling and Sample Preparation for Field and Laboratory*, (2002); Venkatesh Iyengar, G., et al., *Element Analysis of Biological Samples: Principles and Practices* (1998); Drielak, S., *Hot Zone Forensics: Chemical, Biological, and Radiological Evidence Collection* (2004); and Nielsen, D. M., *Practical Handbook of Environmental Site Characterization and Ground-Water Monitoring* (2005)).

A substance is commonly said to be present in "excess" or "molar excess" relative to another component if that component is present at a higher molar concentration than the other component. Often, when present in excess, the component will be present in at least a 10-fold molar excess and commonly at 100-1,000,000 fold molar excess. Those of skill in the art would appreciate and understand the particular degree or amount of excess preferred for any particular reaction or reaction conditions. Such excess is often empirically determined and/or optimized for a particular reaction or reaction conditions.

As used herein, "a promoter, a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated.

As used herein, "operatively linked or operationally associated" refers to the functional relationship of nucleic acids with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, J. Biol. Chem., 266: 19867-19870 (1991)) can be inserted immediately 5' of the start codon and may enhance expression. The desirability of (or need for) such modification may be empirically determined.

As used herein, "RNA polymerase" refers to an enzyme that synthesizes RNA using a DNA or RNA as the template. It is intended to encompass any RNA polymerase with conservative amino acid substitutions that do not substantially alter its activity.

As used herein, "reverse transcriptase" refers to an enzyme that synthesizes DNA using a RNA as the template. It is intended to encompass any reverse transcriptase with conservative amino acid substitutions that do not substantially alter its activity.

"Enzymatically produced" refers to the production or secondary or tertiary folding of a nucleic acid by an enzyme rather than by chemical synthesis. Enzymatically produced nucleic acids can be made in vitro or in vivo. For example, ribozyme-containing transcription template scaffolds can be engineered to enable enzymatic co-transcriptional synthesis of RNA circuits that can operate without any post-synthetic separation and re-folding of individual circuit components.

B. SYSTEMS, METHODS, AND DEVICES

Disclosed herein are systems and methods, as well as the components to be used to prepare the disclosed systems, devices, and methods. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular nucleic acid sequence is disclosed and discussed and a number of modifications that can be made to a number of molecules including the nucleic acid sequence are discussed, specifically contemplated is each and every combination and permutation of the nucleic acid sequence and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

1. Thermophilic Strand-Displacing Polymerase

Strand-displacing polymerases are a crucial component of isothermal amplification (IA) reactions, DNA amplification techniques that, unlike PCR, don't require thermal cycling. Because they simplify equipment needs and are often faster and less prone to inhibition than PCR, these techniques are appealing for nucleic acid-based point of care detection. While pre-reaction heating is useful in isothermal amplification (IA) for cell lysis, contaminant denaturation, and template denaturation for improved primer binding, there is currently no thermostable polymerase demonstrated for multiple IA mechanisms that can survive these high temperatures, complicating point of care workflow. Additionally, polymerase engineering of strand-displacing polymerases has been limited to in silico approaches due to the inherent challenges in evolving mesophilic polymerases and selecting for strand displacement.

Disclosed herein is isothermal compartmentalized self-replication (IsoCSR), an isothermal emulsion-based directed evolution method analogous to CSR. Using an algorithm-optimized shuffled library of exonuclease-deficient polymerases from *Geobacillus stearothermophilus* (Bst LF) and *Thermus aquaticus* (Klentaq), IsoCSR was demonstrated by evolving a thermostable strand-displacing polymerase capable of high temperature IA methods like loop-mediated isothermal amplification and rolling circle amplification (LAMP and RCA), even after incubation at temperatures as high as 95° C. The polymerase outperforms Bst LF polymerase, the high temperature isothermal polymerase of choice, in RCA and performs similarly in LAMP reactions. IsoCSR is essential for evolving other useful characteristics for point of care applications, such as enhanced inhibitor tolerance in unprocessed samples.

Although Bst LF works at higher temperatures, it is not truly thermostable at temperatures that may be required for DNA denaturation and 'hot start' LAMP. There have been reports of two thermostable polymerases that could potentially be included in a denaturation step in IA reactions such as LAMP: OmniAmp, a viral polymerase from PyroPhage 3173 with DNA polymerase and reverse transcriptase activities (Chander 2014), and SD Polymerase, a mutant of the well-known *Thermus aquaticus* (Taq) polymerase (Ignatov 2014). However, neither of these polymerases have been validated for hot start LAMP, either due to the lack of sufficient thermostability to survive denaturation steps (OmniAmp), or insufficient strand displacement activity for LAMP (SD Polymerase).

Directed polymerase evolution using compartmentalized self-replication (CSR) and other methods have previously been used to identify sequence variants of DNA and RNA polymerases that have altered phenotypes such as increased thermostability, incorporation of unnatural or modified bases, reverse transcription, orthogonal promoter recognition, and resistance to enzymatic inhibitors (Ghadessy 2001; Baar 2011; Chen 2014; Meyer 2015; Ellefson 2016). Recently, an isothermal CSR selection was used to evolve the phi29 polymerase, but this selection required cumbersome freezing and thawing cycles for cell lysis that may limit the acquisition of thermostability or other novel phenotypes. In addition, the use of random primers resulted in off-target *E. coli* genome amplification, limiting the selection's utility and efficiency (Povilaitis 2016). A more robust isothermal compartmentalized self-replication (IsoCSR) method has been developed for engineering thermostable strand-displacing polymerases. IsoCSR retains the emulsion-based linkage of genotype and phenotype that was established in thermal cycling CSR, but replaces the in emulsio PCR step with hyperbranched rolling circle amplification (hbRCA) of supercoiled plasmid DNA. This innovation necessitates that a polymerase have excellent strand displacement activity in order to self-amplify its gene.

IsoCSR was used to combine the robust strand displacement capability of Bst LF with the extreme thermostability found in Klentaq. These distantly related enzymes were recoded to ensure maximal overlap, a shuffled library was created, and a thermostable chimeric polymerase was selected that enabled one pot, hot start LAMP. Strand displacement seemed to arise from a relatively short Bst insertion into a Klentaq backbone that can stabilize the 'thumb' domain common to DNA polymerases.

Therefore, disclosed herein is a non-naturally occurring thermostable polymerase, wherein thermostable polymerase is characterized by increased temperature stability in the range of 70° C. to 100° C., increased strand displacement capability, increased processivity, or a combination thereof compared with a wild type large fragment *Bacillus stearothermophilus* (Bst LF) polymerase. The polymerase is also more thermostable than Bst 2.0. The polymerase is capable of both isothermal amplification, such as LAMP and hyperbranched rolling circle amplification (RCA) from supercoiled plasmids without the use of nicking endonucleases. It is also useful with strand displacement amplification (SDA), polymerase spiral reaction (PSR), or helicase dependent amplification (HDA). The polymerase can also be capable of replicating DNA in a polymerase chain reaction (PCR).

By "increased temperature stability" is meant that the polymerase is 2, 3, 4, 5, 6, 7, 8, 9, 10, or 100 ore more times stable at the range of 70 to 100° C. than other polymerases. By "increased strand displacement capability" is meant that the polymerase disclosed herein is 10, 20, 30, 40, 50, 60, 70, 80, 90, or 100% or more capable of strand displacement than other polymerases. By "increased processivity" is meant that the polymerase disclosed herein is 10, 20, 30, 40, 50, 60, 70, 80, 90, or 100% or more processive than other polymerases.

The thermostable polymerase disclosed herein can be heated to above 60, 65, 70, 75, 80, 85, 90, 95, or 100° C. or higher without significant denaturation. Amplification can also occur at elevated temperatures, such as above 65° C.

As described in Example 1, the thermostable polymerase can comprise sequences from at least Bst LF and Klentaq polymerase. For example, disclosed is a polymerase which is 90, 91, 92, 93, 94, 95, 96, 97, or 99% or more identical to SEQ ID NO: 1. Also disclosed is a nucleic acid encoding SEQ ID NO: 1. For example, disclosed herein is the nucleic acid of SEQ ID NO: 2, which encodes a thermostable polymerase. This specific thermostable polymerase is referred to herein as v5.9. Also disclosed is a host cell comprising the nucleic acid encoding the polymerase disclosed herein.

The thermostable polymerase disclosed herein can be stored in a storage buffer, or a reaction buffer. For example, the buffer can comprise a temperature dependent inhibitor of polymerase activity. The polymerase can substantially lack 3' to 5' exonuclease activity.

Also disclosed herein is a method of identifying a non-naturally occurring thermostable polymerases, the method comprising: a) providing a pool of nucleic acids comprising nucleic acid members each encoding non-naturally occurring, potential thermostable polymerases; b) subdividing the pool of nucleic acid members into cellular compartments by transformation into a bacterial host, such that each cell comprises a nucleic acid member; c) expressing the nucleic acid member in the cell compartment to form a potential thermostable polymerase encoded by the nucleic acid member; d) subdividing the pool of bacterial cells into compartments, such that each compartment contains a single cell with a single nucleic acid member and encoded polymerase e) subjecting the pool of nucleic acid members to thermal denaturation and isothermal amplification conditions, such that the nucleic acid member may be processed by the a thermostable polymerase encoded by said nucleic acid member; and f) detecting processing of the nucleic acid member by a thermostable polymerase encoded by said nucleic acid member, thereby identifying a thermostable polymerase.

The pool of nucleic acids can be created by gene shuffling, error-prone PCR, or site-saturation mutagenesis. For example, gene shuffling can take place with nucleic acid encoding one or more known polymerases. This can be seen in Example 1. The polymerases can include, but are not limited to, Bst LF and Klentaq, for example. Thermal denaturation can take place at 65, 70, 75, 80, 85, 90, 95, or 100° C. or higher.

The isothermal amplification to which the polymerase can be subjected can be, but is not limited to, hyperbranched rolling circle amplification, recombinase polymerase amplification, or loop-mediated isothermal amplification. Amplification can also be by polymerase chain reaction (PCR). In one example, the contents of each compartment are not in contact with the contents of other compartments. The processing of the nucleic acid member can result in one copy of said nucleic acid member. The processing of the nucleic acid member can also result in more than one copy of said nucleic acid member. In one example, the number of copies of the nucleic acid member can be proportional to the activity of the thermostable polymerase.

Processing of nucleic acids can be detected by assaying the copy number of the nucleic acid member. For example, processing can be detected by assaying the presence of a tag on the nucleic acid member. Processing can also be detected by determining thermostable polymerase activity.

In one example, the step of expressing the nucleic acid member to form the thermostable polymerase encoded by said nucleic acid member can be carried out by in vitro transcription and translation. The step of expressing the nucleic acid member to form the thermostable polymerase encoded by said nucleic acid member can be carried out by in vivo transcription and translation in an expression host cell. The expression host cell can be a bacterial cell.

The compartments for carrying out the assay can comprise aqueous compartments of a water-in-oil emulsion. In one example, the non-aqueous portion of emulsion mix is 73% Tegosoft DEC, 7% AbilWE09, and 20% mineral oil. with an oil phase and a surfactant comprising Span80, Tween80, and TritonX100. The surfactant can comprise AbilWE09.

2. Isothermal Amplification Using Phosphorothioated Loop Mediated Isothermal Amplification (PS-LAMP)

Loop-mediated isothermal amplification (LAMP) is an extremely powerful tool for the detection of nucleic acids with high sensitivity and specificity. LAMP shows best performance at around 65° C., which is relatively high to be easily applied to point-of-care-testing (POCT). Disclosed herein is a phosphorothioated LAMP (PS-LAMP) working at low temperature by providing a more efficient amplification path. PS-modifications enabled efficient self-folding of the termini to generate more loops where intact inner primers bind and extend. By optimizing several factors such as urea, Bst 2.0 DNA polymerase, single-stranded DNA binding protein (SSB) and $MgSO_4$, comparable sensitivity and selectivity with a regular LAMP (R-LAMP) at 65° C. were achieved with a PS-LAMP at 40° C. As the novel PS-LAMP system is performed at around physiological temperature, it has a great potential in applications to hand-held or POCT diagnostic devices.

By incorporating the PS-THSP mechanism into a regular LAMP system, LAMP that performs well at low temperature has been made (Example 2). A phosphorothioate (PS) modification is incorporated into a part of inner primer's DNA backbone, leading to an increased self-folding of terminal hairpins. It can produce more loop sites where other inner primers can bind to and finally result in more efficient amplification. By optimizing conditions to accelerate the self-folding, the sensitivity of PS-LAMP at 40° C. was comparable with that of a regular LAMP at optimal temperature. The PS-modified DNA can also display enhanced stability against degradation by various nucleases that may be present in biological samples. As the novel PS-LAMP system is performed at around physiological temperature, it can be used in hand-held or point-of-care (POC) diagnostic devices.

Regarding LAMP in particular, it is a powerful isothermal nucleic acid amplification technique that can generate ~$10^9$ copies from less than 10 copies of template DNA within an hour or two. Unfortunately, while the amplification reactions are extremely powerful, quantitative detection of LAMP products has remained analytically challenging. LAMP can be conducted with two, three, four, five, or six primers, for example. OSD-LAMP can be used with 2 primers (FIP+BIP) and also 3 primers (FIP+BIP+F3 and FIP+BIP+B3). 2 as well as 3-primer OSD-LAMP assays can also be used The five primer LAMP system disclosed herein, and depicted in FIG. 1, is ultra-fast, sensitive, and a highly selective.

The 4-primer LAMP is the basic form of LAMP that was originally described for isothermal nucleic acid amplification. The system is composed of two loop-forming inner primers FIP and BIP and two outer primers F3 and B3 whose primary function is to displace the DNA strands initiated from the inner primers thus allowing formation of the loops and strand displacement DNA synthesis. Subsequently 6-primer LAMP was reported that incorporated 2 additional primers, LF and LB, that bind to the loop sequences located between the F1/F1c and F2/F2c priming sites and the B1/B1c and B2/B2c priming sites. Addition of both loop primers significantly accelerated LAMP. The 5-primer LAMP has been described herein, wherein the 4 LAMP primers (F3, B3, FIP and BIP) are used in conjunction with only one of the loop primers (either LF or LB). This allows the accelerated amplification afforded by the loop primer while using the other LAMP loop (not bound by the loop primer) for hybridization to loop-specific OSD probe. This innovation allows for high-speed LAMP operation while performing real-time sequence-specific signal transduction.

Therefore, disclosed herein is a method of using PS-LAMP comprising amplifying a nucleic acid, the method comprising exposing a target nucleic acid to a buffer solution comprising a polymerase and at least four primers, wherein at least one of the four primers comprises a phosphorothioated nucleotide; and amplifying the target nucleic acid using an isothermal amplification reaction, wherein the isothermal amplification reaction produces at least one loop product, wherein at least part of the single-stranded portion of the loop product represents the target nucleic acid.

In the PS-LAMP method disclosed herein, the loop product is exposed to a strand displacement reporter, wherein the strand displacement reporter comprises single-stranded and double-stranded nucleic acid, and further wherein a portion of the single-stranded nucleic acid of the strand displacement reporter is complementary to at least a portion of the single-stranded nucleic acid of the loop product representing the target nucleic acid, and allowing the loop product and the strand displacement reporter to interact, wherein interaction between the strand displacement reporter and the target nucleic acid portion of the loop product produces a detectable signal, wherein the signal indicates the presence of the target nucleic acid.

The isothermal amplification reaction can take place at 20, 25, 30, 35, 40, 45, 50, or 55° C. In one specific embodiment, the isothermal reaction can take place around 40° C.

The buffer can comprise various components which have been optimized for PS-LAMP. For example, urea can be present in the buffer at a concentration of 1.3-1.6 M, specifically 1.44 M. The buffer can also comprise a DNA polymerase, such as Bst, specifically Bst 2.0. Bst 2.0 can be present at a concentration of 35, 30, 45, 50, 55, 60, 65, or more units (U). The buffer can comprise $MgSO_4$. $MgSO_4$ can be present at a concentration of 1.0, 1.1. 1.2, 1.3, 1.4, 1.5, 1.6, 1.7, 1.8, 1.9, 2.0, 2.1, 2.2, 2.3, 2.4, or 2.5 or more mM. The buffer can also comprise a Single-Stranded Binding (SSB) protein. SSB can be present at a concentration of about 0.2 to 0.7 µg, for example about 0.5 µg. Specific examples of buffers can be found in Example 2.

In the method disclosed herein, the strand displacement reporter can be one step toehold displacement (OSD) reporter. The target nucleic acid can be RNA or DNA. Four, five, or six primers can be used with the isothermal amplification reaction.

Figure 16:
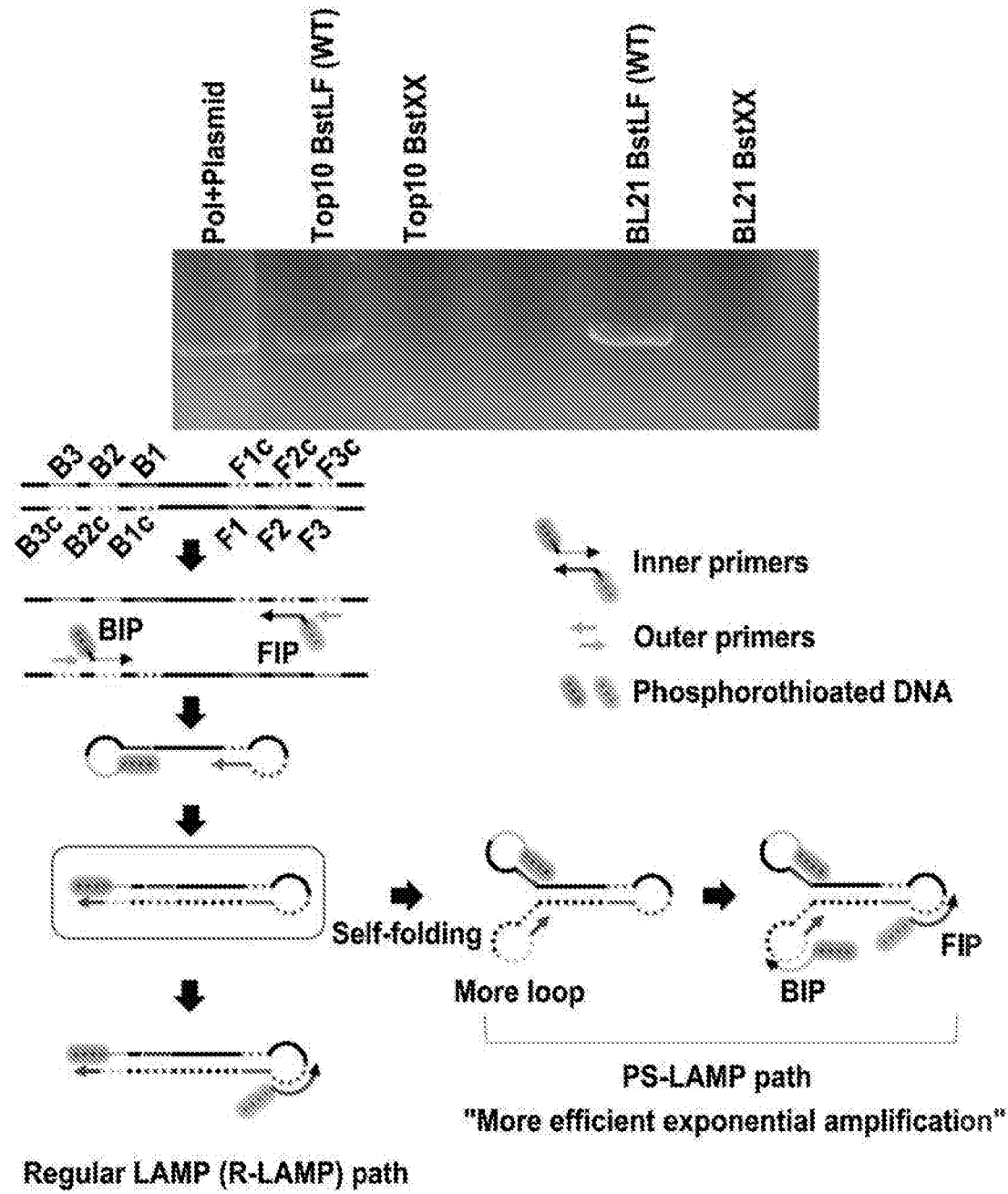
FIG. 16 shows a scheme of a phosphorothioated loop-mediated isothermal amplification (PS-LAMP).

FIG. 16 shows a reaction schematic for PS-LAMP. For example, the method can comprise using at least one forward inner primer (FIP), at least one backward inner primer (BIP), at least one forward outer primer (FOP), and at least one backward outer primer (BOP). At least one FIP comprises at least one phosphorothioated nucleotide. At least one BIP can comprise at least one phosphorothioated nucleotide. Both a FIP and a BIP can comprise at least one phosphorothioated nucleotide. For example, two or more nucleotides of at least one primer are phosphorothioated. 1, 2, 3, 4, 5, 6, 7, 8, 9, 10, 11, 12, 13, 14, 15, 16, 17, 18, 19, or 20 or more nucleotides of a primer can be phosphorothioated. The phosphorothioated nucleotides can be at either the N-terminal or the C-terminal of the primer.

Amplification of the target nucleic acid takes place in real time. Many examples of real-time amplification are known to those of skill in the art. One of skill in the art could therefore readily ascertain a real-time method for use with the invention disclosed herein.

Also disclosed is a method of diagnosing a subject with a disease, the method comprising carrying out the method of amplification described herein, wherein the presence of a target nucleic acid indicates the presence of a disease in the subject.

In one example, multiple target nucleic acids can be amplified simultaneously. The primers can bind a primer binding region of the target nucleic acid, as shown in FIG. 16. The method can take place in a single vessel, also referred to herein as "one pot" amplification.

Disclosed herein is a kit for amplifying nucleic acids, wherein the kit comprises DNA polymerase, and at least four distinct primers, wherein at least one of the primers is phosphorothioated. The kit can further comprise a buffer solution.

LAMP can be carried out using DNA or RNA (RT-LAMP). LAMP can amplify nucleic acids from a wide variety of samples. These include, but not limited to, bodily fluids (including, but not limited to, blood, urine, serum, lymph, saliva, anal and vaginal secretions, perspiration and semen, of virtually any organism, with mammalian samples being preferred and human samples being particularly preferred); environmental samples (including, but not limited to, air, agricultural, water and soil samples); plant materials; biological warfare agent samples; research samples (for example, the sample may be the product of an amplification reaction, for example general amplification of genomic DNA); purified samples, such as purified genomic DNA, RNA, proteins, etc.; raw samples (bacteria, virus, genomic DNA, etc.); as will be appreciated by those in the art, virtually any experimental manipulation may have been done on the sample. Specifically, it is noted that the polymerases disclosed herein can be used to amplify Zika Virus. Some embodiments utilize siRNA and microRNA as target sequences (Zhang et al., J Cell Physiol. (2007) 210(2):279-89; Osada et al., Carcinogenesis. (2007) 28(1):2-12; and Mattes et al., Am J Respir Cell Mol Biol. (2007) 36(1):8-12, each of which is incorporated herein by reference in its entirety).

Some embodiments utilize nucleic acid samples from stored (e.g. frozen and/or archived) or fresh tissues. Paraffin-embedded samples are of particular use in many embodiments, as these samples can be very useful, due to the presence of additional data associated with the samples, such as diagnosis and prognosis. Fixed and paraffin-embedded tissue samples as described herein refers to storable or archival tissue samples. Most patient-derived pathological samples are routinely fixed and paraffin-embedded to allow for histological analysis and subsequent archival storage.

The target analytes can be nucleic acids. A nucleic acid of the present invention, whether referring to the target nucleic acid or the strand displacement reporter, will generally contain phosphodiester bonds (for example in the case of the target sequences), although in some cases, nucleic acid analogs are included that may have alternate backbones, comprising, for example, phosphoramide (Beaucage et al. Tetrahedron (1993) 49(10):1925 and references therein; Letsinger, J. Org. Chem. (1970) 35:3800; Sprinzl et al., Eur. J. Biochem. (1977) 81:579; Letsinger et al., Nucl. Acids Res. (1986) 14:3487; Sawai et al, Chem. Lett. (1984) 805; Letsinger et al., J. Am. Chem. Soc. (1988) 110:4470; and Pauwels et al. Chemica Scripta (1986) 26:141), phosphorothioate (Mag et al., Nucleic Acids Res. (1991) 19:1437; and U.S. Pat. No. 5,644,048), phosphorodithioate (Briu et al., J. Am. Chem. Soc. (1989) 111:2321, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. (1992)114:1895; Meier et al., Chem. Int. Ed. Engl. (1992) 31:1008; Nielsen, Nature, (1993) 365:566; Carlsson et al., Nature (1996) 380:207, all of which are incorporated herein by reference in their entirety). Other analog nucleic acids include those with bicyclic structures including locked nucleic acids, Koshkin et al., J. Am. Chem. Soc. (1998) 120:13252 3); positive backbones (Denpcy et al., Proc. Natl. Acad. Sci. USA (1995) 92:6097; non-ionic backbones (U.S. Pat. Nos. 5,386,023. 5,637,684, 5,602,240, 5,216,141 and 4,469,863; Kiedrowshi et al., Angew. Chem. Intl. Ed. English (1991) 30:423; Letsinger et al. J. Am. Chem. Soc. (1988) 110:4470; Letsinger et al., Nucleoside & Nucleotide (1994) 13:1597; Chapters 2 and 3, ASC Symposium Series 580, Ed. Y. S. Sanghui and P. Dan Cook; Mesmaeker et al., Bioorganic & Medicinal Chem. Lett. (1994) 4:395; Jeffs et al., J. Biomolecular NMR (1994) 34:17; Xu et al., Tetrahedron Lett. (1996) 37:743) and non-ribose backbones, including those described in U.S. Pat. Nos. 5,235,033 and 5,034,506, and Chapters 6 and 7, ASC Symposium Series 580, Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are herein expressly incorporated by reference. These modifications of the ribose-phosphate backbone may be done to facilitate the addition of labels or other moieties, to increase or decrease the stability and half-life of such molecules in physiological environments, etc.

3. Uses

The methods, products, and devices disclosed herein can be used for multiple applications. Detection and identification of virtually any nucleic acid sequence, or non-nucleic acid sequence, can be accomplished. For example, the presence of specific viruses, microorganisms and parasites can be detected. For example, Zika Virus can be amplified. Genetic diseases can also be detected and diagnosed, either by detection of sequence variations (mutations) which cause or are associated with a disease or are linked (Restriction Fragment Length Polymorphisms or RFLP's) to the disease locus. Sequence variations which are associated with, or cause, cancer, can also be detected. This can allow for both the diagnosis and prognosis of disease. For example, if a breast cancer marker is detected in an individual, the individual can be made aware of their increased likelihood of developing breast cancer, and can be treated accordingly. The methods and devices disclosed herein can also be used in the detection and identification of nucleic acid sequences for forensic fingerprinting, tissue typing and for taxonomic purposes, namely the identification and speciation of microorganisms, flora and fauna.

The methods and devices disclosed herein have applications in clinical medicine, veterinary science, aquaculture, horticulture and agriculture. The methods and devices can also be used in maternity and paternity testing, fetal sex determination, and pregnancy tests.

4. Devices

Disclosed herein are devices for detection of a target nucleic acid, wherein the device comprises: a) an amplification unit, wherein said amplification unit amplifies the target nucleic acid via an isothermal amplification reaction); b) a transducer, wherein said transducer comprises strand displacement reporters, wherein said strand displacement reporters interact with the target nucleic acid amplification product of step a); and c) a signal output unit, which displays the detectable signal of step b).

The amplification unit is the portion of the device where amplification of a nucleic acid takes place. This can be via the LAMP methods disclosed herein, for example. The signal output unit detects the signal from the strand displacement reporter. The signal output unit can be part of a computer system, and the signal can be displayed on a monitor. The resulting signal can also be used in a computer processor to compare it to other results or databases, and the results can be displayed. Computer systems and computer readable media are discussed in more detail below.

The amplification unit, transducer, and signal output unit can be in a single device, and can be in fluid communication with each other. For example, amplification and detection can all take place in the same well of a microfluidics device. Furthermore, amplification and detection can take place simultaneously, and detection can occur in "real time."

The device can also comprise a heater. Because the amplification and detection reactions may require a temperature above room temperature, a heat source is contemplated herein. Heat sources may include, but are not limited to, contacting and non-contacting sources, as known in the art. In one embodiment, the heat source may comprise an optical heating device. For example, the optical device may comprise a defocused laser that is directed at an underside of the device. For example, heating may be achieved by using an 808 nm infra-red laser diode module (e.g., icetec-UK) operating at approximately 150 mW directed onto the device. The power of the laser may be controlled through an n-channel power MOSFET gated by a logic optocoupler driven by pulse width modulated (PWM) signal from a microcontroller (e.g., Fox LP3500, Rabbit Semiconductor, Davis, Calif.).

To provide temperature control, the controller may be programmed with a modified proportional-integral control routine using feedback from the pyrometer. The pyrometer feedback may be received by the microcontroller after a calibration correction is applied. To perform optical temperature detection, the sample may be illuminated obliquely, for example, by a high intensity light source having a selected wavelength. In one embodiment, the light source may comprise a blue light emitting diode (LED) that emits light at a wavelength selected within the range between about 450 nm to about 475 nm (e.g., approximately 470 nm). An example of an LED light source capable of this illumination is HLMP CB28 STD00, manufactured by Agilent Technologies, Santa Clara, Calif. Heating may also be achieved by other methods such as by chemical exothermic reactions or by using the computer's CPU-generated heat, or heating specific metals with batteries, etc.

5. Detection

Detection systems are known in the art, and include optical assays (including fluorescence and chemiluminescent assays), enzymatic assays, radiolabelling, surface plasmon resonance, magnetoresistance, cantilever deflection, surface plasmon resonance, etc. In some embodiments, OSD reporter can be used in additional assay technologies, for example, as described in 2006/0068378, hereby incorporated by reference, the OSD reporter can serve as a linker between light scattering particles such as colloids, resulting in a color change in the presence of the OSD reporter.

In some embodiments, the strand displacement reporters of the invention are attached to solid supports for detection. For example, strand displacement reporters can be attached to beads for subsequent analysis. Similarly, bead arrays as described below may be used.

In one embodiment, the present invention provides arrays, each array location comprising at a minimum a covalently attached strand displacement reporter, also referred to herein as a "capture probe". By "array" herein is meant a plurality of nucleic acid probes (OSD reporters, for example) in an array format; the size of the array will depend on the composition and end use of the array. Generally, the array will comprise from two to as many as 100,000 or more reporters, depending on the size of the electrodes, as well as the end use of the array. Preferred ranges are from about 2 to about 10,000, with from about 5 to about 1000 being preferred, and from about 10 to about 100 being particularly preferred. In some embodiments, the compositions of the invention may not be in array format; that is, for some embodiments, compositions comprising a single capture probe may be made as well. In addition, in some arrays, multiple substrates may be used, either of different or identical compositions. Thus, for example, large arrays may comprise a plurality of smaller substrates. Nucleic acids arrays are known in the art, and can be classified in a number of ways; both ordered arrays (e.g. the ability to resolve chemistries at discrete sites), and random arrays (e.g. bead arrays) are included. Ordered arrays include, but are not limited to, those made using photolithography techniques (Affymetrix GeneChip™), spotting techniques (Synteni and others), printing techniques (Hewlett Packard and Rosetta), origami pads, paperfluidics, electrode arrays, three dimensional "gel pad" arrays, etc. Liquid arrays may also be used.

By "substrate" or "solid support" or other grammatical equivalents herein is meant any material that can be modified to contain discrete individual sites appropriate for the attachment or association of nucleic acids. The substrate can comprise a wide variety of materials, as will be appreciated by those in the art. including, but not limited to glass, plastics, polymers, metals, metalloids, ceramics, organics, etc. When the solid support is a bead, a wide variety of substrates are possible, including magnetic materials, glass, silicon, dextrans, plastics, etc.

In another aspect of the invention, a fluidic is used to automate the methodology described in this invention. See for example U.S. Pat. No. 6,942,771, herein incorporated by reference for components including but not limited to cartridges, devices, pumps, wells, reaction chambers, and detection chambers.

The devices of the invention can comprise liquid handling components, including components for loading and unloading fluids at each station or sets of stations. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; holders with cartridges and/or caps; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

Chemically derivatized particles, plates, cartridges, tubes, magnetic particles, or other solid phase matrix with specificity to the assay components can also used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

Platforms for multi-well plates, multi-tubes, holders, cartridges, minitubes, deep-well plates, microfuge tubes, cryovials, square well plates, fitters, chips, optic fibers, beads, and other solid-phase matrices or platform with various volumes can be accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station.

Interchangeable pipet heads (single or multi-channel) with single or multiple magnetic probes, affinity probes, or pipetters robotically manipulate the liquid, particles, cells, and organisms can be used. Multi-well or multi-tube magnetic separators or platforms manipulate liquid, particles, cells, and organisms in single or multiple sample formats.

The instrumentation can include a detector, which can be a wide variety of different detectors, depending on the labels and assay. In a preferred embodiment, useful detectors include a microscope(s) with multiple channels of fluorescence; plate readers to provide fluorescent, electrochemical and/or electrical impedance analyzers, ultraviolet and visible spectrophotometry detection with single and dual wavelength endpoint and kinetics capability, fluoescence resonance energy transfer (FRET), luminescence, quenching, two-photon excitation, and intensity redistribution; CCD cameras to capture and transform data and images into quantifiable formats; and a computer workstation.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells. Flow cytometry or capillary electrophoresis formats can be used for individual capture of magnetic and other beads, particles, cells, and organisms.

The flexible hardware and software allow instrument adaptability for multiple applications. The software program modules allow creation, modification, and running of methods. The system diagnostic modules allow instrument alignment, correct connections, and motor operations. The customized tools, labware, and liquid, particle, cell and organism transfer patterns allow different applications to be performed. The database allows method and parameter storage. Robotic and computer interfaces allow communication between instruments.

The robotic apparatus can include central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory. These robotic fluid handling systems can utilize any number of different reagents, including buffers, reagents, samples, washes, assay components such as label probes, etc.

6. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154: 367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

C. EXAMPLES

1. Example 1: Evolution of a Thermophilic Strand-Displacing Polymerase Using Isothermal Compartmentalized Self Replication a) Materials and Methods (1) Strains, Primers, Plasmids, and Cloning All primers and gene sequences were ordered from IDT DNA Technologies. Primer sequences are included in Table 1; gene sequences are included in Supplementary Materials. All PCRs used Accuprime Pfx (Thermo Fisher Scientific) with manufacturer's recommended conditions unless otherwise noted. Standard Gibson assembly techniques were used for all assemblies unless otherwise noted. Shuffle-optimized KlenTaq, Bst LF, and all libraries for IsoCSR selections were cloned into pLTetO, an in-house designed plasmid based on the pASK-IBA37plus vector (IBA GmbH) that replaces the $pA_{tetO}$ promoter with a $pL_{tetO}$ promoter (Lutz 1997 and removes the 6×His tag, multiple cloning site, and Rop gene. For expression and purification, polymerase genes were cloned into pATetO 6×His, a similar modification of pASK-IBA37plus that retains the N-terminal 6×His tag and a similar pAtetO promoter with a single point mutation to make it unidirectional, but again removes the multiple cloning site and Rop gene, making it high copy. Assembled plasmids were transformed into electrocompetent Top10 (Thermo Fisher Scientific) or BL21 (New England Biolabs) *E. coli* strains as described and cultured in 2xYT media (Thermo Fisher Scientific) supplemented with 100 µg/ml Ampicillin to maintain plasmid at 37° C. unless otherwise indicated.

(2) Sequences and Analysis

Protein sequences were obtained from the sources indicated in the text. All known Taq mutations (Chen 2014) were mapped onto Taq for comparative analysis with the selected libraries. Protein sequences for Bst LF, Klentaq, v5.9, and v7.16 are included in Supplementary Materials. Sanger sequencing was utilized for all sequencing. For sequencing after rounds 3, 5, and 7, primers JNM245 and JNM259 were used (see Table 1). For verification after cloning into pATetO for expression, primers JNM135 and JNM141 were used, as well as either JNM101 for Bst LF-based sequences or JNM258 for Klentaq-based sequences (see Table 1). All sequence assembly and analysis utilized Geneious version 7.1 created by Biomatters. Alignments were performed with 65% identity cost matrix, gap open penalty 12, and gap extend penalty 3.

(3) Shuffled Library Preparation

Bst LF and Klentaq protein sequences were (Kiefer 1997; Korolev 1995) codon optimized for expression in *E. coli* using the IDT codon optimization tool. The resultant DNA sequences were then copied into Shuffle Optimizer, an in-house developed open-source python program that optimizes one sequence for DNA shuffling in reference to another (Milligan 2017), FIG. 7). Klentaq was optimized in reference to Bst LF. These DNA sequences were ordered as gBlocks (Integrated DNA Technologies). These sequences were amplified using primers JNM219 and JNM220 (Table S1), such that ~150 bp of homology to the backbone is added to each side of the gene for optimal shuffling. Fragments were run on an 0.8% agarose gel, cut, and purified using a Wizard SV Gel and PCR Cleanup System (Promega). 5 µg of equimolar concentrations of BstLF and Klentaq were brought up to a volume of 130 µL with deionized water, placed in Covaris microAFA tubes (part number 520045) and added to a Covaris S2 ultrasonicator. The ultrasonicator was run following manufacturer's recommendations for DNA shearing to get 150 bp fragment peaks. Approximately 500 ng of each fragmented library was included in a primerless PCR reassembly reaction using Platinum Taq HiFi (Invitrogen) containing 1× Platinum Taq HiFi buffer, 0.2 µM ea. dNTP, and 2 mM additional magnesium sulfate up to a final volume of 100 µL. The reactions were incubated on a thermal cycler at 95° C. for 2 min, then subjected to 35 cycles of the following series of incubations: 95° C. for 30 sec, 65° C. for 90 sec, 62° C. for 90 sec, 59° C. for 90 sec, 53° C. for 90 sec, 50° C. for 90 sec, 47° C. for 90 sec, 44° C. for 90 sec, 41° C. for 90 sec, and 68° C. 125 sec. The assembly reactions were purified using a standard PCR cleanup kit. 50 ng of DNA from each library assembly were amplified in a recovery PCR reaction with primers JNM221 and JNM222 (Table 1) using AccuPrime Pfx (Thermo Fisher Scientific). Fragments were run on an 0.8% agarose gel, cut, and purified using standard techniques. After Gibson assembly and transformation, serial dilutions of transformed cells were plated to calculate library efficiency. 20 colonies from each library were cultured, miniprepped, and sequenced.

(4) IsoCSR Mock Selections

The IsoCSR selection was initially optimized using wild-type Bst LF and BstXX, an inactive variant with 5 stop codons and an EcoRI digestion site. BL21 cells carrying pLtetO plasmids encoding either polymerase were cultured with increasing ratios of inactive BstXX:Bst LF and induced with a final concentration of 200 ng/ml Anhydrotetracycline (ATc, Sigma) for 4 hr at 37° C. for protein expression. $~1.5 \times 10^{10}$ cells were washed, then resuspended in 150 µL of an aqueous mixture consisting of 1× NEBuffer2 (50 mM NaCl, 10 mM Tris-HCl, 10 mM MgCl2, 1 mM DTT, pH 7.9), 0.4 mM dNTPs, 15 µg BSA, 30 µg lysozyme (Sigma), 1 mM additional dTTP, 18U dUTPase (ProSpec), and 75U Nb.BsmI (Nicking endonuclease, New England Biolabs). The mixtures were then added to 600 µL of oil mix (73% Tegosoft DEC, 7% AbilWE09 (Evonik), and 20% mineral oil (Sigma-Aldrich)) and emulsified using a TissueLyser LT (Qiagen) set to 35 Hz for 4 min. Emulsions were distributed equally into PCR tubes and incubated at 37° C. for 20 min (lysis), 65° C. for 3 hr (nicking and RCA) and 80° C. for 20 (to inactivate Bst LF), then cooled to 4° C. Emulsions were broken by spinning the reaction at 10,000×g for 5 min at 4° C., removing the top oil phase, adding 150 µL of $H_2O$ and 300 µL chloroform, mixing via pipette, and finally phase separating in a phase lock tube (5Prime). Pooled DNA was purified by ethanol precipitation and resuspended in 75 µL 1xHF Buffer (New England Biolabs). 5 µL of purified product was digested in 50 µL reactions containing 1xHF Buffer and 40 U DpnI (New England Biolabs) for 12 hr to remove unamplified plasmid DNA. DNA was recovered with 2 rounds of PCR using Phusion polymerase (New England Biolabs) (20 cycles each) with primers JNM182 and 183 for the first PCR and JNM102 and 183 for the second. Products were purified using PCR purification kits (Zymo Research) after each PCR reaction. Products were digested in 50 µL reactions containing 1× CutSmart Buffer (50 mM Potassium Acetate, 20 mM Tris-acetate, 10 mM Magnesium Acetate, 100 µg/ml BSA, pH 7.9) and 10 U EcoRI-HF (New England Biolabs) for 3 hr at 37° C. to distinguish Bst LF from BstXX and analyzed with gel electrophoresis.

(5) IsoCSR Selection of Thermostable, Strand-Displacing Polymerases

Libraries were cloned using Gibson assembly with 2 to 3-fold ratios of library insert to plasmid using 500-1,000 ng pLTetO plasmid backbone, then column purified using PCR purification kits (Zymo Research) and electroporated into BL21 cells. Typical transformations yielded $10^6$-$10^8$ cfu. Overnight cultures were diluted 1:20 into fresh media, grown for 1 hr at 37° C., induced with a final concentration of 200 ng/ml ATc, and further cultured for 4 hr. $~1.5 \times 10^{10}$ cells were washed with 75 µL 1×PCR buffer (50 mM KCl, 10 mM Tris HCl pH 8.3, 1.5 mM $MgCl_2$), and resuspended in 150 µL of an aqueous mixture containing 1×PCR buffer, 0.4 mM dNTPs, 15 µg BSA, and 1, 5, or 10 forward and reverse primers at a concentration of 0.5 µM each as described in Table 1, JNM264-283. The mixtures were then added to 600 µL of oil mix (73% Tegosoft DEC, 7% AbilWE09 (Evonik), and 20% mineral oil (Sigma-Aldrich)) and emulsified using a TissueLyser LT (Qiagen) set to 42 Hz for 4 min. Emulsions were distributed equally into PCR tubes and incubated at 95° C. for 5 min (lysis and template denaturation), 65° C. for 3 hr (RCA) and 80° C. for 20 min, then cooled to 4° C. Emulsion breaking, DNA purification, and DpnI digests were identical to mock selections. Products were recovered using 2-3 rounds of PCR amplification, 20-30 cycles each. Initial recovery PCRs used primers JNM219 and JNM220 and 1×HF buffer with Accuprime Pfx (Thermo Fisher Scientific), while subsequent PCRs used JNM221 and 222 with standard Accuprime conditions. PCRs were gel or column purified using PCR purification kits (Zymo Research). Products were cloned as before and electroporated into Top10 (Invitrogen) cells for sequencing or BL21 (New England Biolabs) cells for further selections as needed.

(6) Exonuclease III Parasite Removal

PCR library recovery in later rounds of IsoCSR was difficult, as reaction products were overrun with parasites, or small off-target amplicons. Where indicated, the following procedure was used to remove parasites. After the recovery PCR, products were purified using PCR purification kits (Zymo Research) and eluted in 6 µL H$_2$O. 600 ng PCR product was added to a 60 µL reaction containing 1×PCR buffer (50 mM KCl, 10 mM Tris HCl pH 8.3, 1.5 mM MgCl$_2$) and 60 U ExoIII (New England Biolabs). Reactions were assembled on ice, then incubated at 25° C. for 8.5 min. ExoIII digests DNA in the 3' to 5' direction at ~100 nt/min at 25° C. from both ends of double-stranded DNA, so this incubation is expected to remove products smaller than 1,700 bp, but can be adjusted as needed. Immediately following incubation, reactions were mixed with 30 µl, of 1×PCR buffer containing 0.4 mM dNTPs and 3 U Taq Polymerase (New England Biolabs) and incubated at 68° C. for 10 min, which heat inactivates the ExoIII enzyme and enables overlap extension of incompletely digested products.

(7) Polymerase Purification

Wild-type Bst LF and Klentaq as well as individual variants isolated from selection were cloned into pATetO 6×His (see Cloning above). Products were amplified using primers JNM316 and JNM309 for 5' and 3' Bst LF ends and primers JNM317 and JNM310 for Klentaq 5' and 3' ends, respectively. Plasmids were transformed into BL21 cells. Single colonies were inoculated into 5 mL Superior Broth (Athena Enzyme Systems) supplemented with 100 µg/ml Ampicillin and grown overnight at 30-37° C. Cultures were diluted 1:200 into 250 mL to 1 L fresh media and cultured to OD6000.5-1, then induced with a final concentration of 200 ng/mL ATc and further cultured for 3-7 hr for expression. Cells were harvested (4,000×g, 15 min, 4° C.), frozen in liquid nitrogen, and stored at −80° C. Cells were resuspended in 20-40 mL Lysis Buffer (20 mM Tris pH 7.4, 300 mM NaCl, 0.1% Tween-20 (Thermo Fisher Scientific), 10 mM Imidazole) supplemented with EDTA-free Protease Inhibitor Tablets (Thermo Fisher Scientific) and 0.5 mg/mL Lysozyme, and mixed end-over-end for 30 min at 4° C. Cells were further lysed using sonication. Supernatants were cleared (40,000×g, 30 min, 4° C.), heated for 65° C. for 20 min with shaking (400 rpm), and cleared again (20,000×g, 20 min, 4° C.). Polymerases were purified by metal ion chromatography. Briefly, lysates were added to 1 mL pre-equilibrated HisPur Ni-NTA resin and incubated for 30 min at 4° C. with end-over-end mixing for batch binding. These were applied to gravity columns and allowed to drain, then washed with 3×10 mL Wash Buffer (Lysis Buffer with 40 mM Imidazole) and eluted with 4×1 mL Elution Buffer (Lysis Buffer with 250 mM Imidazole).

For initial qLAMP screening, elutions were pooled, dialyzed into Storage Buffer (10 mM Tris pH 7.4, 100 mM KCl, 1 mM DTT, 0.1 mM EDTA, 0.5% Tween-20, 0.5% Triton-X100, and 50% Glycerol), and stored at −20° C. For characterization of thermostability and RCA assays, elutions (Bst LF, Klentaq, v5.9) were further purified and instead dialyzed into Buffer A (20 mM Tris, 150 mM NaCl, 1 mM DTT, 1 mM EDTA, and 0.1% Tween-20), then diluted with 14 mL Buffer A1 (Buffer A without Tween-20). Elutate was applied to a gravity column with 1 mL Type I Heparin agarose resin (Sigma) pre-equilibrated with 10 mL Buffer A1, then washed 2×10 mL with Buffer A1. Proteins were eluted on a 0.15 M to 0.8 M NaCl gradient, with polymerases typically eluting at 470-575 mM NaCl. Elutions were pooled and dialyzed into storage buffer and stored at −20° C. For Nickel purifications, protein purity was 50-90% as indicated by SDS-PAGE electrophoresis, typically ~80%. For Nickel and Heparin purifications, proteins were ≥99% pure. For all assays, protein concentrations were equilibrated to commercial Bst LF (New England Biolabs) using SDS-PAGE densitometry. It was chosen to normalize to concentration rather than activity in order to accurately compare the functionality of the variants to their wild-type ancestor polymerases, Bst LF and Klentaq.

(8) qLAMP Screening

LAMP reactions contained 1× Thermopol buffer (20 mM Tris-HCl, 10 mM (NH$_4$)$_2$SO$_4$, 10 mM KCl, 2 mM MgSO$_4$, 0.1% Triton X-100, pH 8.8, New England Biolabs), an additional 2 mM MgSO$_4$ (4 mM final concentration), 0.4 mM dNTPs, 20 pg template (GAPDH, Table 2), 1× primer mix (FIP=1.6 uM, BIP=1.6 uM, LR=0.8 uM, F3=0.4 uM, B3=0.4 uM, Table 2), 1M Betaine, 1× EvaGreen fluorescent DNA intercalating dye (Biotium) to monitor amplification, and 2.5 ul polymerase in a total reaction volume of 25 µL. Reactions used 5 primers instead of the typical 4 or 6 as in previous studies (Bhadra 2015). Fully assembled reactions were heat denatured at times and temperatures indicated in the text prior to LAMP with or without polymerase included as noted. For SD Pol LAMP tests, SD Polymerase Hotstart was purchased (Bioron), and reactions were assembled according to manufacturer's recommendations (1×SD Reaction Buffer, 3.5 mM MgCl$_2$, 15-50 U SD Pol) with the addition of primers, template, and fluorescent dye as mentioned above; these reactions were heated for 2 min at 92° C. to activate hotstart before assaying.

Reactions were monitored using a LightCycler 96 quantitative PCR machine (Roche) by incubating at 68° C. and taking FAM fluorescence measurements every 4 min, followed by a post-amplification melt curve analysis to determine product specificity. Curves were analysed using accompanying software with absolute quantitation and Tm calling analyses. Thus, Cq values (where indicated) represent crossing a fluorescent threshold value determined by the software and correspond to a time point (multiply by 4 min) rather than a cycle number as in qPCR.

(9) Thermostability Assays

Kinetic activity assays were performed according to manufacturer's instructions using the EvaEZ fluorometric polymerase activity assay kit (Biotium). 10 µL reactions consisting of 1×PCR buffer (50 mM KCl, 10 mM Tris HCl pH 8.3, 1.5 mM MgCl$_2$) and 0.1 µL v5.9 (Nickel and Heparin purified) were incubated at 85, 89.5, or 92.5° C. for 0, 1, 2, 5, or 10 min, then immediately cooled on ice. Reactions were mixed with 10 µL 2×Polymerase Activity Mix and monitored on a Light Cycler 96 with readings every 1 min. Initial slopes, indicating reaction rates, were measured. Activity of samples was normalized to the no heating control and expressed as a percentage.

(10) Rolling Circle Amplification Assays

RCA reactions contained 1× Thermopol buffer (20 mM Tris-HCl, 10 mM $(NH_4)_2SO_4$, 10 mM KCl, 2 mM $MgSO_4$, 0.1% Triton X-100, pH 8.8, New England Biolabs), 0.4 mM dNTPs, 100 ng pATetO plasmid template (excepting no template controls), 1×EvaGreen fluorescent DNA intercalating dye (Biotium) to monitor amplification, and 2.5 ul polymerase (Nickel and Heparin purified) in a total reaction volume of 25 µL. Where indicated, reactions also included 0.5 µM each of 20 primers, 10 forward and 10 reverse, for exponential amplification (JNM264-283, see Table 1). For reactions containing nicked template, 2.5 µg of plasmid pATetO was nicked in a 50 µL digestion reaction containing 1× NEBuffer 3.1 (100 mM NaCl, 50 mM Tris-HCl, 10 mM $MgCl_2$, 100 µg/ml BSA, pH 7.9) and 20 U Nb.BsmI (New England Biolabs) by incubation at 65° C. for 1.5 hr followed by 80° C. for 20 min to heat-kill the nickase. 2 µL of this reaction or 50 ng/µl non-nicked pAtetO in 1× NEBuffer 3.1 were added to reactions containing template in order to maintain consistency.

Reactions were monitored similarly to qLAMP, using a LightCycler 96 quantitative PCR machine (Roche) by incubating at 68° C. and taking FAM fluorescence measurements every 4 min, followed by a post-amplification melt curve analysis to determine product specificity. Curves were analysed using accompanying software with Tm calling analysis. Unlike LAMP, RCA reactions do not produce qPCR-like curves that are easily interpretable by the Light Cycler 96 software. Thus, all RCA data presented is unprocessed fluorescence data, and therefore does not have Cq values.

(11) Structural Analysis of Polymerases

Protein structure files (PDB) were obtained from RCSB (Berman 2000). The structures used in this study were 1l3s for Bst LF and 3ktq for Klentaq (Kiefer 1998; Li 1998). Alignments and other structural figures were prepared using pymol (The PyMOL Molecular Graphics System, Version 1.8 Schrödinger, LLC).

b) Results (1) Isothermal Selection Schemes for DNA Polymerases

While there are a number of schemes for the self-selection of thermophilic DNA polymerases for PCR applications, there have previously been few ways to select functional polymerases that work at more moderate temperatures and for end uses other than PCR. A novel selection strategy termed term isothermal compartmentalized self-replication (IsoCSR, FIG. 1) has been developed. In this scheme, libraries of polymerase variants are expressed in cells, and cells are ensconced within individual compartments in water-in-oil emulsions. However, genes that produce functional polymerases are not amplified by PCR, as is the case with techniques such as compartmentalized self-replication (CSR) that rely on thermal cycling to disrupt cells, but rather via rolling circle amplification (RCA) and enzymatic lysis of cells. Thus, the scheme is able to accommodate mesothermophilic (functional up to 70° C.) strand-displacing polymerases, such as the widely used Bst polymerase. Others have recently used an isothermal variant of compartmentalized self-replication to evolve phi29 polymerase, but this method relied on repeated freeze-thaw cycles to lyse emulsified cells and would not be suitable for a more thermostable polymerase (Povilaitis 2016).

IsoCSR begins by transforming *E. coli* with an expression plasmid carrying a library of polymerase genes cloned downstream of an inducible promoter (FIG. 1a). Polymerase expression is initiated with anhydrotetracycline (ATc), after which the cells are harvested and resuspended in an aqueous mixture containing buffer, dNTPs, a high-temperature nicking endonuclease (Nb.BsmI, New England Biolabs), and lysozyme. This mixture is emulsified using established methods (Ellefson 016; Kiefer 2014). Cells are lysed within the emulsion compartment enzymatically by lysozyme during an initial 37° C. incubation, releasing polymerase and plasmid. Raising the temperature to 65° C. activates the thermostable nickase, which nicks the plasmid to enable linear RCA via strand-displacing polymerization. After the reaction, emulsions are broken and genes encoding variants that have been successful at RCA can be further enriched by PCR. Multiple cycles of emulsion, expression, RCA, extraction, and PCR are anticipated to yield polymerases that are highly functional under isothermal, rather than thermal cycling, regimes.

IsoCSR was attempted (Kiefer 1997) with Bst LF, a mesothermophilic enzyme that is especially interesting because of its strand-displacement properties, facilitating its use in powerful isothermal amplification schemes such as rolling circle amplification (RCA) (Zhang 2001), helicase-displacement amplification (HDA) (An 2005), and loop-mediated isothermal amplification (LAMP) (Notomi 2000). RCA was focused on for self-amplification as it can most readily reproduce full-length genes. Enzymatic lysis with lysozyme and template amplification via the mesothermophilic nicking endonuclease Nb.BsmI was designed and verified, which generates an RCA initiation site on the expression plasmid. In-emulsion cell lysis, nicking, and RCA were all verified independently, then combined for further optimization (see Selection Optimization).

Once the selection protocol was fully optimized, a mock selection experiment was carried out to investigate whether functional polymerases could be enriched relative to a nonfunctional mutant. The non-functional variant BstXX was created by inserting 6 stop codons and a unique EcoRI cut site upstream of the active site of Bst LF. IsoCSR was then performed with ratios of 1:10, 1:100, and 1:1000 Bst LF:BstXX cells. PCR recovery products were digested with EcoRI to differentiate between Bst LF and BstXX. The mock selection demonstrated that it can be possible to recover wild-type Bst LF even in the presence of $10^3$ excess inactive mutant Bst (FIG. 2), a ratio that is similar to that observed for some other polymerase selections (Chen 2016) and significantly improves upon reports with phi29 polymerase (Povilaitis 2016), but was less efficient than CSR, which was reported to recover active variants in the presence of a $10^6$ excess of an inactive mutant (Ghadessy 2001). This could be due to the linear nature of rolling circle amplification and to the requirement that multiple enzymes (polymerase, nickase, lysozyme) function within the emulsion.

To improve the selection coefficient and recovery efficiency, a modified IsoCSR selection was contemplated in which nickase and lysozyme were replaced with thermal denaturation, similar to the original CSR protocol, yet still requiring strand displacement activity for RCA. So-called thermostable IsoCSR, which includes a pre-RCA heat denaturation step for cellular lysis and template denaturation, also allowed primer-initiated hyperbranched RCA, which has exponential rather than linear reaction kinetics. However, because this embodiment necessitated thermostability in addition to strand displacement activity, neither wild-type Bst LF nor other strand-displacing polymerases could effectively carry out the cycle. A thermostable version of Bst was therefore created that could in turn be used to instantiate thermostable isoCSR.

(2) Library Generation

DNA shuffling has proven useful as a means of generating diverse protein libraries, especially for selecting polymerases with novel phenotypes (Baar 2011; Stemmer 1994; Crameri 1998). A library for thermostable isoCSR was created by shuffling two family A polymerases: the strand-displacing DNA polymerase I from *Bacillus* (*Geobacillus*) *stearothermophilus* (Bst) and the thermostable *Thermus Aquaticus* (Taq). The large (Klenow) fragments of these polymerases, Bst LF and Klentaq, are truncated versions that lack the N-terminal 5'-3' exonuclease domain, and thus promote strand displacement activity, although to different degrees (Kiefer 1998; Lawyer 1993). Bst LF and its engineered homologs are the polymerases of choice for high temperature isothermal amplification reactions due to their high strand displacement activity (Mori 2013; Notomi 2000; Lizardi 1998; Zhang 2001), but are unstable at temperatures above 70° C. In contrast, Klentaq has much weaker strand displacement activity but is more thermostable than full-length Taq, with a half-life of 21 min at 97.5° C. (Lawyer 1993). Through molecular breeding of these related-but-phenotypically-different enzymes, a chimeric variant was selected that would combine both activities.

Figure 7:
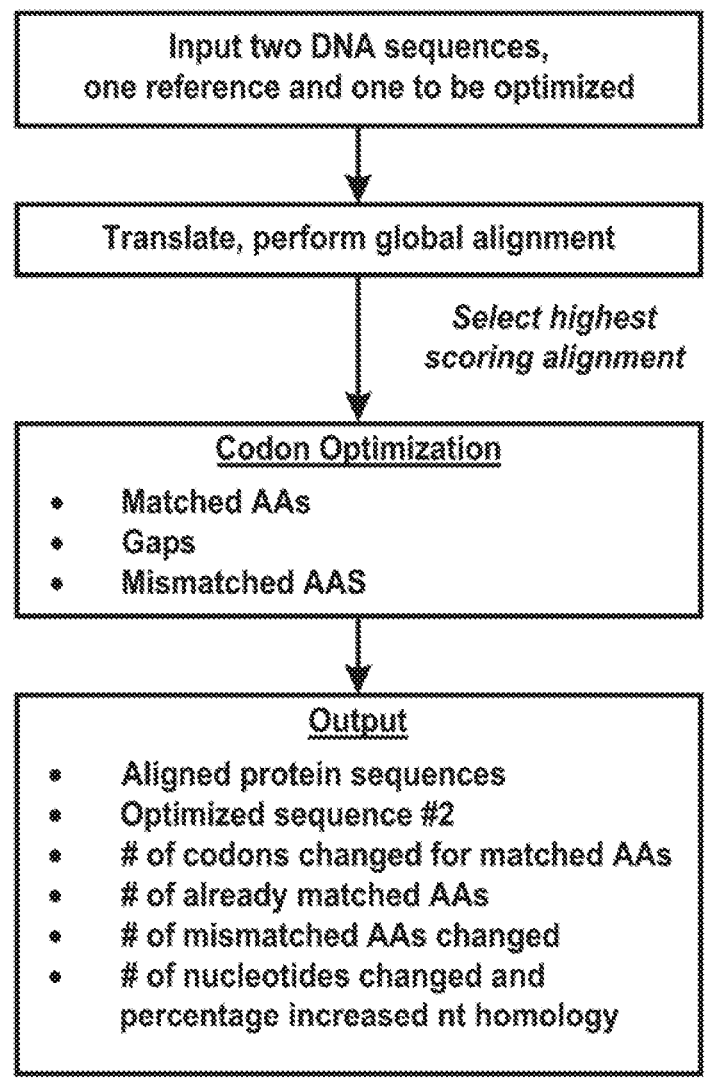
FIG. 7 shows program architecture of shuffle optimizer. The functionality of Shuffle Optimizer, a program used to generate optimized DNA sequences for library shuffling, is summarized. The program is available as open-source python code.

DNA shuffling requires high levels of homology between molecules for success (Baar 2011). However, Bst LF and Klentaq were only 53% identical at the DNA level, which proved to be insufficient for shuffling methods. Increasing homology at the DNA level leads to increased shuffled library diversity, and has previously been accomplished by computer programs that optimized codons to maximize stretches of homology between DNA molecules without changing the resulting protein (Moore 2000; Moore 2002; Moore 2001). The lack of ready availability of these programs led us to develop the development of a Python script called Shuffle Optimizer (Milligan 2017), now available as open-source code for public use (FIG. 7). Shuffle Optimizer generated an optimized Klentaq DNA sequence that was nearly 70% identical to Bst LF DNA, a significant improvement over the original sequence identity (53%).

Figure 8:
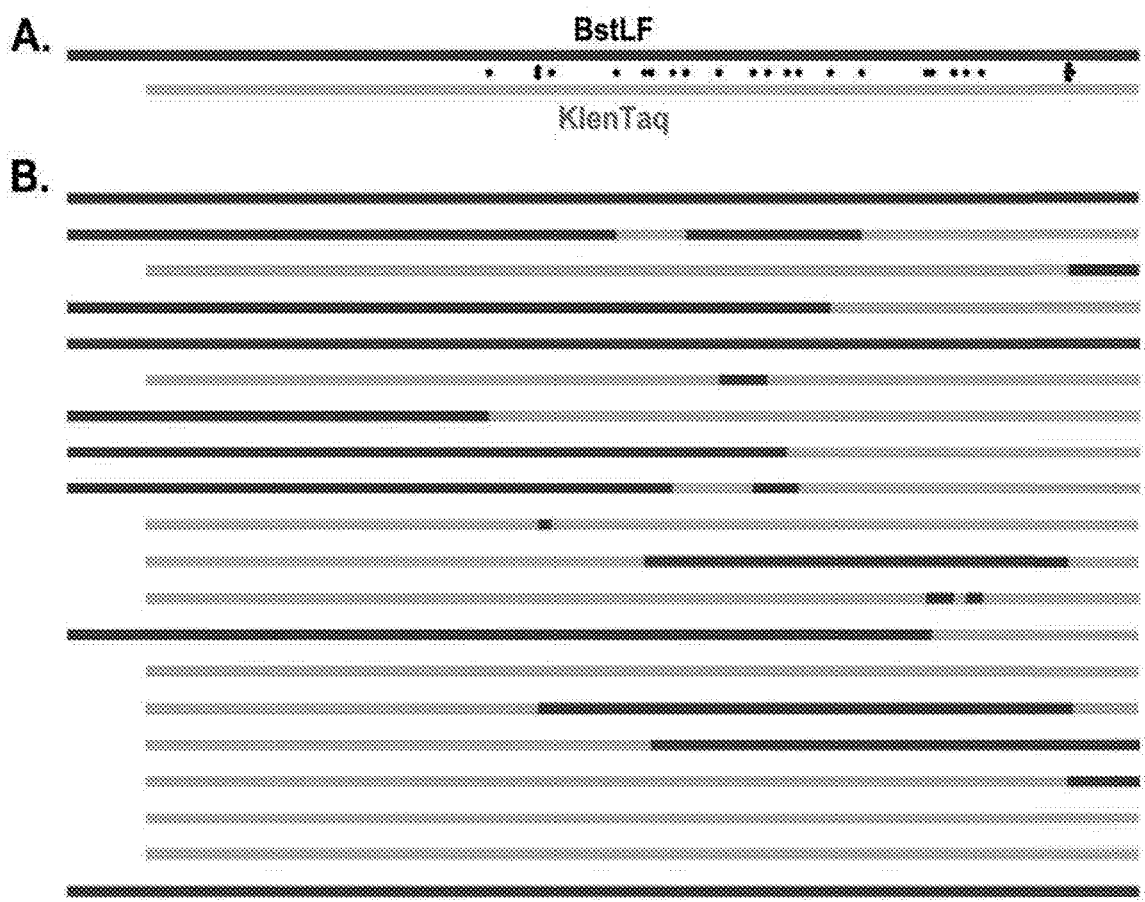
FIG. 8 shows results from DNA shuffling of Klentaq and Bst LF. 20 individual variants were sequenced from the shuffled library. The location and number of crossovers observed is summarized (A). Each individual variant is also pictured (B).

Optimized sequences were then shuffled. Ultrasonication was used to generate 150 bp DNA fragments of Bst LF and optimized Klentaq, and these fragments were then mixed in equal ratios and reassembled using overlap extension PCR (see also Methods). Shuffling of the optimized sequences resulted in a library of ca. $5 \times 10^7$ variants, of which 14 out of 20 unselected variants were chimeric, with an average of 1.8 crossovers per chimeric variant (FIG. 8). A side-by-side attempt to shuffle sequences not optimized by Shuffle Optimizer resulted in 0 observed crossovers in 20 variants. Notably, few crossovers were observed near the 5' ends of the genes, likely due to high sequence divergence in this region even after optimization. Nevertheless, Shuffle Optimizer enabled the successful creation of a shuffled protein library from Bst LF and Klentaq sequences where it had previously failed, and should be useful for other researchers interested in shuffling or recombining distantly related sequences.

(3) Selection of Thermostable, Strand-Displacing Polymerases

Thermostable polymerases capable of isothermal amplification were selected by carrying out hyperbranched rolling circle amplification (hbRCA) in emulsio. The use of hbRCA greatly simplified the selection by eliminating the need for nicking endonuclease and lysozyme, as these steps were replaced with a pre-RCA denaturation step of 95° C. at 5 min that both lysed cells and denatured the plasmid for primer binding (FIG. 1b). In addition, hbRCA likely increased the selection coefficient for active variants because it involves exponential reaction kinetics (Zhao 2015; Dean 2001; Lizard 1998; Zhang 2001).

This selection can yield thermophilic enzymes, as amplification is dependent on the polymerase surviving the initial denaturation step. The polymerase must also retain or acquire strand displacement activity in order to perform hbRCA. Interestingly, while Klentaq had sufficient strand displacement activity to carry out RCA on nicked templates, it initially failed to amplify plasmid DNA in a hbRCA reaction (see FIG. 5b versus 5c). On the other hand, Bst LF has strand-displacing activity sufficient for hbRCA, but lacks thermostability. Thus, neither wild-type polymerase used to generate the library—indeed, no polymerase known—possessed the combination of activities necessary to survive the selection, a strong argument for the selection of a chimera.

Figure 9:
FIG. 9 shows exonuclease III treatment and Taq recovery of contaminated products. An equimolar mixture of 3 dsDNA molecules of sizes 647 bp, 1,228 bp, and 1,717 bp was subjected to ExoIII digestion at 25° C. for various times, then mixed with Taq and incubated at 68° C. for 10 min. The exonuclease breaks down the bands synchronously in the 3' to 5' direction, while the subsequent Taq extension recovers bands that still have overhangs. Increasingly large bands are eliminated as digest time is increased. While the smallest band appears to re-emerge in later reactions, this is actually the breakdown product from the digested middle band. This treatment is effective for removing parasites from PCR reactions.
Figure 10:
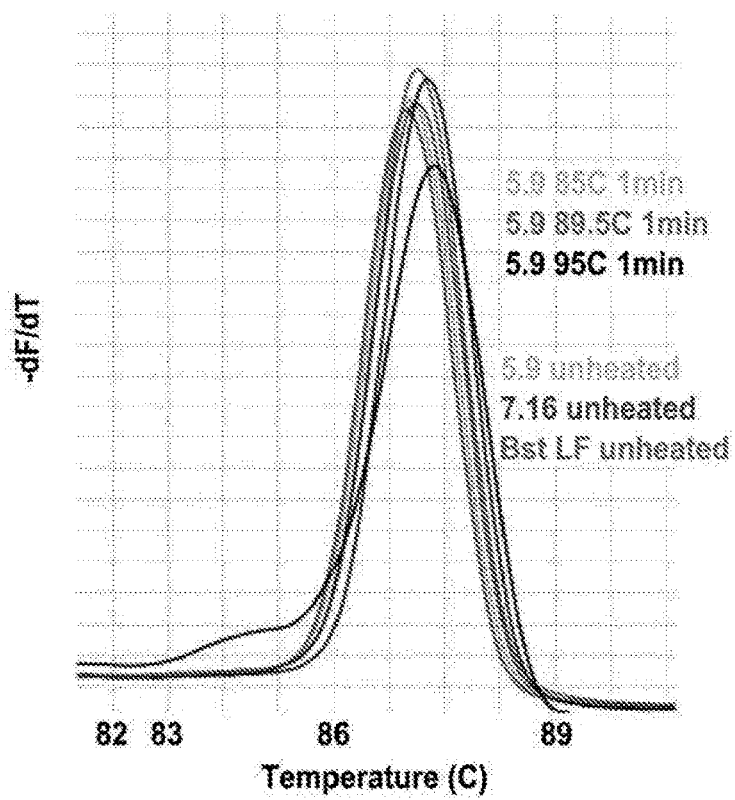
FIG. 10 shows the melt curve analysis of qLAMP screening. LAMP reactions were subjected to a melt curve analysis on the LightCycler 96 qPCR machine (Roche) following isothermal LAMP incubation for product specificity analysis (see FIG. 4 for data). All products have similar melt peaks, including those from heat-treated v5.9 reactions.
Figure 11A:
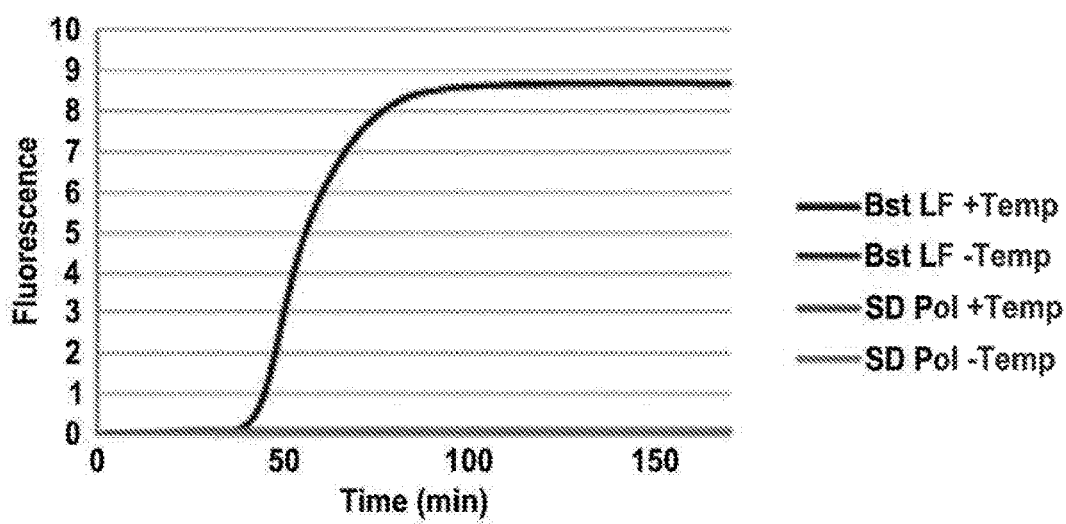
FIGS. 11A and 11B show LAMP amplification with Bst LF and SD Pol. SD Pol (Bioron), a commercially available Taq mutant reportedly capable of LAMP (Ignatov 2014) was compared with other variants in an initial qLAMP screening (11A). Template is included as indicated. Using manufacturer recommended conditions, Amplicons were not generated with SD Pol. Other templates were also attempted. SD pol is capable of Rolling Circle Amplification from a nicked plasmid template (11B).
Figure 11B:
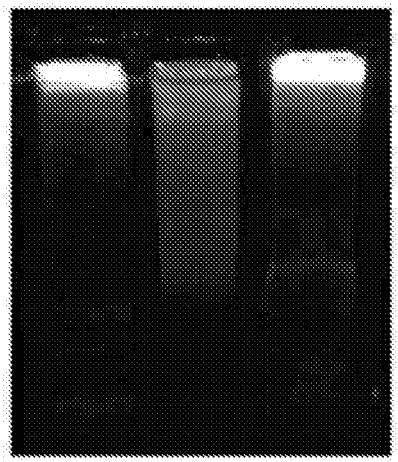

7 rounds of IsoCSR were turned to evolve novel thermostable, strand-displacing variants. 20 primers were utilized in the emulsion hbRCA reaction, with 10 forward and 10 reverse primers equally spaced around the non-library portion of the expression plasmid at a concentration of 0.5 µM each. The stringency of the selection was increased over successive rounds by scaling down the number of primers included, as the number of primers positively correlated with replication efficiency (Dean 2001). This scaling methodology required optimization to ensure successful recovery of the library, as overly high selection pressures resulted in no product recovery from post-emulsion PCR. Indeed, post-emulsion library recovery in later rounds with only two hbRCA primers was challenging, as reactions were dominated by parasites, small off-target PCR products that were preferentially amplified over the larger (~1800 bp) polymerase gene product. To circumvent these difficulties a novel parasite removal strategy was developed that relied on exonuclease III (ExoIII, New England Biolabs), a synchronous 3' to 5' DNA exonuclease with well-studied reaction kinetics (Hoheisel 1993; Roychoudhury 1977; James 1984). By lowering the digestion reaction temperature to 25° C., where ExoIII cuts at a rate of ~100 bp, it was found that 8 minutes of treatment would completely digest products less than 1700 bp in length, while leaving overhangs on larger products. The remaining hemiduplexes served as substrates for primer extension by Taq polymerase at 68° C. (a temperature that also denatured ExoIII). The combined ExoIII digestion and Taq polymerase extension resulted in the recovery of only the desired large product from later rounds of selection (FIG. 9), and led to successful library recovery from IsoCSR in Rounds 5, 6, and 7.

In addition to seeing how the selection could respond to increased stringency (limiting the primers required for successful amplification), its progress was assessed by sequencing 12-20 individual variants from Rounds 3, 5, and 7. Most polymerase variants were chimeras composed of Bst LF and Klentaq. In later rounds, these insertions appeared to converge. In Round 5, over half (7/13) of the observed insertions overlapped at the C terminus of the protein (Klentaq residues 530-535/Bst LF residues 570-575); this had increased to 75% of the chimeric population by Round 7.

Increasing numbers of non-synonymous mutations were also observed over successive rounds, presumably due to replication errors that arose during self-replication and then became fixed. Several concentrated clusters of mutations occurred in Round 7 at or near previously identified mutations in Taq that led to a relaxation of substrate specificity (Ghadessy 2001; Chen 2014; Laos 2013; Leconte 2010; Suzuki 1996; Vichier-Guerre 2006). Relaxed substrate specificity is often synonymous with decreased fidelity (Chen 2014), and it appeared that the library was becoming enriched for error-prone polymerases with increased replication rates, as has been seen in previous selections (Suzuki 1996; Patel 2001; Aryan 2010).

(4) Variant Purification and Screening

Since it seemed from sequencing results as though there was no consensus sequence for thermostable, strand-displacing polymerases, for initial screening, twelve variants from Round 7 and six variants from Round 5 were cloned into a protein expression vector with an N-terminal 6×His. Of the 18 polymerases cloned, 5 variants could not be expressed and purified in sufficient quantities for screening; these latter largely consisted of proteins that had a Klentaq backbone with a C-terminal Bst insertion.

The 13 purified variants were screened for thermostability and strand displacement activity using loop-mediated isothermal amplification (LAMP) with a well-known GAPDH template as an assay, as this combination can readily yield interpretable qPCR-like exponential amplification curves. qLAMP Reactions were assembled and monitored on a LightCycler 96 qPCR machine (Roche) as previously described (Jiang 2015; Zhang 2001), except that EvaGreen intercalating fluorescent dye (Biotium) was used rather than oligonucleotide probes (see also Methods). Amplicon homogeneity was monitored via post-reaction melt curves (Njiru 2008). A secondary screen was also carried out using RCA with a nicked plasmid template at 68° C.; this assay requires less robust strand displacement capability.

Initial screening identified two highly functional variants capable of LAMP and RCA, v5.9 from Round 5 and v7.16 from Round 7 (FIG. 3a). Cq values, which represent the time at which fluorescence exceeds a determined threshold value (see Methods), indicated that v5.9 was 24.7 min slower (Cq=16.6) than purified wild-type Bst LF (Cq=10.5), while v7.16 was 7.3 min faster (Cq=8.6), all with similar melt peaks. v5.9 and v7.16 were compared with SD Pol (Bioron), a commercially available Taq mutant reportedly capable of LAMP (Ignatov 2014); however, it was found that this enzyme was unable to amplify products via LAMP under recommended conditions, though it was capable of RCA from a nicked plasmid template. Additional variants (v7.5) that were not LAMP capable could also carry out RCA.

(5) Sequences of Functional Polymerase Variants

170. Sequencing data showed that variant 5.9 had a Klentaq backbone with a small Bst insertion and two point mutations, while variant 7.16 consisted of Bst LF with no insertions and four point mutations. The insertion in v5.9 is located near other insertions observed in Round 5, but did not contain an insertion in the C-terminal region where most insertions converged. Similar polymerases with C-terminal insertions may have been lost in the initial screen, as chimeras containing C-terminal Bst LF insertions could not be purified in sufficient quantities for testing, as described above. V7.16, had several mutations (Q249R, N416S, E453G) occurring at or near known Taq mutations related to decreased fidelity, similar to other sequenced variants from Round 7. Two of these mutations (N416S, E453G) were within highly-mutated regions in Round 7, while an additional mutation (Q249R) aligned to a Taq mutation involved in unnatural nucleobase incorporation.

(6) Thermal Stabilities of Evolved Polymerase Variants

Figure 12:
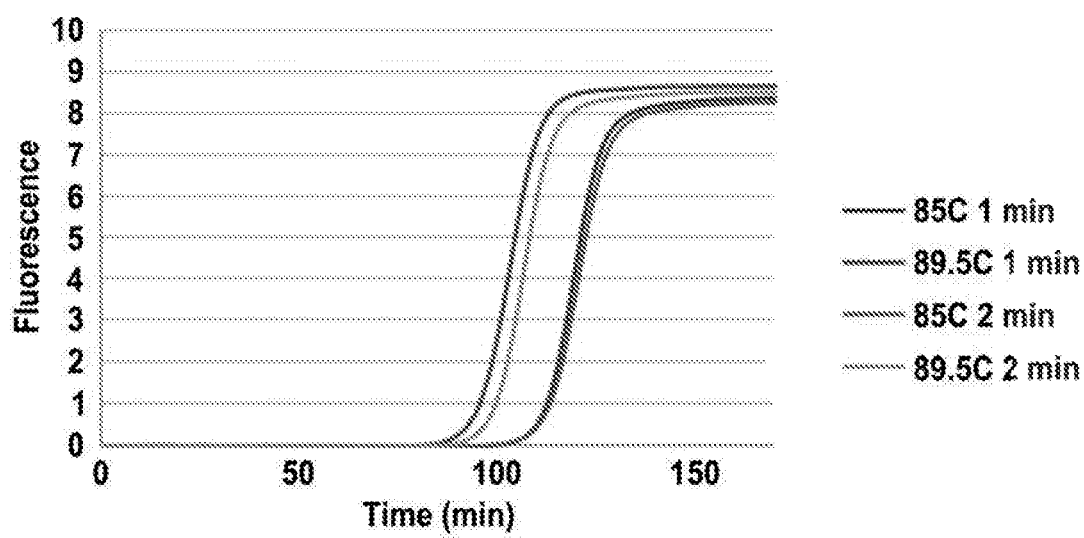
FIG. 12 shows LAMP activity comparison of v5.9 after 1 or 2 min of heating. Variant 5.9 activity was assayed using qLAMP reactions identical to those in the main text with 1 or 2 minutes of pre-reaction heating at the indicated temperatures. Results are similar at these temperatures whether heated for 1 or 2 min, with 89.5° C. producing more rapid amplification. This can be due to improved template denaturation.

One key advantage of a more thermostable strand-displacing polymerase is the ability to carry out isothermal amplification reactions that rely on strand separation, such as LAMP, with an initial strand denaturation step or at higher temperatures in general. To that end, 'one pot' reactions were set up with V5.9 and v7.16 in which the entire reaction was pre-heated for 1 min at 85° C., 89.5° C., or 95° C. prior to carrying out the remainder of the qLAMP amplification reaction. Remarkably, variant 5.9 successfully performed LAMP after heating at all the tested temperatures, while neither Bst LF nor v7.16 were able to amplify after any of the thermal challenges (FIG. 3b). Variant 5.9 performed just as well after heating at 85° C. or 89.5° C. (FIG. 3b) as it did in assays without pre-heating (compare with FIG. 3a). Increasing heating time from 1 min to 2 min did not further affect performance (FIG. 12). These results show that v5.9 can be used in much more streamlined LAMP assays in which an initial thermal denaturation provides primers with uniform access to templates, including G:C rich templates, which can lead to orders-of-magnitude improvements in assay sensitivity (Njiru 2008; Sagner 1991; Kong 1993). Because the evolved polymerase is thermostable, it can now be directly included during the denaturation step, circumventing an unwieldy workflow that would require opening tubes between heat steps, something that is particularly onerous with multiple samples in parallel. This advance also affords for the possibility of including thermal denaturation in lab on a chip diagnostic devices that use isothermal nucleic acid amplification methods.

Figure 4:
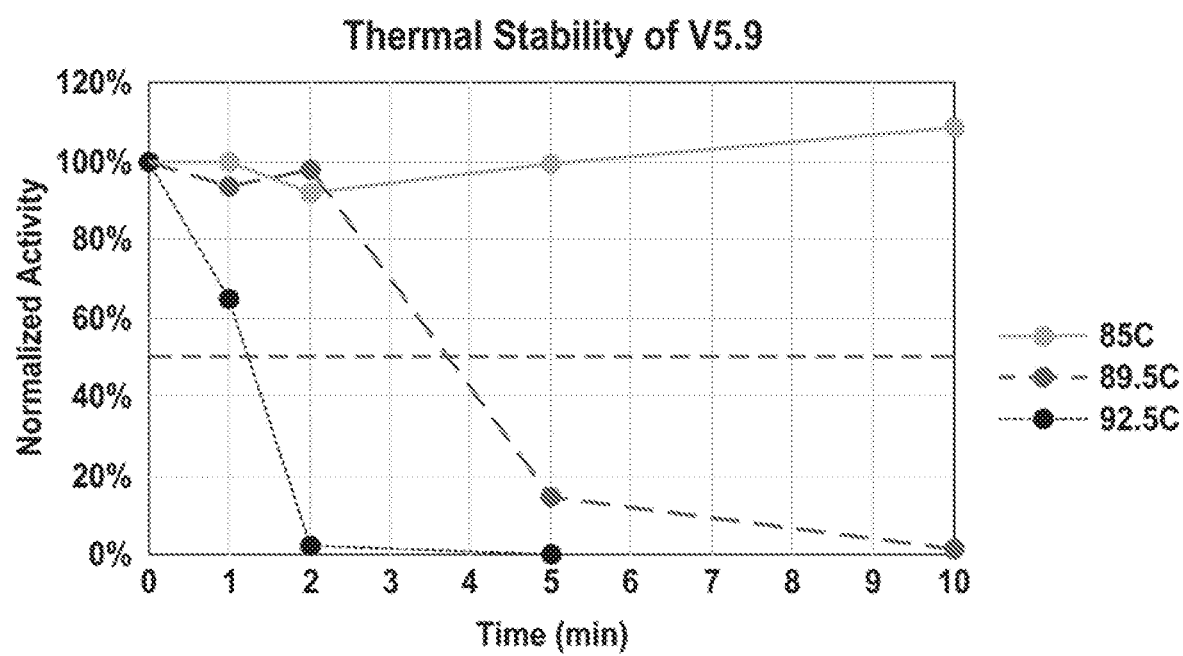
FIG. 4 shows thermostability kinetics of v5.9. Thermostability of Variant 5.9 was characterized by examining the polymerase's reaction rate in an extension assay after preheating at various temperatures and times. Activity is normalized to enzyme activity without heating. Dashes indicate temperature. A light grey line indicates ½ life (50% activity).

In order to further characterize the thermal tolerance of variant 5.9, activity assays were performed similar to radioactivity-based assays previously described (Ghadessy 2001; Lawyer 1993; Sagner 1991), except that the EvaEZ fluorometric polymerase activity assay kit (Biotium) was used to monitor reactions in real-time. Activity was determined by measuring initial reaction rates after heating at 85° C., 89.5° C., or 92.5° C. for 1-10 min and normalizing these to activity without heating (FIG. 4). V5.9 retained full activity after heating at 85° C. for up to 10 min. At 89.5° C., the enzyme had a half-life of approximately 3.75 min, while at 92.5° C., the half-life was ~1.3 min. This represents a significant decrease in thermal tolerance from the variant's parent enzyme, Klentaq, which has a half-life of ~21 min at 97.5° C. and shares 97.5% protein sequence identity with v5.9.

(7) Assay Performance of Variant 5.9

The combination of thermostability and strand displacement characteristics found in v5.9 can prove useful in other reactions as well. v5.9 was tested against its parent enzymes in high temperature rolling circle amplification reactions, including both linear (single initiation) and exponential (multiple primer, hyperbranched) RCA (Lizardi 1998).

Figure 5:
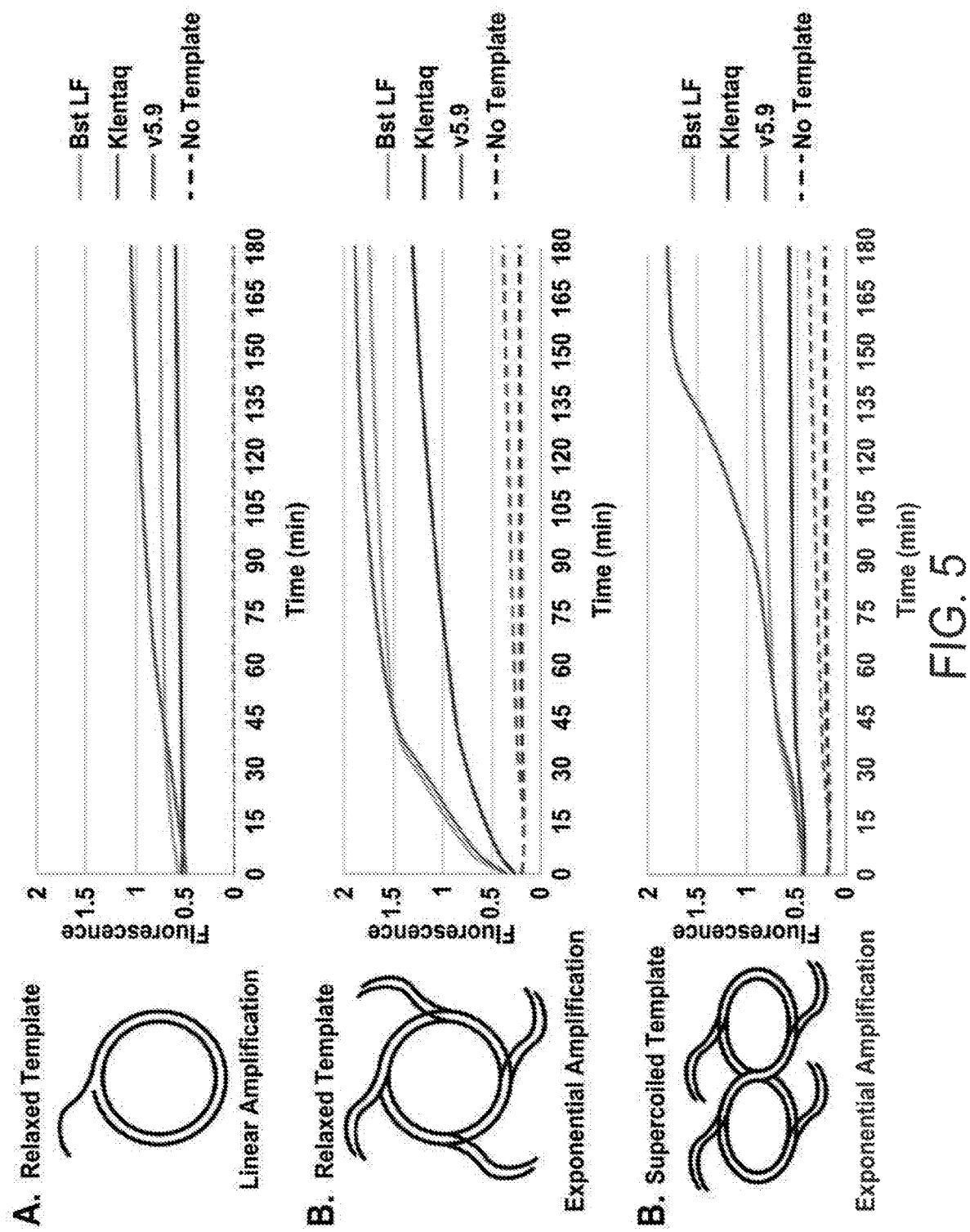
FIG. 5 shows Rolling Circle Amplification (RCA) with V5.9, Bst LF, and Klentaq. Enzymes were incubated with nicked template (A, linear amplification), nicked template with forward and reverse primers (B, exponential amplification), or supercoiled plasmid with forward and reverse primers to mimic the RCA reaction in our selections (C, exponential amplification). Polymerase colors are coordinated between graphs and with other figures. Dashes indicate negative controls.

A nicked plasmid was used to monitor linear RCA and strand displacement activity at high temperatures similar to other strand displacement assays (Kong 1993), and melt curve analyses were carried out to ensure that only specific products were being amplified. Reactions were monitored via EvaGreen incorporation on a LightCycler 96 qPCR machine (Roche). The plasmid pTetA-6×His was used as a template, and was nicked at a single site with Nb.BsmI (New England Biolabs). Bst LF, Klentaq, and v5.9 were all able to amplify DNA using linear RCA from a nicked plasmid template to varying degrees (FIG. 5a). V5.9 produced the largest signal and fastest rate, while Bst LF reached an early plateau, despite initially producing signal faster than v5.9. Klentaq, a weak strand displacer, produced very little signal, yet had melt curve peaks similar to Bst LF and v5.9, indicating at least some amplification (FIG. 13a). No template negative controls generated no signal, as expected.

When primers were included with the nicked template (the same 20 primers—10 forward and 10 reverse—used in the selections) and samples were pre-heated at 95° C. for 1 min to allow primer binding, all three polymerases were capable of exponential hbRCA amplification (FIG. 5b). Variant 5.9 and Bst LF produced nearly identical curves, while Klentaq produced lower signal due to its weak strand displacement activity. No template controls produced small amounts of non-specific signal as indicated by melt curve analysis, likely from the extension of primer dimers, a common issue in multiply primed hbRCA (FIG. 13b).

Supercoiled template hbRCA reactions are similar to randomly primed RCA reactions, which typically use low temperature Phi29 polymerase to amplify genomic and plasmid DNA (Nelson 2002; Reagin 2003). In addition, hyperbranched RCA reactions with non-nicked, supercoiled plasmid templates are similar to the reaction mechanism that was actually used in the IsoCSR selections. v5.9 proved to be the only polymerase capable of exponential amplification from the supercoiled plasmid templates (FIG. 5c). The curve produced by v5.9 appears to be biphasic, producing a small amount of amplification and plateauing before reaching exponential amplification. While Bst LF initially produced some amplification, the curve appears to be linear and plateaus prior to reaching an exponential phase. Klentaq is unable to produce any product, as confirmed by melt analysis (FIG. 13c). Note that the no template controls for this experiment are identical to FIG. 5b; this is because all experiments were run simultaneously, and the no template controls for exponential hbRCA are the same regardless of whether the template is nicked or not in positive reactions.

Overall, v5.9 has superior strand displacement activity to Bst LF in both linear and hyperbranched RCA, and has acquired the unique ability to exponentially amplify supercoiled plasmid DNA via hyperbranched RCA (an activity that is not present in either of the polymerases used to generate the shuffled library). The only other polymerase known to be capable of exponential RCA from supercoiled templates is φ29, largely considered the most processive strand displacement polymerase known (Blanco 1989; Nelson 2002; Reagin 2003).

(8) Correlating Structure and Function of v5.9

Sanger sequencing had revealed that variant 5.9 is a chimera consisting mostly of Klentaq, with a 14 aa insertion of Bst LF (Bst LF residues 305 to 318) resulting in 11 mutations (D283E, P284G, P286L, D287K, L288V, I289V, H290R, R292D, G294K, R295K, L296V) as well as 2 silent mutations and 2 non-synonymous mutations, E322G and L484S (FIG. 6b). The Bst LF insertion was unique, but similar insertions were also found.

In the original crystal structure characterizations of Bst LF and Klentaq (Kiefer 1997; Korolev 1995), it was noted that increased ratios of certain amino acids (E:D, L:I, and R:K) and increased numbers of prolines can be indicative of higher thermal tolerance. Thus, it is notable that the mutations observed in v5.9 shift most of these ratios toward decreased thermostability when compared to Klentaq: 3 leucines were lost compared to only one isoleucine, 3 lysines were gained compared to a loss of one arginine, and two prolines were lost. This correlates to the observed loss of thermostability of v5.9 relative to Klentaq.

In order to provide a structural context for the observed functional properties of variant 5.9, the structure of v5.9 was modelled in comparison to its ancestors, the large fragment of Bst and Taq polymerases (Bst LF and Klentaq). When the Bst LF and Klentaq structures are aligned, the structures are quite homologous, especially in the finger and thumb subdomains (FIG. 6a). The crossover region was mapped where the Bst LF insertion occurred in v5.9 onto the structures of Klentaq and Bst LF for comparison. The inserted region was located in the polymerase domain at the base of the thumb subdomain, just below the I helix (FIG. 6a). The insertion observed in variant 5.9 differed significantly between the two protein structures (FIGS. 6c and 6d, blue). In Klentaq (FIG. 6c), the original region is largely unstructured, with a small alpha helix (denoted as *) near the I helix. In Bst, the homologous region (FIG. 6d) has a larger alpha helix, essentially extending the length of the I helix. This I helix is an essential structure of the thumb subdomain, forming an antiparallel coiled-coil structure with the neighboring H helix that is dependent on hydrophobic interactions between leucine residues on the two helices (Kiefer 1997). In addition to extending the I helix, the Bst insertion observed in v5.9 results in an additional leucine residue at the base of the structure (denoted as x), which can show that the inserted sequence could increase interactions between the I and H helices, stabilizing the thumb subdomain.

In further support of this model, Bst also has a small antiparallel beta sheet in this region (FIG. 6d, 3 black arrows) that is not observed in Klentaq, consisting of three interacting beta strands at the base of the I, H, and K helicies of the thumb domain. One beta strand contributing to this structure (FIG. 6d, left arrow) is contained in the inserted region in v5.9, while the other beta strands consist of identical or similar residues in both structures. Given this, the observed insertion could also enable the formation of a beta sheet at the base of the thumb subdomain in variant 5.9, which may involve the nearby E322G point mutation (FIG. 6c).

Overall, it appears that the Bst insertion observed in v5.9 stabilizes the structure of the thumb subdomain of the polymerase by extending the I alpha helix and allowing the formation of a beta sheet at the subdomain's base. This offers a new insight into the structural basis of strand displacement activity in polymerases, and with the finding that multiple crossovers in this region were observed in the library potentially provides a more direct path to engineering strand displacement in any polymerase.

(9) Selection Optimization

Designing a polymerase selection for strand displacement poses several unique challenges compared to typical CSR. First, no thermophilic polymerase has been shown to be capable of RCA. For this reason, initial optimization of the parameters and methods necessary for IsoCSR relied on enzymatic lysis with lysozyme to break open cells and plasmid DNA nicking using the Nb.BsmI restriction endonuclease (New England Biolabs) to initiate rolling circle amplification rather than heating to accommodate wild-type Bst LF. Enzymatic lysis was optimized by monitoring emulsified E. coli expressing GFP on an inverted fluorescent microscope. Emulsions held at 37° C. for 30 min for lysozyme digestion followed by heating at 65° C. for 30 min (simulating the RCA step) were fully lysed in emulsion bubbles, while those held at 4° C. with and without lysozyme for 60 min did not lyse (FIG. 14). Lysis was later shortened to 20 min, as this proved to be sufficient.

The emulsified nicking RCA mechanism for IsoCSR was first optimized without cells by including commercial Bst LF (New England Biolabs) and plasmid template in the emulsions, producing a characteristic RCA "smear" when analysed by gel electrophoresis. DNA was purified from the recovered emulsion by ethanol precipitation, as typical DNA columns are inefficient for purifying the large molecular weight products of RCA. Additionally, a DpnI digest (37° C. for 2 hr) was included after DNA recovery from emulsion RCA to reduce background from unamplified plasmids. Emulsion RCA product was unaffected by DpnI when analysed by gel electrophoresis, and the subsequent recovery PCR produced a band corresponding to the Bst gene product only when polymerase was included in the initial emulsion RCA.

These conditions were further refined to accommodate E. coli cells expressing Bst as a source for both plasmid template and polymerase, as cell lysate inhibited the combined nicking and RCA reaction. This was accomplished by increasing emulsion compartment size through reduction of the frequency of emulsification from 42 Hz to 35 Hz, as lower frequency emulsions were unstable. These larger emulsions were stable at 65° C. for 3 hr, sufficient for RCA in emulsio (FIG. 15). This optimization resulted in successful PCR recovery from emulsion RCA products generated from cellular polymerase and template, validating the IsoCSR mechanism. Further optimization benefited from including dUTPase to remove dUTP, a known Bst inhibitor, and increasing the volume of the aqueous component of the emulsions. In spite of these improvements, nicking IsoCSR was only able to recover wild-type Bst LF in 103 excess inactive mutant Bst (FIG. 2), likely due to the complex mechanism reliant on multiple enzymes to circumvent boiling and linear nature of RCA initiated from a single nick site on the plasmid template. For this reason, IsoCSR was adapted to accommodate hyperbranched RCA, enabling exponential amplification (Lizardi 1998; Zhang 2001; Zhao 2015).

c) Discussion

Compartmentalized self-replication (Ghadessy 2001) typically relies on multiple thermal cycling steps and has been used primarily with thermophilic polymerases to evolve novel functionalities. The development of IsoCSR is described herein, a directed evolution method that relies on self-replication of less thermostable strand-displacing polymerases. The Family A polymerases Bst LF and Klentaq were shuffled and the chimeric library was then iteratively challenged for the ability to carry out strand displacement polymerization following thermal challenge. Functional strand-displacing polymerases were still recovered from Rounds 5 and 7 (FIG. 3a) through the introduction of carefully tuned increases in selection pressure (in the form of reduced numbers of primers for amplification). The selection was successful in evolving v5.9, a thermostable polymerase with improved strand displacement capability. This chimera proved to be useful for carrying out hot start LAMP and a variety of high temperature RCA reactions.

During the development of isoCSR, a variety of experimental hurdles had to be overcome. In order to bridge the phylogenetic distance between Family A polymerases with desirable phenotypes was developed using Shuffle Optimizer, an open access algorithm that can be used to increase overlaps between distantly related DNA sequences for DNA shuffling. The exonuclease exoIII was used to eliminate small, off-target parasitic products that arose during PCR Finally, sequencing data showed that the polymerase library had become error-prone by Round 7 and in consequence "cheater" polymerases like v7.16 were recovered that survived the selection despite lacking thermostability, likely due to increased replication rate at the expense of fidelity. This has been seen in other CSR selections as well, and mutations that impact fidelity while retaining valuable new phenotypes can often be repaired through judicious reversion to wild-type residues.

IsoCSR is notable for being an emulsion-based selection that can allow large libraries to be sieved, but requires only a single thermal or enzymatic lysis step to accommodate both thermostable and mesophilic polymerases. Recently, Povilaitis and co-workers developed a similar isothermal, emulsion-based directed evolution scheme that relied on whole genome amplification (WGA) to evolve a phi29 polymerase mutant with slightly improved thermostability (up to 42° C.) and increased amplification rate. However, their selection required pre-emulsion treatment with lysozyme to lyse cells, a step that can lead to cross-contamination of variants before emulsified compartments are produced. Additionally, WGA necessitates the use of random primers and thus the burden of amplifying not only the gene of interest but genomic DNA. Over many cycles, this may hamper efficient self-amplification and lead to artefact production. In contrast, the IsoCSR selection requires only in emulsio lysozyme incubation or a single heating step to accomplish lysis (FIG. 1, FIG. 2), leaving cells intact prior to compartmentalization.

Variant 5.9 is useful for a variety of applications. The enzyme survived 1-2 min template denaturation steps at ~90° C., which were sufficient for complete template denaturation in LAMP assays. The ability to subject pre-assembled isothermal amplification reactions to high temperature incubations is be useful for diagnostic applications, as pre-reaction heating can improve assay sensitivity, reduce amplification inhibition from crude clinical samples, and serve as a nucleic acid extraction method for the direct detection of viruses and bacteria. Such "one pot" reactions can be especially useful for point of care applications, where the high temperature step could now be included in lab on a chip devices. Furthermore, variant 5.9 performed similarly or better than Bst LF in all the isothermal mechanisms tested; its superior performance in both standard linear RCA reactions and atypical hyperbranched RCA from supercoiled templates can actually make v5.9 preferable for many applications.

Variant 5.9 and its shuffled brethren also offered surprising insights into the structural and mechanistic properties that underlie the poorly understood process of strand displacement. For instance, it is significant that a polymerase known for strand displacement activity (Bst LF) is unable to amplify DNA from supercoiled plasmids using hyperbranched RCA, a mere 14 residue insertion of Bst LF into Klentaq alongside two point mutations enables this, as well as strand displacement sufficient for LAMP and relaxed template RCA reactions. The identification of this insertion can lay the foundation for understanding the structural basis for strand displacement, as it appears that small changes in the secondary structure at the base of Klentaq's thumb subdomain are sufficient to enable a versatile strand displacement phenotype.

IsoCSR can allow the directed evolution of many different polymerase phenotypes including altered nucleotide specificity, resistance to inhibitors, and the utilization of new templates. The initial selection optimization with wild-type Bst LF shows that lysozyme-mediated IsoCSR can be used to optimize multi-enzyme reactions, such as the polymerase and nickase together for RCA. Such co-optimizations can greatly improve diagnostic applications, whose efficiency can often be stymied by something as simple as a dissonance in buffer conditions between enzymes.

2. Example 2: Phosphorothioated Primers Lead to Loop-Mediated Isothermal Amplification at Low Temperatures a) Introduction In order to lower the operating temperature at which LAMP reactions can be carried out, a fundamental biophysical principle was exploited: the fact that phosphorothioate residues destabilize helices. Boczkowska and co-workers have carried out thermodynamic studies on the stability of duplexes formed between phosphorothioate (PS)-modified ssDNA and complementary phosphodiester (P0)-modified ssDNA (Boczkowska et al. 2002), and reported that the PS modifications substantially reduced the melting temperature of PS-PO dsDNA. This in turn allows more breathing at the termini of dsDNA, and can promote the formation of foldback hairpins for extension during LAMP. Based on this phenomenon, a different amplification method has been developed: phosphorothioated-terminal hairpin formation and self-priming extension (PS-THSP) (Jung 2016), in which the incorporation of phosphorothioate (PS) modifications lead to improved self-folding efficiency of terminal hairpins (LaPlanche 1986).

By incorporating phosphorothioate (PS) modifications into the foldback primers used for LAMP a more generic mechanism (PS-LAMP) has been created for low temperature amplification. PS-LAMP can operate at temperatures as low as 40° C. with sensitivities that are similar to regular LAMP. The PS-terminated DNA can also display enhanced stability against degradation by various nucleases that may be present in biological samples, further enhancing the applicability of PS-LAMP for point-of-care (POC) diagnostics.

b) Materials and Methods (1) Reagent

All chemicals were of analytical grade and were purchased from Sigma-Aldrich (St. Louis, Mo., U.S.A.) unless otherwise indicated. All enzymes including Bst 2.0 DNA polymerase, ET SSB and RecA were obtained from New England Biolabs (NEB, Ipswich, Mass., USA). Middle East respiratory syndrome (MERS) 1a, 1b and Neuropilin 2 (NRP2) DNA plasmid templates were generated as described previously (Jiang et al. 2017; Bhadra et al. 2015). Human genomic DNA was obtained from Promega (Madison, Wis., USA). All oligonucleotides were ordered from Integrated DNA Technology (IDT, Coralville, Iowa, U.S.A.). Oligonucleotide sequences are summarized in Table 4.

(2) One-Step Strand Displacement (OSD) Probe Preparation

An OSD stock solution was prepared by annealing 10 μM Reporter F with 50 μM Reporter Q in 1× Isothermal Buffer (20 mM Tris-HCl, 10 mM $(NH_4)_2SO_4$, 10 mM KCl, 2 mM $MgSO_4$, 0.1% Triton X-100, pH 8.8). The solution was incubated at 95° C. for 5 min followed by slow cooling to room temperature at a rate of 0.1° C./s. This OSD probe was then kept on ice before use.

(3) Real-Time LAMP with OSD Probe

In a typical experiment, reaction mixtures containing templates freshly diluted in specific copies, 20 pmol each BIP and FIP primers, 5 pmol each B3 and F3 primers, 10 pmol loop primer, 25 μmol betaine, 10 nmol dNTPs and 36 μmol urea in a total volume of 20 μL of 1× Isothermal Buffer (20 mM Tris-HCl, 10 mM $(NH_4)_2SO_4$, 10 mM KCl, 2 mM $MgSO_4$, 0.1% Triton X-100, pH 8.8) were heated to 95° C. for 5 min. The solutions were chilled on ice for 2 min, and then 5 μL stock solution containing an OSD reporter (at a final amount of 1.5 pmol Reporter F), 60 U of Bst 2.0 DNA polymerase and 0.5 μg of ET SSB (or certain amount of RecA) was added to initiate LAMP reactions. Subsequently, 25 μL of the LAMP-OSD solutions were transferred into a 96-well plate. The reactions were analyzed using the LightCycler 96 real-time PCR machine (Roche, Basel, Switzerland) that was set up to incubate the samples for 45/50/60 cycles of two-step incubations—step 1: incubation at 40/45/60/65° C. for 150 sec, step 2: incubation at 40/45/60/65° C. for 30 sec (total incubation time of 3 min/cycle unless otherwise indicated). The resulting data was analyzed using the LightCycler 96 analysis software to generate Cq (quantification cycle) values for each amplification and Cq was redefined as DT (detection time, min) by multiplying Cq by 3.

c) Results and Discussion (1) Design of PS-LAMP Reactions

Figure 21:
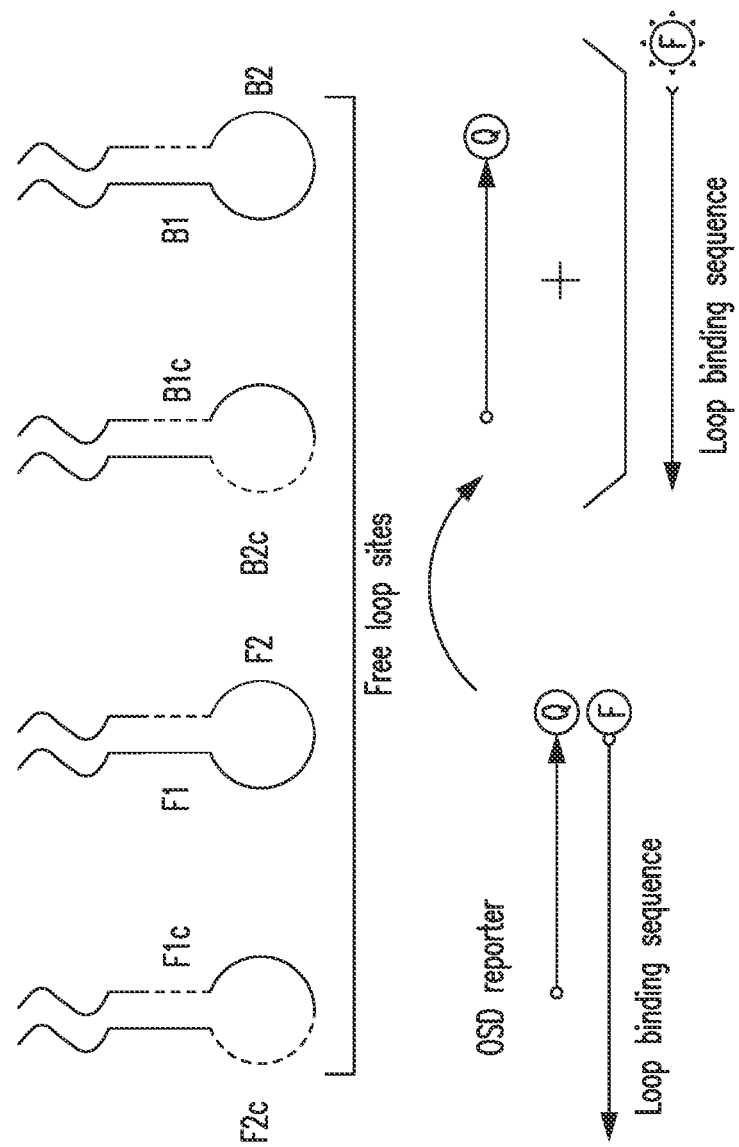
FIG. 21 shows the scheme of one-step strand displacement (OSD).

In a typical LAMP reaction (FIG. 1), there are at least four primers: two inner primers (FIP and BIP) and two outer primers (F3 and B3). These primers are specific to six consecutive blocks of target sequences: B3, B2, B1, F1c, F2c and F3c (from the 5'-end of the amplicon). Both the inner and outer primers anneal to the target template and are extended simultaneously. The extension of the outer primer with a strand displacing polymerase, such as Bst, therefore displaces the inner primer, which can then fold back on itself to create a dumbbell-shaped amplicon. The inner primers can hybridize to the single-stranded loops in the foldback structures and initiate another round of strand displacement synthesis, forming a concatamer amplicon with a self-priming 3'-hairpin. The ensuing exponential amplification during continuous strand displacement DNA synthesis generates increasingly complex, double-stranded concatamer amplicons. The single-stranded loops in these amplicons can be used to trigger sequence-specific strand exchange reporters, as we have previously described (FIG. 21) (Bhadra et al. 2015; Jiang et al. 2015). These reporters greatly reduce background signal and provide greater surety in the detection of LAMP amplicons.

The loop structure is key to the amplification mechanism in LAMP reactions. Attempts were made to improve the formation of the foldback structure in the extended dsDNA (red box) replication intermediate. All the internucleotide linkages in the F1c portion of the FIP primer (20 phosphates for MERS 1a and MERS 1b) and in the B1c portion of the BIP primer (23 and 21 phosphates for MERS 1a and MERS 1b, respectively) were modified with phosphorothioates (see also FIG. 16). The F2 region in FIP and the B2 region in BIP were excluded from phosphorothioate modification as this might have reduced priming efficiency. The PS modifications should lead to great reductions in thermal stability at the terminus of the extended dsDNA replication intermediates (Jung et a. 2016), and thus intrastrand hybridization (hairpin structure formation) can occur more readily, allowing more efficient exponential amplification and the execution of LAMP at lower reaction temperatures.

To verify that exponential amplification during PS-LAMP is more efficient than during regular LAMP, amplification performance was compared at two different temperatures, 60° C. and 65° C.). Amplification for LAMP and PS-LAMP was carried out identically except for the primers used, and was monitored in real-time using a sequence-specific strand exchange reporter for 150 min in the absence or presence of target template ($1.2 \times 10^8$ copies). FIG. 17a shows that at 60° C. LAMP could detect $1.2 \times 10^8$ molecules within about 22 min, while PS-LAMP required only 18 min to detect the same sample. At 65° C., the detection times for LAMP and PS-LAMP were similar (22 and 24 min, respectively). Interestingly, the fluorescence intensity of the PS-LAMP reaction at 150 min was 1.8 times higher than that of LAMP at 60° C. (FIG. 17b). This signal improvement at lower temperatures is consistent with our hypothesis that phosphorothioates improve the self-folding of loops.

(2) Optimization of Lower Temperature PS-LAMP Reactions

Given these results, attempts to further optimize PS-LAMP for even lower temperatures were made, which would also further its potential use as a point-of-care diagnostic. When PS-LAMP was performed at progressively lower temperatures (60, 55, 50 and 45° C.) no amplification was eventually observed at 45° C. (FIG. 24a). The buffer and reaction conditions (4 mM of $MgSO_4$ and 8 U of Bst 2.0 DNA polymerase) were therefore further optimized at 45° C. to see if a signal could be generated. Magnesium ions are known to greatly impact self-folding (Zahran 2011; Sissi et al. 2009), and thus different concentrations of magnesium (0, 1, 2, 3 and 4 mM) were assessed. At 2 mM $MgSO_4$, a small signal increase was observed (FIG. 24b). The amount of Bst 2.0 DNA polymerase was then increased from 8 U to 12 U and a thermostable single-stranded DNA binding protein (ET SSB) was added (0.5 μg) to further destabilize duplexes and promote self-folding at the termini (27-30). ET SSB proved more effective than an alternative single-stranded DNA binding protein, RecA (FIG. 23).

Using the optimized reaction conditions (FIG. 22), template amplification by PS-LAMP was possible at 45° C., while normal LAMP reactions showed no amplification at this temperature (FIG. 17c). That said, optimized PS-LAMP at 45° C. still took a longer time (63 min) to come to completion than did a normal LAMP reaction at a higher temperatures (65° C., 22 min).

To further lower the operational temperature of PS-LAMP, urea was added to the reaction mixture. Like heat and phosphorothioates, urea can disrupt base stacking and again improve the possibility of foldback priming (Singer et al. 2010; Conway et al. 1956; Schwinefus et al. 2013). Upon optimization, a urea concentration of 1.44 M yielded a workable PS-LAMP reaction at 40° C. (FIGS. 18a and 18b). Both urea and low temperatures decrease Bst 2.0 DNA polymerase activity, and thus the amount of Bst 2.0 DNA polymerase in the reaction was optimized once again, as shown in FIGS. 318c and 18d, and subsequent reactions contained 60 U of polymerase; higher concentrations (80 U and 120 U) inhibited the reaction. At optimal urea and polymerase concentrations, ET SSB and $MgSO_4$ were re-optimized (0.5 μg and 2 mM, respectively (FIG. 19), further decreasing the detection time from approximately 117 to 70 min.

(3) Selectivity

Figures 25, 26A:
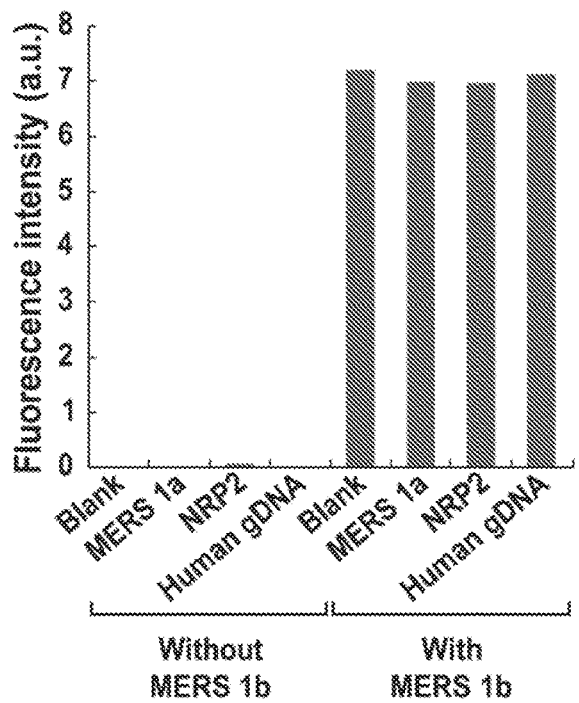

To validate the sequence-specificity of PS-LAMP, various non-target templates (MERS 1a, NRP2 and human genomic DNA) were tested in parallel with the target template (MERS 1b). As indicated in FIG. 25, at template concentrations of 500 μg (1.2×10⁸ copies) PS-LAMP produced negligible responses with non-cognate templates. When the target amplicon (MERS 1b) was mixed with the non-complementary templates, no diminution in positive signal was observed (FIG. 25).

(4) Quantitation by PS-LAMP

The quantitative behavior of PS-LAMP at 40° C. in the presence of urea and under fully optimized conditions was analyzed by monitoring the changes in the fluorescence intensity of the OSD reporter as a function of template concentration. As shown in FIG. 20, when plasmids bearing the MERS 1b and MERS 1a genes were used as targets, as few as 4,800 molecules and 12 molecules, respectively, could be successfully detected within 110 min and 80 min by PS-LAMP. The detection of the MERS 1a amplicon was roughly comparable with regular LAMP at 65° C., but detection of the MERS 1b amplicon with PS-LAMP at 40° C. was less sensitive than for regular LAMP at 65° C. (24 molecules within 30 min) (FIG. 20). This is not surprising, as there can be wide variation in the detection limits for different amplicons even with regular LAMP, depending upon the sequences of primers and templates, and as the PS-LAMP technique is further developed it should be possible to identify comparable optimization rules for amplicon choice and primer design.

d) Conclusions

LAMP is an ultrasensitive nucleic acid amplification method that can often detect small numbers DNA or RNA templates within roughly an hour. However, the requirement for high temperatures limits it applicability, and nucleic acid hybridization chemistry, along with the disruption of helical stability by phosphorothioates have been relied upon to develop PS-LAMP, which shows comparable sensitivities even down to 40° C. Operating at lower temperatures can inherently reduce device complexity and power consumption when adapting molecular diagnostics to microscale or portable devices.

In addition to being able to operate at more moderate temperatures, PS-LAMP can better enable the use of degenerate primer sets to capture a wider range of phylogenetic variants into amplicons. Improving amplification at lower temperatures also enables the use of AT-rich primers and probes, which have previously proven problematic for LAMP (Tomita 2008).

Overall, PS-LAMP can now allow mesothermal amplification and concomitant applications in molecular diagnostics that should be on par with similar techniques, such as RPA. As the technique is further developed, the development of primer design rules that accommodate lower temperatures and phosphorothioates can increase its overall applicability, and the ability to 'dial in' amplicon acquisition via the number of phosphorothioates, the amount of urea present, and the temperature of the reaction provides much greater experimental control over the amplification and detection of specific targets.

Example 3: Zika RNA and PS-LAMP

PS-LAMP is ideal for use with amplifying RNA from Zika virus. Below are the nucleic acids used with the polymerase for amplifying Zika:

```
zkNS5: (SEQ ID NO: 6)
CTAGTAACGGCCGCCAGTGTGCTGGAATTCGGTAGATCCATTGTGGTCC

CTTGCCGCCACCAAGATGAATTGATTGGCCGAGCCCGTGTATCACCAGG

GGCAGGATGGAGCATTCGGGAGACTGCCTGTCTAGCAAAATCATATGCA

CAGATGTGGCAGCTTCTTTACTTCCACAGAAGAGACCTTCGACTGATGG

CCAATGCTATTTGTTCGGCTGTGCCAGTTGACTGGGTACCAACCGGGAG

AACCACCTGGTCAATCCACGGAAAGGGAGAATGGATGACTACTGAGGAC

ATGCTCATGGTGTGGAATAGAGTGTGGATTGAGGAGGAATTCTGCAGAT

ATCCATCACACTGGCGGCCGCTCGAGC
```

-continued zk.B3.dalt: (SEQ ID NO: 7)
GTCATCCARTCTCCRTTRCC zk.F3.1d (SEQ ID NO: 8):
ATCCATTGTGGTYCCYTGY zk.LR.1d (SEQ ID NO: 9)
TGCTCCATCCYGCCCCYGGHGA zk.BIP.1daltPS: (SEQ ID NO: 10):
A*T*G*C*V*C*A*R*A*T*G*T*G*G*C*A*G*C*T*Y*C*T*TCC

CHG TTG GNA CCC A

-continued zk.FIP.1dPS (SEQ ID NO: 11)
G*C*H*A*G*R*C*A*R*G*C*A*G*T*C*T*C*M*C*G*R*GATGAAY

TGATTGGCCGRGC

Figures 26A, 26B:
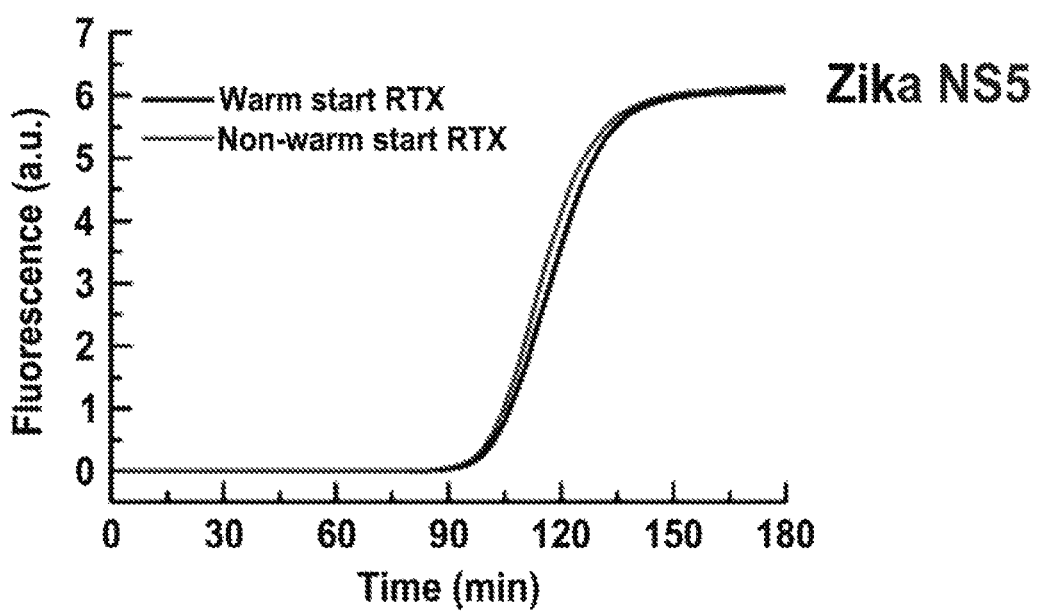
Figure 26B:
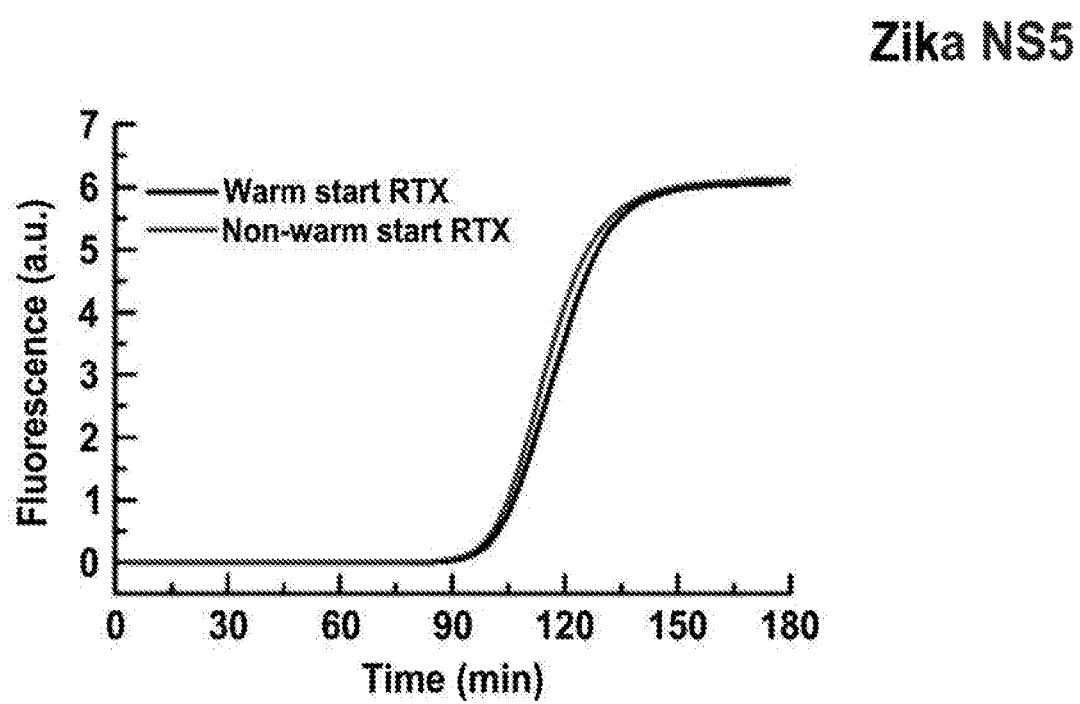
Figure 26D:
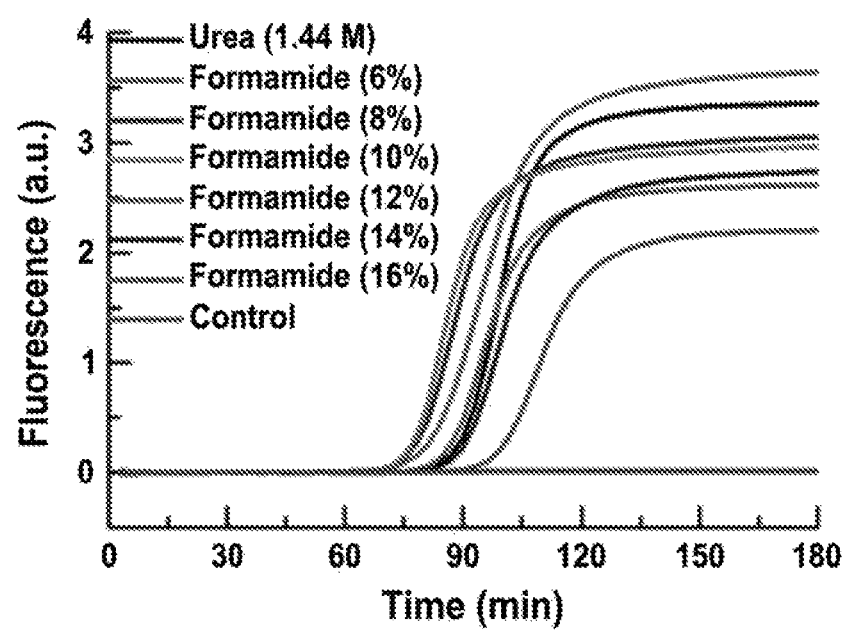
Figure 27B:
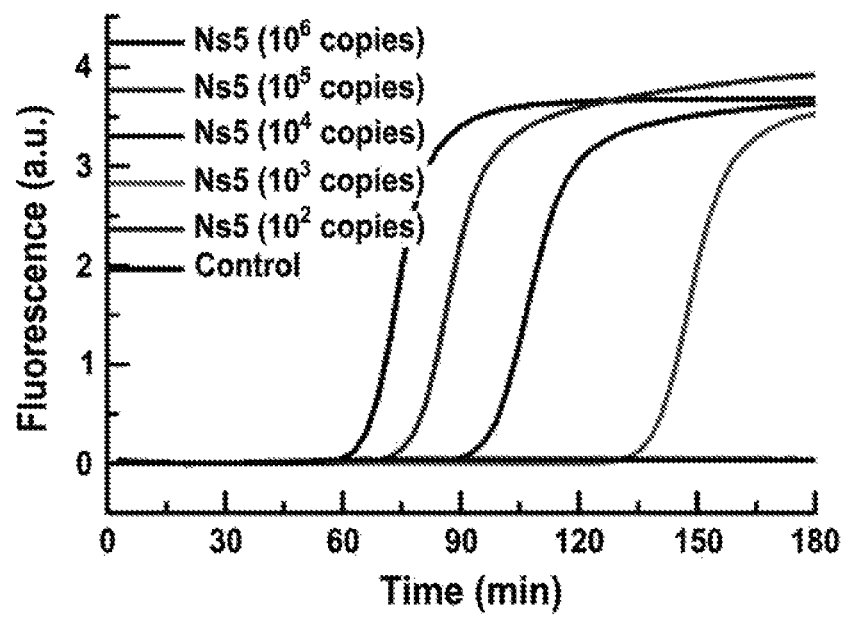
Figure 27C:
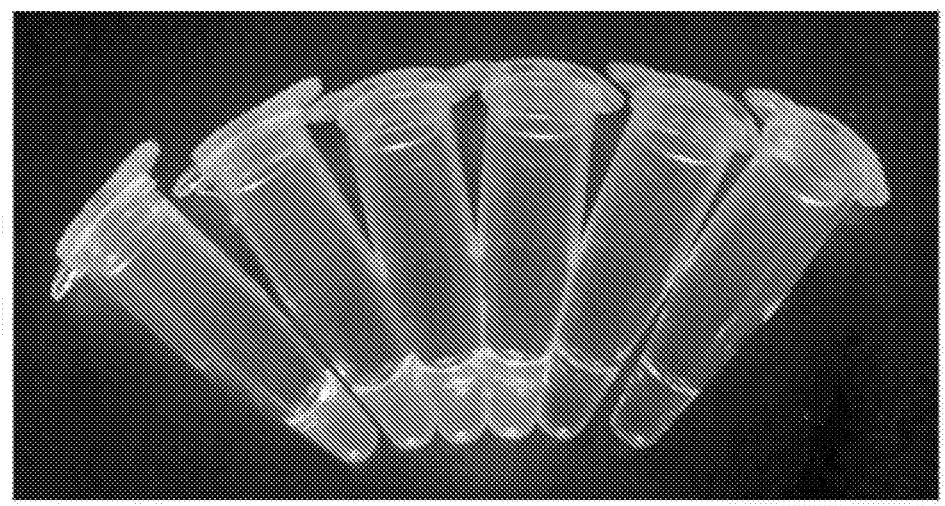

FIGS. 26A-D show optimization of RTX polymerase. Denaturation was carried out at 65° C. for 5 minutes, then samples were transferred on ice for at least two minutes. The temperature of amplification was 42 C for 3 hours. FIGS. 26A and B compare the performance of non-warm start RTX and warm-start RTX in urea condition for zika NS5. FIGS. 26C and 26D show formamide optimization. The best concentration of formamide was shown to be 8%. FIG. 27 shows the final experimental protocol and results. Formamide was used at 8%.

D. TABLES

TABLE 1

Primers used for PCR, sequencing, cloning, and RCA of Thermostable Polymerase design. All Primers written in 5' to 3' orientation. Selection primers were used in hbRCA as indicated. Primers are numbered consecutively as SEQ ID NO: 12-21 for JNM101, JNM135, JNM141, JNM219-222, JNM245, JNM258, and JNM259. Primers are numbered consecutively as SEQ ID NO: 22-41 for JNM264-JNM283. Primers are numbered consecutively as SEQ ID NOS: 42-45 for JNM309, JNM310, JNM316, and JNM317.

JNM101 TTTTCGTGTGAATATCAAGATCGC

JNM135 TTAGAAAAATAAACAAATAGGGGTTCCGCGCACATTTCC
CGGGAACTGCCAGACATCAAATAAAACAAAGGC

JNM141 CTGGCCTTTTGCTCACATGACCCGACACCATCGAATGGCC
GACAGTCATTCATCTTTCTGCC

JNM219 CAGACCCTAATTTCACATCATATGAC

JNM220 CTTTTGCTCACATGACCCGA

JNM221 GTTTAACTTTAAGAAGGAGTAGGATCC

JNM222 GAGGACAGAATTTGAATGCAAGC

JNM245 GCGATACAGACCCTAATTTCACATCATATGACAC

JNM258 GTTCCTGAGAAAGACGGTGAGCG

JNM259 CGGGTTTTTACGTAAATCAGGTG

| hbRCA Primers (alternating F and R) | Used in 20 primer RCA (10F, 10R) | Used in 10 primer RCA (5F, 5R) | Used in 2 primer RCA (1F, 1R) |
|---|---|---|---|
| JNM264 AAGCTTGCATTCAAATTCTGTCCTCAAG | xx | xx | xx |
| JNM265 GGCCTTTTGCTCACATGACCC | xx | | |
| JNM266 GGACTATAAAGATACCAGGCGTTTCC | xx | | |
| JNM267 GAACGACCTACACCGAACTGAGATAC | xx | xx | |
| JNM268 GCAGCAGCCACTGGTAACAG | xx | xx | |
| JNM269 CGGATCAAGAGCTACCAACTCTTTTTC | xx | | |
| JNM270 CTCAGTGGAACGAAAACTCACGTTAAG | xx | | |
| JNM271 CCTTGAATTGATCATATGCGGATTAGAAAAACAAC | xx | xx | |
| JNM272 CTTTAGCGACTTGATGCTCTTGATCTTC | xx | xx | |
| JNM273 GTACACGGCCTACAGAAAAACAGTATG | xx | | |
| JNM274 GTATGGTGCCTATCTAACATCTCAATG | xx | | |
| JNM275 CAGCGCATTAGAGCTGCTTAATGAGG | xx | xx | |

TABLE 1-continued

Primers used for PCR, sequencing, cloning, and RCA of Thermostable Polymerase design. All Primers written in 5' to 3' orientation. Selection primers were used in hbRCA as indicated. Primers are numbered consecutively as SEQ ID NO: 12-21 for JNM101, JNM135, JNM141, JNM219-222, JNM245, JNM258, and JNM259. Primers are numbered consecutively as SEQ ID NO: 22-41 for JNM264-JNM283. Primers are numbered consecutively as SEQ ID NOS: 42-45 for JNM309, JNM310, JNM316, and JNM317.

| | | | | |
|---|---|---|---|---|
| JNM276 | CTCCCCGTCGTGTAGATAACTACG | xx | xx | |
| JNM277 | CGGATAAAGTTGCAGGACCACTTC | xx | | |
| JNM278 | CGTTTGGTATGGCTTCATTCAGCTC | xx | | |
| JNM279 | CAGTGCTGCCATAACCATGAGTG | xx | xx | |
| JNM280 | CAATACGGGATAATACCGCGCCA | xx | xx | |
| JNM281 | GCTGGTGAAAGTAAAAGATGCTGAAGATC | xx | | |
| JNM282 | CAGGGTTATTGTCTCATGAGCGGATAC | xx | | |
| JNM283 | GAGTGTTCACCGACAAACAACAGATAAAAC | xx | xx | xx |
| JNM309 | CGCTTGAGGACAGAATTTTGGCAGAGCICAATTATCATTTCGCATCGTACCAAGTACTTC | | | |
| JNM310 | CGCTTGAGGACAGAATTTTGGCAGAGGCAATTATCATTCTTTCGCAGATAACCAATCTTC | | | |
| JNM316 | TTTGTTTAACTTTAAGAAGGAGATATACATATGGCTAGCAGAGGATCGCATCACCATCACCATCACATCGAAGGGCGCGAAAGTCCCAGCAGCGAG | | | |
| JNM317 | TTTGTTTAACTTTAAGAAGGAGATATACATATGGCTAGCAGAGGATCGCATCACCATCACCATCACATCGAAGGGCGCCTTCTTCACGAGTTCGGAC | | | |

TABLE 2

Primers and template used for gLAMP reactions for thermostable polymerase design. Primers are numbered consecutively as SEQ ID NO: 46-51 in the table below.

| | |
|---|---|
| F3 | GCCACCCAGAAGACTGTG |
| B3 | TGGCAGGTTTTTCTAGACGG |
| FIP | CGCCAGTAGAGGCAGGGATGAGGGAAACTGTGGCGTGAT |
| BIP | GGTCATCCCTGAGCTGAACGGTCAGGTCCACCACTGACAC |
| LR | TGTTCTGGAGAGCCCCGCGGCC |
| GAPDH (Template) | CTAGTAACGGCCGCCAGTGTGCTGGAATTCCCACAGTCCATGCCATCACTGCCACCCAGAAGACTGTGGATGGCCCCTCCGGGAAACTGTGGCGTGATGGCCGCGGGGCTCTCCAGAACATCATCCCTGCCTCTACTGGCGCTGCCAAGGCTGTGGGCAAGGTCATCCCTGAGCTGAACGGGAAGCTCACTGGCATGGCCTTCCGTGTCCCCACTGCCAACGTGTCAGTGGTGGACCTGACCTGCCGTCTAGAAAAACCTGCCAAAATATGATGACATCAAGAAGGTGGTGAAGCAGGCGTCGGAGGGCCCCCTCAAGGGCATCCTGGGCTACACTGAGCACCAGGTGGTCTCCTCTGACTTCAACAGCGACACCCACTCCTCCACCTTTGACGCTGGGGCTGGCATTGCCCTCAACGACCACTTTGTCAAGCTCATTTCCTGGAATTCTGCAGATATCCATCACACTGGCGGCCGCTCGAGC |

TABLE 3

Oligonucleotide Sequences for PS-LAMP.

MERS 1b primers

| | |
|---|---|
| Template | TAATACGACTCACTATAGGGCGTGAATCTTAATTTACCCGCAAATGTCCCATACTCTCGTGTTATTTCCAGGATGGGCTTTAAACTCGATGCAACAGTTCCTGGATATCCTAAGCTTTTCATTACTCGTGAAGAGGCTGTAAGGCAAGTTCGAAGCTGGATAGGCTTCGATGTTGAGGGTGCTCATGCTTCCCGTAATGCATGTGGCACCAATGTGCCTCTACAATTAGGATTTTCAACTGGTGTGAACTTTGTTGTTCAGCCAGTTGGTGTTGTAGACACTGAGTCCTGACGAGTGGGTTTAACG (SEQ ID NO: 52) |
| F3 | ACAGTTCCTGGATATCCTAAG (SEQ ID NO: 53) |
| B3 | CTCAGTGTCTACAACACCA (SEQ ID NO: 54) |
| FIP | AGCACCCTCAACATCGAAGCACTCGTGAAGAGGCTGTA (SEQ ID NO: 55) |
| BIP | TGCTTCCCGTAATGCATGTGGACTGGCTGAACAACAAAGT (SEQ ID NO: 56) |
| Loop | CTATCCAGCTTCGAACTTGCCT (SEQ ID NO: 57) |
| OSD-F | /56FAM/CACACCAGTTGAAAATCCTAATTGTAGAGGCACATTGGTG/3InvdT/ (SEQ ID NO: 58) |
| OSD-Q | CTCTACAATTAGGATTTTCAACTGGTGTG/3IABkFQ/ (SEQ ID NO: 59) |

MERS 1a primers

| | |
|---|---|
| Template | TAATACGACTCACTATAGGGCTTGTGACTATGGCTTCGTTATGTTGTTGGTTAAACACAAACACACCTTTTTGACACTTTTCTTGTTGCCTGTGGCTATTTGTTTGACTTATGCAAACATAGTCTACGAGCCCACTACTCCCATTTCGTCAGCGCTGATTGCAGTTGCAAATTGGCTTGCCCCCACTAATGCTT |

TABLE 3-continued

Oligonucleotide Sequences for PS-LAMP.

|   | |
|---|---|
| | ATATGCGCACTACACATACTGATATTGGTGTCTACATTA GTATGTCACTTGTATTAGTCATTGTAGTGAAGAGATTGT ACAACCCATCACTTTCTAACTTTGCGTTAGCATTGTGCA GTGGTGTAATGTGGTTGTACACTTATAGCATTGGAGAAG CCTGACGAGTGGGTTTAACG (SEQ ID NO: 60) |
| F3 | TTATGCAAACATAGTCTACGAG (SEQ ID NO: 61) |
| B3 | CGCAAAGTTAGAAAGTGATGG (SEQ ID NO: 62) |
| FIP | AAGCATTAGTGGGGGCAAGCCCCACTACTCCCATTTCG (SEQ ID NO: 63) |
| BIP | ATGCGCACTACACATACTGATATTTGTQACAATCTCTTC ACTACAATGA (SEQ ID NO: 64) |
| Loop | GGTGTCTACATTAGTATGTCACTTGTATTAG (SEQ ID NO: 65) |
| OSD-F | /56FAM/CGAAGCCAATTTGCAACTGCAATCAGCGCTGA G/3InvdT/ (SEQ ID NO: 66) |
| OSD-Q | ATTGCAGTTGCAAATTGGCTTCG/3IABkFQ/ (SEQ ID NO: 67) |
| Template | CACTCATTGGCACAGTGGTAGTTAGAGGTGAAAAGTAGA GCTGTCAAGCCCAAGGGCTTAGCTTTAGGGCTCCTCCTG AGTTCGGCCCACAGTAGAAGCAAGATTTTAACTAGCCCC TTTTCCTCTTCACCCTCCCATGATGCGCAGTGTTCAGAA AGCTGGTAAGTCCTAGGGATTTCCAGAAGTAGCCTGCAG AAGAAGGTAAGTTTGAAAGCCACTCCAGGGGTCCTGATG CTGTCATGCTCAGTGAGCCATTTTAQCAGTTCTCCAAAG TCTAGCCCTGTTTCGGACCTGCACTTCACCTCTAAGTTA TGTACAACTCAACC (SEQ ID NO: 68) |

*Underlining indicates phosphorothioate (PS) modifications.

E. POLYMERASE SEQUENCES

Primers used for PCR, sequencing, cloning, and RCA. All Primers written in 5' to 3' orientation. Selection primers were used in hbRCA as indicated.

SEQ ID NO: 3:
MESPSSEEEKPLAKMAFTLADRVTEEMLADKAALVVEVVEENYHDAPIV

GIAVVNHEGRFFLRPETALADPQFVAWLGDETKKKSMFDSKRAAVALKW

KGIELCGVSFDLLLAAYLLDPAQGVDDVAAAAKMKQYEAVRPDEAVYGK

GAKRAVPDEPVLAEHLVRKAAAIWELERPFLDELRRNEQDRLLVELEQP

LSSSILAEMEFAGVKVDTKRLEQMGKELAEQLGTVEQRIYELAGQEFNIN

SPKQLGVILFEKLQLPVLKKTKTGYSTSADVLEKLAPYHEIVENILHYR

QLGKLQSTYIEGLLKVVRPDTKKVHTIFNQALTQTGRLSSTEPNLQNIP

IRLEEGRKIRQAFVPSESDWILFAADYSQIELRVLAHIAEDDNLMEAFR

RDLDIHTKTAMDIFQVSEDEVTPNMRRQAKAVNFGIVYGISDYGLAQNL

NISRKEAAEFIERYFESFPGVKRYMENIVQEAKQKGYVTTLLHRRRYLP

DITSRNFNVRSFAERMAMNTPIQGSAADIIKKAMIDLNARLKEERLQAH

LLLVQHDELILEAPKEEMERLCRLVPEVMEQAVTLRVPLKVDYHYGSTW

YDAK

Klentaq (SEQ ID NO: 4)
MLLHEFGLLESPKALEEAPWPPPEGAFVGFVLSRKEPMWADLLALAAAR

GGRVHRAPEPYKALRDLKEARGLLAKDLSVLALREGLGLPPGDDPMLLA

YLLDPSNTTPEGVARRYGGEWTEEAGERAALSERLFANLWGRLEGEERL

LWLYREVERPLSAVLAHMEATGVRLDVAYLRALSLEVAEEIARLEAEVF

RLAGHPFNLNSRDQLERVLFDELGLPAIGKTEKTGKRSTSAAVLEALRE

AHPIVEKILQYRELTKLKSTYIDPLPDLIHPRTGRLHTRFNQTATATGR

LSSSDPNLQNIPVRTPLGQRIRRAFIAEEGWLLVALDYSQIELRVLAHL

SGDENLIRVFQEGRDIHTETASWMFGVPREAVDPLMRRAAKTINFGVLY

GMSAHRLSQELAIPYEEAQAFIERYFQSFPKVRAWIEKTLEEGRRRGYV

ETLFGRRRYVPDLEARVKSVREAAERMAFNMPVQGTAADLMKLAMVKLF

PRLEEMGARMLLQVHDELVLEAPKERAEAVARLAKEVMEGVYPLAVPLE

VEVGIGEDWLSAKE

Variant 5.9 (v5.9) (SEQ ID NO: 1)
MASRGSHHHHHHIEGRLLHEFGLLESPKALEEAPWPPPEGAFVGFVLSR

KEPMWADLLALAAARGGRVHRAPEPYKALRDLKEARGLLAKDLSVLALR

EGLGLPPGDDPMLLAYLLDPSNTTPEGVARRYGGEWTEEAGERAALSER

LFANLWGRLEGEERLLWLYREVERPLSAVLAHMEATGVRLDVAYLRALS

LEVAEEIARLEAEVFRLAGHPFNLNSRDQLERVLFDELGLPAIGKTEKT

GKRSTSAAVLEALREAHPIVEKILQYRELTKLKSTYIEGLLKVVRPDTK

KVHTRFNQTATATGRLSSSDPNLQNIPVRTPLGQRIRRAFIAGEGWLLV

ALDYSQIELRVLAHLSGDENLIRVFQEGRDIHTETASWMFGVPREAVDP

LMRRAAKTINFGVLYGMSAHRLSQELAIPYEEAQAFIERYFQSFPKVRA

WIEKTLEEGRRRGYVETLFGRRRYVPDLEARVKSVREAAERMAFNMPVQ

GTAADLMKSAMVKLFPRLEEMGARMLLQVHDELVLEAPKERAEAVARLA

KEMEGVYPLAVPLEVEVGIGEDWLSAKE

Nucleic Acid Encoding Variant 5.9 (v5.9)
(SEQ ID NO: 2)
atggcgagccgcggcagccatcatcatcatcatcatattgaaggccgcc tgctgcatgaatttggcctgctgaaaagcccgaaagcgctggaagaagc gccgtggccgccgccggaaggcgcgtttgtgggctttgtgctgagccgc aaagaaccgatgtgggcggatctgctggcgctggcggcggcgcgcggcg gccgcgtgcatcgcgcgccggaaccgtataaagcgctgcgcgatctgaa agaagcgcgcggcctgctggcgaaagatctgagcgtgctggcgctgcgc gaaggcctgggcctgccgccgggcgatgatccgatgctgctggcgtatc tgctggatccgagcaacaccaccccggaaggcgtggcgcgccgctatgg cggcgaatggaccgaagaagcgggcgaacgcgcggcgctgagcgaacgc ctgtttgcgaacctgtggggccgcctggaaggcgaagaacgcctgctgt ggctgtatcgcgaagtggaacgcccgctgagcgcggtgctggcgcatat ggaagcgaccggcgtgcgcctggatgtggcgtatctgcgcgcgctgagc ctggaagtggcggaagaaattgcgcgcctggaagcggaagtgtttcgcc tggcggccatccgtttaacctgaacagccgcgatcagctggaacgcgt gctgtttgatgaactgggcctgccggcgattggcaaaaccgaaaaaacc ggcaaacgcagcaccagcgcggcggtgctggaagcgctgcgcgaagcgc atccgattgtggaaaaaattctgcagtatcgcgaactgaccaaactgaa

```
-continued
aagcacctatattgaaggcctgctgaaagtggtgcgcccggataccaaa aaagtgcatacccgctttaaccagaccgcgaccgcgaccggccgcctga gcagcagcgatccgaacctgcagaacattccggtgcgcacccgctggg ccagcgcattcgccgcgcgtttattgcgggcgaaggctggctgctggtg gcgctggattatagccagattgaactgcgcgtgctggcgcatctgagcg gcgatgaaaacctgattcgcgtgtttcaggaaggccgcgatattcatac cgaaaccgcgagctggatgtttggcgtgccgcgcgaagcggtggatccg ctgatgcgccgcgcggcgaaaaccattaactttggcgtgctgtatggca tgagcgcgcatcgcctgagccaggaactggcgattccgtatgaagaagc gcaggcgtttattgaacgctattttcagagctttccgaaagtgcgcgcg tggattgaaaaaacccctggaagaaggccgccgccgcggctatgtggaaa ccctgtttggccgccgccgctatgtgccggatctggaagcgcgcgtgaa aagcgtgcgcgaagcggcggaacgcatggcgtttaacatgccggtgcag ggcaccgcggcggatctgatgaaaagcgcgatggtgaaactgtttccgc gcctggaagaaatgggcgcgcgcatgctgctgcaggtgcatgatgaact ggtgctggaagcgccgaaagaacgcgcggaagcggtggcgcgcctggcg aaagaagtgatggaaggcgtgtatccgctggcggtgccgctggaagtgg aagtgggcattggcgaagattggctgagcgcgaaagaa Variant 7.16 (v7.16) (SEQ ID NO: 5)
MESPSSEEEKPLAKMAFTLADRVTEEMLADKAALVVEVVEENYHDAPIV

GIAVVNHEGRFFLRPETALADPQFVAWLGDETKKKSMFDSKRAAVALKW

KGIELCGVSFDLLLAAYLLDPAQGVDDVAAAAKMKQYEAVRPDEAVYGK

GAKRAVPDEPVLAEHLVRKAAAIWELERPFLDELRRNEQDRLLVELEQP

LSSILAEMEFAGVKVDTKRLEQMGKELAGQLGTVEQRIYELAGQEFNIN

SPKRLGVILFEKLQLPVLKKTKTGYSTSADVLEKLAPYHEIVENILHYR

QLGKLQSTYIEGLLKVVRPDTKKVHTIFNQALTQTGRLSSTEPNLQNIP

IRLEEGRKIRQAFVPSESDWILFAADYSQIELRVLAHIAEDDNLMEAFR

RDLDIHTKTAMDIFQVSEDEVTPSMRRQAKAVNFGIVYGISDYGLAWNL

NISRKEAAEFIGRYFESFPGVKRYMENIVQEAKQKGYVTTLLHRRRYLP

DITSRNFNVRSFAERMAMNTPIQGSAADIIKKAMIDLNARLKEERLQAH

LLLQVHDELILEAPKEEMERLCRLVPEVMEQAVTLRVPLKVDYHYGSTW

YDAK
```

F. REFERENCES

1. Reference List #1

1. Craw, P. and Balachandran, W. (2012) Isothermal nucleic acid amplification technologies for point-of-care diagnostics: a critical review. *Lab on a chip*, 12, 2469-2486.
2. Hartman, M. R., Ruiz, R. C., Hamada, S., Xu, C., Yancey, K. G., Yu, Y., Han, W. and Luo, D. (2013) Point-of-care nucleic acid detection using nanotechnology. *Nanoscale*, 5, 10141-10154.
3. Gill, P. and Ghaemi, A. (2008) Nucleic Acid Isothermal Amplification Technologies—A Review. *Nucleosides, Nucleotides & Nucleic Acids*, 27, 224-243.
4. Mori, Y., Kanda, H. and Notomi, T. (2013) Loop-mediated isothermal amplification (LAMP): recent progress in research and development. *J Infect Chemother*, 19, 404-411.
5. Njiru, Z. K. (2012) Loop-mediated isothermal amplification technology: towards point of care diagnostics. *PLoS Negl Trop Dis*, 6, e1572.
6. Zhao, Y., Chen, F., Li, Q., Wang, L. and Fan, C. (2015) Isothermal Amplification of Nucleic Acids. *Chemical reviews*, 115, 12491-12545.
7. Asiello, P. J. and Baeumner, A. J. (2011) Miniaturized isothermal nucleic acid amplification, a review. *Lab on a chip*, 11, 1420-1430.
8. Du, Y., Hughes, R. A., Bhadra, S., Jiang, Y. S., Ellington, A. D. and Li, B. (2015) A Sweet Spot for Molecular Diagnostics: Coupling Isothermal Amplification and Strand Exchange Circuits to Glucometers. *Sci Rep*, 5, 11039.
9. Jiang, Y. S., Bhadra, S., Li, B., Wu, Y. R., Milligan, J. N. and Ellington, A. D. (2015) Robust strand exchange reactions for the sequence-specific, real-time detection of nucleic Acid amplicons. *Analytical chemistry*, 87, 3314-3320.
10. Notomi, T., Okayama, H., Masubuchi, H., Yonekawa, T., Watanabe, K., Amino, N. and Hase, T. (2000) Loop-mediated isothermal amplification of DNA. *Nucleic acids research*, 28, E63.
11. Dean, F. B., Nelson, J. R., Giesler, T. L. and Lasken, R. S. (2001) Rapid amplification of plasmid and phage DNA using Phi 29 DNA polymerase and multiply-primed rolling circle amplification. *Genome Res*, 11, 1095-1099.
12. Jiang, Y. S., Li, B., Milligan, J. N., Bhadra, S. and Ellington, A. D. (2013) Real-time detection of isothermal amplification reactions with thermostable catalytic hairpin assembly. *Journal of the American Chemical Society*, 135, 7430-7433.
13. Lizardi, P. M., Huang, X., Zhu, Z., Bray-Ward, P., Thomas, D. C. and Ward, D. C. (1998) Mutation detection and single-molecule counting using isothermal rolling-circle amplification. *Nature genetics*, 19, 225-232.
14. Zhang, D. Y., Zhang, W., Li, X. and Konomi, Y. (2001) Detection of rare DNA targets by isothermal ramification amplification. *Gene*, 274, 209-216.
15. Bhadra, S., Jiang, Y. S., Kumar, M. R., Johnson, R. F., Hensley, L. E. and Ellington, A. D. (2015) Real-Time Sequence-Validated Loop-Mediated Isothermal Amplification Assays for Detection of Middle East Respiratory Syndrome Coronavirus (MERS-CoV). *PloS one*, 10, e0123126.
16. Kiefer, J. R., Mao, C., Hansen, C. J., Basehore, S. L., Hogrefe, H. H., Braman, J. C. and Beese, L. S. (1997) Crystal structure of a thermostable *Bacillus* DNA polymerase I large fragment at 2.1 A resolution. *Structure*, 5, 95-108.
17. Blanco, L. and Salas, M. (1984) Characterization and purification of a phage phi 29-encoded DNA polymerase required for the initiation of replication. *Proceedings of the National Academy of Sciences of the United States of America*, 81, 5325-5329.
18. Blanco, L., Bernad, A., Lazaro, J. M., Martin, G., Garmendia, C. and Salas, M. (1989) Highly efficient DNA synthesis by the phage phi 29 DNA polymerase. Symmetrical mode of DNA replication. *The Journal of biological chemistry*, 264, 8935-8940.
19. McClary, J., Ye, S. Y., Hong, G. F. and Witney, F. (1991) Sequencing with the large fragment of DNA polymerase I from *Bacillus stearothermophilus*. *DNA Seq*, 1, 173-180.

20. Ye, S. Y. and Hong, G. F. (1987) Heat-stable. DNA polymerase I large fragment resolves hairpin structure in DNA sequencing. *Sci Sin B*, 30, 503-506.
21. Zhang, K., Martiny, A. C., Reppas, N. B., Barry, K. W., Malek, J., Chisholm, S. W. and Church, G. M. (2006) Sequencing genomes from single cells by polymerase cloning. *Nature biotechnology*, 24, 680-686.
22. Hsieh, K., Mage, P. L., Csordas, A. T., Eisenstein, M. and Soh, H. T. (2014) Simultaneous elimination of carryover contamination and detection of DNA with uracil-DNA-glycosylase-supplemented loop-mediated isothermal amplification (UDG-LAMP). *Chemical communications*, 50, 3747-3749.
23. Njiru, Z. K., Mikosza, A. S., Matovu, E., Enyaru, J. C., Ouma, J. O., Kibona, S. N., Thompson, R. C. and Ndung'u, J. M. (2008) African trypanosomiasis: sensitive and rapid detection of the sub-genus Trypanozoon by loop-mediated isothermal amplification (LAMP) of parasite DNA. *Int J Parasitol*, 38, 589-599.
24. Suzuki, R., Ihira, M., Enomoto, Y., Yano, H., Maruyama, F., Emi, N., Asano, Y. and Yoshikawa, T. (2010) Heat denaturation increases the sensitivity of the cytomegalovirus loop-mediated isothermal amplification method. *Microbiol Immunol*, 54, 466-470.
25. Verkooyen, R. P., Luijendijk, A., Huisman, W. M., Goessens, W. H., Kluytmans, J. A., van Rijsoort-Vos, J. H. and Verbrugh, H. A. (1996) Detection of PCR inhibitors in cervical specimens by using the AMPLICOR *Chlamydia trachomatis* assay. *Journal of clinical microbiology*, 34, 3072-3074.
26. Modak, S. S., Barber, C. A., Geva, E., Abrams, W. R., Malamud, D. and Ongagna, Y. S. (2016) Rapid Point-of-Care Isothermal Amplification Assay for the Detection of Malaria without Nucleic Acid Purification. *Infect Dis (Auckl)*, 9, 1-9.
27. Fereidouni, S. R., Starick, E., Ziller, M., Harder, T. C., Unger, H., Hamilton, K. and Globig, A. (2015) Sample preparation for avian and porcine influenza virus cDNA amplification simplified: Boiling vs. conventional RNA extraction. *J Virol Methods*, 221, 62-67.
28. Queipo-Ortuno, M. I., De Dios Colmenero, J., Macias, M., Bravo, M. J. and Morata, P. (2008) Preparation of bacterial DNA template by boiling and effect of immunoglobulin G as an inhibitor in real-time PCR for serum samples from patients with brucellosis. *Clin Vaccine Immunol*, 15, 293-296.
29. Chander, Y., Koelbl, J., Puckett, J., Moser, M. J., Klingele, A. J., Liles, M. R., Carrias, A., Mead, D. A. and Schoenfeld, T. W. (2014) A novel thermostable polymerase for RNA and DNA loop-mediated isothermal amplification (LAMP). *Front Microbiol*, 5, 395.
30. Ignatov, K. B., Barsova, E. V., Fradkov, A. F., Blagodatskikh, K. A., Kramarova, T. V. and Kramarov, V. M. (2014) A strong strand displacement activity of thermostable DNA polymerase markedly improves the results of DNA amplification. *Biotechniques*, 57, 81-87.
31. Ghadessy, F. J., Ong, J. L. and Holliger, P. (2001) Directed evolution of polymerase function by compartmentalized self-replication. *Proceedings of the National Academy of Sciences of the United States of America*, 98, 4552-4557.
32. Baar, C., d'Abbadie, M., Vaisman, A., Arana, M. E., Hofreiter, M., Woodgate, R., Kunkel, T. A. and Holliger, P. (2011) Molecular breeding of polymerases for resistance to environmental inhibitors. *Nucleic acids research*, 39, e51.
33. Chen, T. and Romesberg, F. E. (2014) Directed polymerase evolution. *FEBS Lett*, 588, 219-229.
34. Meyer, A. J., Ellefson, J. W. and Ellington, A. D. (2015) Directed Evolution of a Panel of Orthogonal T7 RNA Polymerase Variants for in Vivo or in Vitro Synthetic Circuitry. *ACS synthetic biology*, 4, 1070-1076.
35. Ellefson, J. W., Gollihar, J., Shroff, R., Shivram, H., Iyer, V. R. and Ellington, A. D. (2016) Synthetic evolutionary origin of a proofreading reverse transcriptase. *Science*, 352, 1590-1593.
36. Povilaitis, T., Alzbutas, G., Sukackaite, R., Siurkus, J. and Skirgaila, R. (2016) In vitro evolution of phi29 DNA polymerase using isothermal compartmentalized self replication technique. *Protein Eng Des Sel*.
37. Lutz, R. and Bujard, H. (1997) Independent and Tight Regulation of Transcriptional Units in *Escherichia coli* Via the LacR/O, the TetR/O and AraC/I1/I2 Regulatory Elements. *Nucleic acids research*, 25, 1203-1210.
38. Kostner, M., Schmidt, B., Bertram, R. and Hillen, W. (2006) Generating tetracycline-inducible auxotrophy in *Escherichia coli* and *Salmonella enterica* serovar *Typhimurium* by using an insertion element and a hyperactive transposase. *Applied and environmental microbiology*, 72, 4717-4725.
39. Korolev, S., Nayal, M., Barnes, W. M., Di Cera, E. and Waksman, G. (1995) Crystal structure of the large fragment of *Thermus aquaticus* DNA polymerase I at 2.5-A resolution: structural basis for thermostability. *Proceedings of the National Academy of Sciences of the United States of America*, 92, 9264-9268.
40. Milligan, J. N. and Garry, D. J. (2017) Shuffle Optimizer: A Program to Optimize DNA Shuffling for Protein Engineering. *Methods Mol Biol*, 1472, 35-45.
41. Berman, H. M., Westbrook, J., Feng, Z., Gilliland, G., Bhat, T. N., Weissig, H., Shindyalov, I. N. and Bourne, P. E. (2000) The Protein Data Bank. *Nucleic acids research*, 28, 235-242.
42. Kiefer, J. R., Mao, C., Braman, J. C. and Beese, L. S. (1998) Visualizing DNA replication in a catalytically active *Bacillus* DNA polymerase crystal. *Nature*, 391, 304-307.
43. Li, Y., Korolev, S. and Waksman, G. (1998) Crystal structures of open and closed forms of binary and ternary complexes of the large fragment of *Thermus aquaticus* DNA polymerase I: structural basis for nucleotide incorporation. *EMBO J*, 17, 7514-7525.
44. Ellefson, J. W., Meyer, A. J., Hughes, R. A., Cannon, J. R., Brodbelt, J. S. and Ellington, A. D. (2014) Directed evolution of genetic parts and circuits by compartmentalized partnered replication. *Nature biotechnology*, 32, 97-101.
45. An, L., Tang, W., Ranalli, T. A., Kim, H. J., Wytiaz, J. and Kong, H. (2005) Characterization of a thermostable UvrD helicase and its participation in helicase-dependent amplification. *The Journal of biological chemistry*, 280, 28952-28958.
46. Chen, T., Hongdilokkul, N., Liu, Z., Adhikary, R., Tsuen, S. S. and Romesberg, F. E. (2016) Evolution of thermophilic DNA polymerases for the recognition and amplification of C2'-modified DNA. *Nature chemistry*, 8, 556-562.
47. Stemmer, W. P. (1994) DNA shuffling by random fragmentation and reassembly: in vitro recombination for molecular evolution. *Proceedings of the National Academy of Sciences of the United States of America*, 91, 10747-10751.

48. Crameri, A., Raillard, S. A., Bermudez, E. and Stemmer, W. P. (1998) DNA shuffling of a family of genes from diverse species accelerates directed evolution. *Nature*, 391, 288-291.
49. Lawyer, F. C., Stoffel, S., Saiki, R. K., Chang, S. Y., Landre, P. A., Abramson, R. D. and Gelfand, D. H. (1993) High-level expression, purification, and enzymatic characterization of full-length *Thermus aquaticus* DNA polymerase and a truncated form deficient in 5' to 3' exonuclease activity. *PCR Methods Appl*, 2, 275-287.
50. Moore, G. L. and Maranas, C. D. (2000) Modeling DNA mutation and recombination for directed evolution experiments. *Journal of theoretical biology*, 205, 483-503.
51. Moore, G. L. and Maranas, C. D. (2002) eCodonOpt: a systematic computational framework for optimizing codon usage in directed evolution experiments. *Nucleic acids research*, 30, 2407-2416.
52. Moore, G. L., Maranas, C. D., Lutz, S. and Benkovic, S. J. (2001) Predicting crossover generation in DNA shuffling. *Proceedings of the National Academy of Sciences of the United States of America*, 98, 3226-3231.
53. Hoheisel, J. D. (1993) On the activities of *Escherichia coli* exonuclease III. *Analytical biochemistry*, 209, 238-246.
54. Roychoudhury, R. and Wu, R. (1977) Novel properties of *Escherichia coli* exonuclease III. *The Journal of biological chemistry*, 252, 4786-4789.
55. James, C. D. and Leffak, I. M. (1984) Replacement synthesis labeling of DNA molecules in vitro using the *Escherichia coli* exonuclease III/DNA polymerase I enzyme pair. *Analytical biochemistry*, 141, 33-37.
56. Laos, R., Shaw, R., Leal, N. A., Gaucher, E. and Benner, S. (2013) Directed evolution of polymerases to accept nucleotides with nonstandard hydrogen bond patterns. *Biochemistry*, 52, 5288-5294.
57. Leconte, A. M., Patel, M. P., Sass, L. E., McInerney, P., Jarosz, M., Kung, L., Bowers, J. L., Buzby, P. R., Efcavitch, J. W. and Romesberg, F. E. (2010) Directed evolution of DNA polymerases for next-generation sequencing. *Angewandte Chemie*, 49, 5921-5924.
58. Suzuki, M., Baskin, D., Hood, L. and Loeb, L. A. (1996) Random mutagenesis of *Thermus aquaticus* DNA polymerase I: concordance of immutable sites in vivo with the crystal structure. *Proceedings of the National Academy of Sciences of the United States of America*, 93, 9670-9675.
59. Vichier-Guerre, S., Ferris, S., Auberger, N., Mahiddine, K. and Jestin, J. L. (2006) A population of thermostable reverse transcriptases evolved from *Thermus aquaticus* DNA polymerase I by phage display. *Angewandte Chemie*, 45, 6133-6137.
60. Ghadessy, F. J., Ramsay, N., Boudsocq, F., Loakes, D., Brown, A., Iwai, S., Vaisman, A., Woodgate, R. and Holliger, P. (2004) Generic expansion of the substrate spectrum of a DNA polymerase by directed evolution. *Nature biotechnology*, 22, 755-759.
61. Patel, P. H., Kawate, H., Adman, E., Ashbach, M. and Loeb, L. A. (2001) A single highly mutable catalytic site amino acid is critical for DNA polymerase fidelity. *The Journal of biological chemistry*, 276, 5044-5051.
62. Aryan, E., Makvandi, M., Farajzadeh, A., Huygen, K., Bifani, P., Mousavi, S. L., Fateh, A., Jelodar, A., Gouya, M. M. and Romano, M. (2010) A novel and more sensitive loop-mediated isothermal amplification assay targeting IS6110 for detection of *Mycobacterium tuberculosis* complex. *Microbiological research*, 165, 211-220.
63. Sagner, G., Ruger, R. and Kessler, C. (1991) Rapid filter assay for the detection of DNA polymerase activity: direct identification of the gene for the DNA polymerase from *Thermus aquaticus*. *Gene*, 97, 119-123.
64. Kong, H., Kucera, R. B. and Jack, W. E. (1993) Characterization of a DNA polymerase from the hyperthermophile archaea *Thermococcus litoralis*. Vent DNA polymerase, steady state kinetics, thermal stability, processivity, strand displacement, and exonuclease activities. *The Journal of biological chemistry*, 268, 1965-1975.
65. Nelson, J. R., Cai, Y. C., Giesler, T. L., Farchaus, J. W., Sundaram, S. T., Ortiz-Rivera, M., Hosta, L. P., Hewitt, P. L., Mamone, J. A., Palaniappan, C. et al. (2002) TempliPhi, phi29 DNA polymerase based rolling circle amplification of templates for DNA sequencing. *Biotechniques*, Suppl, 44-47.
66. Reagin, M. J., Giesler, T. L., Merla, A. L., Resetar-Gerke, J. M., Kapolka, K. M. and Mamone, J. A. (2003) TempliPhi: A sequencing template preparation procedure that eliminates overnight cultures and DNA purification. *J Biomol Tech*, 14, 143-148.
67. Ramalingam, N., San, T. C., Kai, T. J., Mak, M. Y. M. and Gong, H.-Q. (2009) Microfluidic devices harboring unsealed reactors for real-time isothermal helicase-dependent amplification. *Microfluidics and Nanofluidics*, 7, 325-336.
68. Mahalanabis, M., Do, J., H, A. L., Zhang, J. Y. and Klapperich, C. M. (2010) An integrated disposable device for DNA extraction and helicase dependent amplification. *Biomed Microdevices*, 12, 353-359.
69. Borysiak, M. D., Kimura, K. W. and Posner, J. D. (2015) NAIL: Nucleic Acid detection using Isotachophoresis and Loop-mediated isothermal amplification. *Lab on a chip*, 15, 1697-1707.
70. Kim, T. H., Park, J., Kim, C. J. and Cho, Y. K. (2014) Fully integrated lab-on-a-disc for nucleic acid analysis of food-borne pathogens. *Analytical chemistry*, 86, 3841-3848.
71. Liu, C., Geva, E., Mauk, M., Qiu, X., Abrams, W. R., Malamud, D., Curtis, K., Owen, S. M. and Bau, H. H. (2011) An isothermal amplification reactor with an integrated isolation membrane for point-of-care detection of infectious diseases. *The Analyst*, 136, 2069-2076.
72. Wu, Q., Jin, W., Zhou, C., Han, S., Yang, W., Zhu, Q., Jin, Q. and Mu, Y. (2011) Integrated glass microdevice for nucleic acid purification, loop-mediated isothermal amplification, and online detection. *Analytical chemistry*, 83, 3336-3342.

Reference List #2

1. Lizardi, P. M., Huang, X., Zhu, Z., Bray-Ward, P., Thomas, D. C. and Ward, D. C. (1998) Mutation detection and single-molecule counting using isothermal rolling-circle amplification. Nature genetics, 19, 225-232.
2. Zhang, D. Y., Zhang, W., Li, X. and Konomi, Y. (2001) Detection of rare DNA targets by isothermal ramification amplification. Gene, 274, 209-216.
3. Zhao, Y., Chen, F., Li, Q., Wang, L. and Fan, C. (2015) Isothermal Amplification of Nucleic Acids. Chemical reviews, 115, 12491-12545.
4. Chen, T. and Romesberg, F. E. (2014) Directed polymerase evolution. FEBS Lett, 588, 219-229.
5. Ghadessy, F. J., Ong, J. L. and Holliger, P. (2001) Directed evolution of polymerase function by compartmentalized self-replication. Proceedings of the National Academy of Sciences of the United States of America, 98, 4552-4557.
6. Laos, R., Shaw, R., Leal, N. A., Gaucher, E. and Benner, S. (2013) Directed evolution of polymerases to accept nucleotides with nonstandard hydrogen bond patterns. Biochemistry, 52, 5288-5294.
7. Leconte, A. M., Patel, M. P., Sass, L. E., McInerney, P., Jarosz, M., Kung, L., Bowers, J. L., Buzby, P. R., Efcavitch, J. W. and Romesberg, F. E. (2010) Directed evolution of DNA polymerases for next-generation sequencing. Angewandte Chemie, 49, 5921-5924.
8. Suzuki, M., Baskin, D., Hood, L. and Loeb, L. A. (1996) Random mutagenesis of Thermus aquaticus DNA polymerase I: concordance of immutable sites in vivo with the crystal structure. Proceedings of the National Academy of Sciences of the United States of America, 93, 9670-9675.
9. Vichier-Guerre, S., Ferris, S., Auberger, N., Mahiddine, K. and Jestin, J. L. (2006) A population of thermostable reverse transcriptases evolved from Thermus aquaticus DNA polymerase I by phage display. Angewandte Chemie, 45, 6133-6137.
10. Ignatov, K. B., Barsova, E. V., Fradkov, A. F., Blagodatskikh, K. A., Kramarova, T. V. and Kramarov, V. M. (2014) A strong strand displacement activity of thermostable DNA polymerase markedly improves the results of DNA amplification. Biotechniques, 57, 81-87.

Reference List #3

1. Notomi, T.; Okayama, H.; Masubuchi, H.; Yonekawa, T.; Watanabe, K.; Amino, N.; Hase, T., Loop-mediated isothermal amplification of DNA. Nucleic Acids Research 2000, 28, (12).
2. Nagamine, K.; Kuzuhara, Y.; Notomi, T., Isolation of single-stranded DNA from loop-mediated isothermal amplification products. Biochemical and Biophysical Research Communications 2002, 290, (4), 1195-1198.
3. Tomita, N.; Mori, Y.; Kanda, H.; Notomi, T., Loop-mediated isothermal amplification (LAMP) of gene sequences and simple visual detection of products. Nature Protocols 2008, 3, (5), 877-882.
4. Nagamine, K.; Hase, T.; Notomi, T., Accelerated reaction by loop-mediated isothermal amplification using loop primers. Molecular and Cellular Probes 2002, 16, (3), 223-229.
5. Mair, G.; Vilei, E. M.; Wade, A.; Frey, J.; Unger, H., Isothermal loop-mediated amplification (lamp) for diagnosis of contagious bovine pleuro-pneumonia. Bmc Veterinary Research 2013, 9.
6. Tanner, N. A.; Zhang, Y. H.; Evans, T. C., Simultaneous multiple target detection in real-time loop-mediated isothermal amplification. Biotechniques 2012, 53, (2), 81-+.
7. Suwancharoen, D.; Sittiwicheanwong, B.; Wiratsudakul, A., Evaluation of loop-mediated isothermal amplification method (LAMP) for pathogenic Leptospira spp. detection with leptospires isolation and real-time PCR. Journal of Veterinary Medical Science 2016, 78, (8), 1299-1302.
8. Wang, Y.; Li, D. X.; Wang, Y.; Li, K. W.; Ye, C. Y., Rapid and Sensitive Detection of Vibrio parahaemolyticus and Vibrio vulnificus by Multiple Endonuclease Restriction Real-Time Loop-Mediated Isothermal Amplification Technique. Molecules 2016, 21, (1).
9. Abdulmawjood, A.; Wickhorst, J.; Hashim, O.; Sammra, O.; Hassan, A. A.; Alssahen, M.; Lammler, C.; Prenger-Berninghoff, E.; Klein, G., Application of a loop-mediated isothermal amplification (LAMP) assay for molecular identification of Trueperella pyogenes isolated from various origins. Molecular and Cellular Probes 2016, 30, (4), 205-210.
10. Song, J. Z.; Mauk, M. G.; Hackett, B. A.; Cherry, S.; Bau, H. H.; Liu, C. C., Instrument-Free Point-of-Care Molecular Detection of Zika Virus. Analytical Chemistry 2016, 88, (14), 7289-7294.
11. Kong, X. J.; Qin, W. T.; Huang, X. Q.; Kong, F. F.; Schoen, C. D.; Feng, J.; Wang, Z. Y.; Zhang, H., Development and application of loop-mediated isothermal amplification (LAMP) for detection of Plasmopara viticola. Scientific Reports 2016, 6.
12. Zhang, C.; Yao, Y.; Zhu, J. L.; Zhang, S. N.; Zhang, S. S.; Wei, H.; Hui, W. L.; Cui, Y. L., Establishment and application of a real-time loop-mediated isothermal amplification system for the detection of CYP2C19 polymorphisms. Scientific Reports 2016, 6.
13. Boczkowska, M.; Guga, P.; Stec, W. J., Stereodefined phosphorothioate analogues of DNA: Relative thermodynamic stability of the model PS-DNA/DNA and PS-DNA/RNA complexes. Biochemistry 2002, 41, (41), 12483-12487.
14. Jung C; A. D, E., A primeness molecular diagnostic: phosphorothioated-terminal hairpin formation and self-priming extension (PS-THSP). Analytical and Bioanalytical Chemistry 2016, DOI: 10.1007/s00216-016-9479-y.
15. Laplanche, L. A.; James, T. L.; Powell, C.; Wilson, W. D.; Uznanski, B.; Stec, W. J.; Summers, M. F.; Zon, G., Phosphorothioate-Modified Oligodeoxyribonucleotides 0.3. Nmr and Uv Spectroscopic Studies of the Rp-Rp, Sp-Sp, and Rp-Sp Duplexes, [D(Ggsaattcc)]2, Derived from Diastereomeric 0-Ethyl Phosphorothioates. Nucleic Acids Research 1986, 14, (22), 9081-9093.
16. Bhadra, S.; Jiang, Y. S.; Kumar, M. R.; Johnson, R. F.; Hensley, L. E.; Ellington, A. D., Real-Time Sequence-Validated Loop-Mediated Isothermal Amplification Assays for Detection of Middle East Respiratory Syndrome Coronavirus (MERS-CoV). Plos One 2015, 10, (4).
17. Singer, A.; Kuhn, H.; Frank-Kamenetskii, M.; Meller, A., Detection of urea-induced internal denaturation of dsDNA using solid-state nanopores. Journal of Physics-Condensed Matter 2010, 22, (45).
18. Conway, B. E., Effect of Urea on the Viscosity of Deoxyribonucleic Acid Solutions. Journal of Polymer Science 1956, 20, (95), 299-306.
19. Schwinefus, J. J.; Engelsgjerd, S.; Mangold, K.; Thompson, P., Urea Induced DNA Denaturation. Biophysical Journal 2013, 104, (2), 425a-425a.
20. Chang, Y. X.; Gong, L.; Yuan, W. Y.; Li, X. W.; Chen, G. X.; Li, X. H.; Zhang, Q. F.; Wu, C. Y., Replication Protein A (RPA 1 a) Is Required for Meiotic and Somatic DNA Repair But Is Dispensable for DNA Replication and Homologous Recombination in Rice. Plant Physiology 2009, 151, (4), 2162-2173.
21. Zhu, Z. Y.; Ravelet, C.; Perrier, S.; Guieu, V.; Fiore, E.; Peyrin, E., Single-Stranded DNA Binding Protein-Assisted Fluorescence Polarization Aptamer Assay for Detection of Small Molecules. Analytical Chemistry 2012, 84, (16), 7203-7211.
22. Shlyakhtenko, L. S.; Lushnikov, A. Y.; Miyagi, A.; Lyubchenko, Y. L., Specificity of Binding of Single-Stranded DNA-Binding Protein to Its Target. Biochemistry 2012, 51, (7), 1500-1509.

23. Rogers, K.; Hobgood, M.; Nance, J.; Cline, D.; Browning, S.; Eason, M.; Eversburg, A.; Lawson, N.; Campbell, L.; Wilhelm, D.; Karpel, R., Structural modeling of Gene 32 protein and SSB's roles in DNA replication, recombination and repair. *Faseb Journal* 2010, 24.
24. Zahran, M.; Berezniak, T.; Imhof, P.; Smith, J. C., Role of magnesium ions in DNA recognition by the EcoRV restriction endonuclease. *Febs Letters* 2011, 585, (17), 2739-2743.
25. Sissi, C.; Palumbo, M., Effects of magnesium and related divalent metal ions in topoisomerase structure and function. *Nucleic Acids Research* 2009, 37, (3), 702-711.
26. Kato, T.; Liang, X. G.; Asanuma, H., Model of Elongation of Short DNA Sequence by Thermophilic DNA Polymerase under Isothermal Conditions. *Biochemistry* 2012, 51, (40), 7846-7853.

What is claimed is:

1. A non-naturally occurring thermostable polymerase, wherein the thermostable polymerase has at least 97% sequence identity to SEQ ID NO: 1.

2. The non-naturally occurring thermostable polymerase of claim 1, wherein the polymerase is stored in a storage buffer, or a reaction buffer.

3. The non-naturally occurring thermostable polymerase of claim 2, wherein the buffer further comprises temperature dependent inhibitor of polymerase activity.

4. A nucleic acid encoding the non-naturally occurring thermostable polymerase of claim 1.

5. A kit comprising the non-naturally occurring thermostable polymerase of claim 1.

6. The kit of claim 5, wherein the kit further comprises at least four distinct primers.

7. The kit of claim 6, wherein at least one of the primers is phosphorothioated.

8. The kit of claim 5, wherein the kit further comprises a buffer solution.

* * * * *